United States Patent
Wood et al.

(10) Patent No.: US 8,449,172 B2
(45) Date of Patent: *May 28, 2013

(54) MIXING DEVICE FOR CREATING AN OUTPUT MIXTURE BY MIXING A FIRST MATERIAL AND A SECOND MATERIAL

(75) Inventors: Anthony B. Wood, Dallas, TX (US); Gregory J. Archambeau, Puyallup, WA (US); Richard L. Watson, McPherson, KS (US)

(73) Assignee: Revalesio Corporation, Tacoma, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/945,703

(22) Filed: Nov. 12, 2010

(65) Prior Publication Data

US 2011/0104804 A1 May 5, 2011

Related U.S. Application Data

(63) Continuation of application No. 11/924,589, filed on Oct. 25, 2007, now Pat. No. 7,832,920.

(60) Provisional application No. 60/982,387, filed on Oct. 24, 2007, provisional application No. 60/862,955, filed on Oct. 25, 2006, provisional application No. 60/862,904, filed on Oct. 25, 2006.

(51) Int. Cl.
*B01F 7/12* (2006.01)

(52) U.S. Cl.
USPC ............... 366/170.3; 366/171.1; 366/172.1; 366/305

(58) Field of Classification Search
USPC ........... 366/64, 96–99, 168.1, 169.1, 170.1, 366/170.3, 165.1, 171.1, 172.1, 172.2, 176.1, 366/181.4, 181.7, 262–266, 302, 305, 348
See application file for complete search history.

(56) References Cited

U.S. PATENT DOCUMENTS

| | | | |
|---|---|---|---|
| 1,627,161 A | 5/1927 | Edwards | |
| 1,650,561 A | 11/1927 | Williams | |

(Continued)

FOREIGN PATENT DOCUMENTS

| | | |
|---|---|---|
| CN | 1499977 | 5/2004 |
| DE | 1557171 | 7/1970 |

(Continued)

OTHER PUBLICATIONS

U.S. Appl. No. 13/097,565, filed Apr. 29, 2011, Watson.
U.S. Appl. No. 13/126,117, filed Jul. 19, 2011, Watson.
Auclair et al., "Revisiting the Mechanism of P450 Enzymes with the Radical Clocks Norcarane and Spiro[2,5]octane," Journal of the American Chemical Society, 124(21):6020-6027, 2002.
Austin et al., "The Non-Heme Diiron Alkane Monooxygenase of *Pseudomonas oleovorans* (AlkB) Hydroxylates via a Substrate Radical Intermediate," Journal of the American Chemical Society, 122:11747-11748, 2000.

(Continued)

*Primary Examiner* — Charles E Cooley
(74) *Attorney, Agent, or Firm* — Barry L. Davison; Davis Wright Tremaine LLP

(57) ABSTRACT

A mixing device for mixing a first and second material together to create an output mixture. The device includes a first chamber containing the first material coupled to a mixing chamber defined between a rotor and a stator. The rotor is disposed inside the stator and rotates therein about an axis of rotation. The first chamber houses an internal pump configured to pump the first material from the first chamber into the mixing chamber. The pump may be configured to impart a circumferential velocity into the first material before it enters the mixing chamber. At least one of the rotor and stator have a plurality of through-holes through which the second material is provided to the mixing chamber. Optionally, a second chamber is coupled to the mixing chamber. The second chamber may house an internal pump configured to pump the output material from the mixing chamber into the second chamber.

24 Claims, 27 Drawing Sheets

U.S. PATENT DOCUMENTS

| | | | |
|---|---|---|---|
| 1,650,612 A | | 11/1927 | Deniston |
| 1,711,154 A | | 4/1929 | Michal |
| 2,115,123 A | | 4/1938 | Russell |
| 2,159,670 A | * | 5/1939 | Neitzke .................. 366/196 |
| 2,278,051 A | * | 3/1942 | Ambrose ................. 241/97 |
| 2,591,966 A | * | 4/1952 | Rider ..................... 366/286 |
| 2,606,502 A | | 8/1952 | Carlson |
| 2,639,901 A | | 5/1953 | Teale |
| 2,688,470 A | | 9/1954 | Marco |
| 2,734,728 A | | 2/1956 | Myers |
| 2,798,698 A | | 7/1957 | Dooley |
| 2,960,318 A | * | 11/1960 | Caillaud ................. 366/181.7 |
| 2,969,960 A | * | 1/1961 | Gurley, Jr. .............. 366/303 |
| 2,970,817 A | * | 2/1961 | Gurley, Jr. .............. 366/305 |
| 2,995,346 A | * | 8/1961 | Samples ................. 366/98 |
| 3,174,185 A | | 3/1965 | Gerber |
| 3,182,975 A | | 5/1965 | Stewart |
| 3,194,540 A | | 7/1965 | Hager |
| 3,332,631 A | * | 7/1967 | Wood ..................... 241/172 |
| 3,333,771 A | | 8/1967 | Graham |
| 3,333,828 A | * | 8/1967 | Boehme .................. 366/305 |
| 3,471,131 A | * | 10/1969 | Fritzweiler et al. ...... 366/305 |
| 3,514,079 A | * | 5/1970 | Little, Jr. ................ 366/305 |
| 3,653,637 A | * | 4/1972 | Eckardt .................. 425/209 |
| 3,660,933 A | | 5/1972 | Wong, Jr. |
| 3,744,763 A | | 7/1973 | Schnoring |
| 3,791,349 A | | 2/1974 | Schaefer |
| 3,925,243 A | | 12/1975 | Brogli |
| 3,937,445 A | | 2/1976 | Agosta |
| 3,938,783 A | | 2/1976 | Porter |
| 3,939,073 A | | 2/1976 | Bats |
| 3,980,280 A | | 9/1976 | Benson |
| 3,986,709 A | | 10/1976 | Vermeulen |
| 3,996,012 A | | 12/1976 | Zucker |
| 3,998,433 A | | 12/1976 | Iwako |
| 4,004,553 A | | 1/1977 | Stenstrom |
| 4,011,027 A | | 3/1977 | Selder |
| 4,014,526 A | | 3/1977 | Cramer |
| 4,049,240 A | | 9/1977 | Walters |
| 4,051,204 A | | 9/1977 | Muller |
| 4,057,223 A | | 11/1977 | Rosenberger |
| 4,057,933 A | | 11/1977 | Enyeart |
| 4,069,147 A | | 1/1978 | Abrams |
| 4,071,225 A | | 1/1978 | Holl |
| 4,089,507 A | | 5/1978 | Arai |
| 4,097,026 A | | 6/1978 | Haindl |
| 4,116,164 A | | 9/1978 | Shabi |
| 4,117,550 A | | 9/1978 | Folland |
| 4,127,332 A | | 11/1978 | Thiruvengadam |
| 4,128,342 A | * | 12/1978 | Renk ...................... 366/99 |
| 4,136,971 A | | 1/1979 | Varlamov |
| 4,143,639 A | | 3/1979 | Frenette |
| 4,144,167 A | | 3/1979 | Burkett |
| 4,159,944 A | | 7/1979 | Erickson |
| 4,162,153 A | | 7/1979 | Spector |
| 4,163,712 A | | 8/1979 | Smith |
| 4,172,668 A | | 10/1979 | Thompson |
| 4,175,873 A | | 11/1979 | Iwako |
| 4,183,681 A | | 1/1980 | Li |
| 4,201,487 A | | 5/1980 | Backhaus |
| 4,213,712 A | | 7/1980 | Aanonsen |
| 4,261,521 A | | 4/1981 | Ashbrook |
| 4,263,003 A | | 4/1981 | Vork |
| 4,284,623 A | | 8/1981 | Beck |
| 4,289,733 A | | 9/1981 | Saito |
| 4,294,549 A | | 10/1981 | Thompson |
| 4,316,673 A | | 2/1982 | Speer |
| 4,318,429 A | | 3/1982 | Gouttebessis |
| 4,332,486 A | | 6/1982 | Mutalibov |
| 4,361,414 A | | 11/1982 | Nemes |
| 4,368,986 A | | 1/1983 | Fischer |
| 4,383,767 A | | 5/1983 | Jido |
| 4,388,915 A | * | 6/1983 | Shafran .................. 126/247 |
| 4,393,017 A | | 7/1983 | Kim |
| 4,394,966 A | | 7/1983 | Snyder |
| 4,408,890 A | | 10/1983 | Beckmann |
| 4,416,548 A | * | 11/1983 | Carre et al. ............. 366/171.1 |
| 4,424,797 A | | 1/1984 | Perkins |
| 4,436,430 A | | 3/1984 | Mayer |
| 4,441,823 A | | 4/1984 | Power |
| 4,444,510 A | | 4/1984 | Janssen |
| 4,469,595 A | | 9/1984 | Napadow |
| 4,474,479 A | | 10/1984 | Redelman |
| 4,477,338 A | | 10/1984 | Hellmann |
| 4,507,285 A | | 3/1985 | Kuhne |
| 4,509,861 A | | 4/1985 | Sjonell |
| 4,533,254 A | | 8/1985 | Cook |
| 4,539,139 A | | 9/1985 | Ichikawa |
| 4,550,022 A | | 10/1985 | Garabedian |
| 4,594,228 A | | 6/1986 | Lambert |
| 4,619,072 A | | 10/1986 | Privett |
| 4,633,909 A | | 1/1987 | Louboutin |
| 4,634,675 A | | 1/1987 | Freedman |
| 4,645,606 A | | 2/1987 | Ashbrook |
| 4,661,243 A | | 4/1987 | Hotz |
| 4,663,055 A | | 5/1987 | Ling |
| 4,664,680 A | | 5/1987 | Weber |
| 4,684,614 A | | 8/1987 | Krovak |
| 4,687,579 A | | 8/1987 | Bergman |
| 4,696,283 A | | 9/1987 | Kohlmetz |
| 4,715,274 A | | 12/1987 | Paoletti |
| 4,733,972 A | | 3/1988 | Weis |
| 4,735,133 A | | 4/1988 | Paoletti |
| 4,749,493 A | | 6/1988 | Hicks |
| 4,753,535 A | | 6/1988 | King |
| 4,764,283 A | | 8/1988 | Ashbrook |
| 4,765,807 A | | 8/1988 | Henriksen |
| 4,778,336 A | | 10/1988 | Husain |
| 4,793,247 A | | 12/1988 | Verweij |
| 4,798,176 A | | 1/1989 | Perkins |
| 4,808,007 A | | 2/1989 | King |
| 4,820,381 A | * | 4/1989 | Brown ................... 162/261 |
| 4,834,545 A | | 5/1989 | Inoue |
| 4,838,699 A | | 6/1989 | Jour |
| 4,880,445 A | | 11/1989 | Watten |
| 4,884,892 A | | 12/1989 | Gust |
| 4,886,368 A | * | 12/1989 | King ..................... 366/155.1 |
| 4,906,574 A | | 3/1990 | Erdei |
| 4,908,101 A | * | 3/1990 | Frisk et al. ............. 162/261 |
| 4,937,004 A | | 6/1990 | Mandrin |
| 4,957,626 A | | 9/1990 | Ashbrook |
| 4,972,801 A | | 11/1990 | Hunt |
| 4,973,168 A | | 11/1990 | Chan |
| 4,976,547 A | | 12/1990 | Hisanaga |
| 4,999,015 A | | 3/1991 | Demaris |
| 5,005,982 A | | 4/1991 | Kistner |
| 5,006,352 A | | 4/1991 | Zelenak nee Zoltai |
| 5,024,647 A | | 6/1991 | Jubin |
| 5,052,813 A | | 10/1991 | Latto |
| 5,075,234 A | * | 12/1991 | Tunac .................... 435/301.1 |
| 5,141,328 A | * | 8/1992 | Dilley ................... 366/305 |
| 5,152,212 A | | 10/1992 | Chauveau |
| 5,176,447 A | | 1/1993 | Bata |
| 5,185,081 A | | 2/1993 | Nyman |
| 5,188,090 A | * | 2/1993 | Griggs ................... 126/247 |
| 5,205,647 A | * | 4/1993 | Ricciardi ................ 366/328.2 |
| 5,263,774 A | * | 11/1993 | Delcourt ................. 366/305 |
| 5,275,486 A | | 1/1994 | Fissenko |
| 5,279,262 A | | 1/1994 | Muehleck |
| 5,279,463 A | | 1/1994 | Holl |
| 5,281,341 A | | 1/1994 | Reimers |
| 5,304,001 A | | 4/1994 | Kuo |
| 5,318,702 A | | 6/1994 | Ashbrook |
| 5,326,484 A | | 7/1994 | Nakashima |
| 5,341,692 A | | 8/1994 | Sher |
| 5,341,768 A | | 8/1994 | Pope |
| 5,366,288 A | | 11/1994 | Dahllof |
| 5,370,824 A | | 12/1994 | Nagano |
| 5,372,424 A | | 12/1994 | Lecouturier |
| 5,378,321 A | * | 1/1995 | Delcourt ................. 162/57 |
| 5,380,089 A | | 1/1995 | Karasawa |
| 5,380,471 A | | 1/1995 | Ban |
| 5,403,089 A | | 4/1995 | Kuo |
| 5,407,637 A | | 4/1995 | Gibboney |
| 5,419,306 A | | 5/1995 | Huffman |
| 5,435,913 A | | 7/1995 | Ashbrook |
| 5,450,368 A | | 9/1995 | Kubota |

| | | |
|---|---|---|
| 5,470,153 A | 11/1995 | De Naeghel |
| 5,474,380 A | 12/1995 | Sukup |
| 5,482,369 A | 1/1996 | Verstallen |
| 5,496,108 A | 3/1996 | Sukup |
| 5,511,877 A | 4/1996 | King |
| 5,538,191 A | 7/1996 | Holl |
| 5,538,343 A * | 7/1996 | Tynan ............................ 366/305 |
| 5,551,859 A | 9/1996 | Cantrill |
| 5,552,133 A | 9/1996 | Lambert |
| 5,556,765 A | 9/1996 | Dedolph |
| 5,560,710 A | 10/1996 | Klocke |
| 5,561,944 A | 10/1996 | Ismail |
| 5,563,189 A | 10/1996 | Hosokawa |
| 5,569,416 A | 10/1996 | Cross |
| 5,575,559 A | 11/1996 | Roll |
| 5,590,961 A | 1/1997 | Rasmussen |
| 5,616,304 A | 4/1997 | Stormo |
| 5,630,909 A * | 5/1997 | LaRiviere ...................... 162/243 |
| 5,658,380 A | 8/1997 | Dillenbeck |
| 5,665,228 A | 9/1997 | Leaverton |
| 5,671,664 A | 9/1997 | Jacobson |
| 5,674,312 A | 10/1997 | Mazzei |
| 5,697,187 A | 12/1997 | Persinger |
| 5,711,887 A | 1/1998 | Gastman |
| 5,711,950 A | 1/1998 | Lorenzen |
| 5,720,551 A | 2/1998 | Shechter |
| 5,744,105 A | 4/1998 | Stormo |
| 5,766,490 A | 6/1998 | Taylor |
| 5,770,062 A | 6/1998 | Isbell |
| 5,779,996 A | 7/1998 | Stormo |
| 5,782,556 A | 7/1998 | Chu |
| 5,791,778 A | 8/1998 | Manninen |
| 5,810,052 A | 9/1998 | Kozyuk |
| 5,810,474 A | 9/1998 | Hidalgo |
| 5,813,758 A * | 9/1998 | Delcourt et al. ............ 366/171.1 |
| 5,814,222 A | 9/1998 | Zelenak |
| 5,823,671 A | 10/1998 | Mitchell |
| 5,845,993 A | 12/1998 | Shirtum |
| 5,851,068 A | 12/1998 | Rumph |
| 5,863,120 A * | 1/1999 | Gallagher et al. ......... 366/171.1 |
| 5,865,537 A | 2/1999 | Streiff |
| 5,868,495 A | 2/1999 | Hidalgo |
| 5,868,944 A | 2/1999 | Wright |
| 5,885,467 A | 3/1999 | Zelenak |
| 5,887,383 A | 3/1999 | Soeda |
| 5,893,337 A | 4/1999 | Sevic |
| 5,902,042 A * | 5/1999 | Imaizumi et al. ........... 366/176.2 |
| 5,904,851 A | 5/1999 | Taylor |
| 5,918,976 A | 7/1999 | Hashimoto |
| 5,921,678 A | 7/1999 | Desai |
| 5,921,679 A | 7/1999 | Muzzio |
| 5,925,292 A | 7/1999 | Ziesenis |
| 5,931,771 A | 8/1999 | Kozyuk |
| 5,938,581 A | 8/1999 | Bibette |
| 5,948,326 A | 9/1999 | Pate |
| 5,951,922 A | 9/1999 | Mazzei |
| 5,957,122 A * | 9/1999 | Griggs .......................... 126/247 |
| 5,971,601 A | 10/1999 | Kozyuk |
| 5,993,752 A | 11/1999 | Kobayashi |
| 5,997,717 A | 12/1999 | Miyashita et al. |
| 6,000,840 A | 12/1999 | Paterson |
| 6,017,447 A | 1/2000 | Wright |
| 6,019,499 A | 2/2000 | Selivanov |
| 6,042,792 A | 3/2000 | Shefer |
| 6,086,243 A | 7/2000 | Paul |
| 6,092,921 A | 7/2000 | Wentinck |
| 6,096,221 A | 8/2000 | Kerchouche |
| 6,110,353 A | 8/2000 | Hough |
| 6,120,008 A | 9/2000 | Littman |
| 6,120,668 A | 9/2000 | Kim |
| 6,135,628 A | 10/2000 | DeStefano |
| 6,173,526 B1 | 1/2001 | Mazzei |
| 6,180,059 B1 | 1/2001 | Divino |
| 6,190,549 B1 | 2/2001 | Schwartz |
| 6,193,786 B1 | 2/2001 | Henderson |
| 6,210,030 B1 | 4/2001 | Ibar |
| 6,228,259 B1 | 5/2001 | Schwartz |
| 6,234,206 B1 | 5/2001 | Malmberg |
| 6,238,645 B1 | 5/2001 | Spears |
| 6,238,706 B1 | 5/2001 | Sonnenschein |
| 6,241,802 B1 | 6/2001 | Spears |
| 6,250,609 B1 | 6/2001 | Cheng |
| 6,257,754 B1 | 7/2001 | Sondergaard |
| 6,276,825 B2 | 8/2001 | Running |
| 6,279,611 B2 | 8/2001 | Uematsu |
| 6,279,882 B1 | 8/2001 | Littman |
| 6,284,293 B1 | 9/2001 | Crandall |
| 6,290,857 B1 | 9/2001 | Brahmbhatt |
| 6,294,212 B1 | 9/2001 | Huber |
| 6,299,343 B1 | 10/2001 | Pekerman |
| 6,312,647 B1 | 11/2001 | Spears |
| 6,315,942 B1 | 11/2001 | Spears |
| 6,332,706 B1 | 12/2001 | Hall |
| 6,338,569 B1 | 1/2002 | McGill |
| 6,344,489 B1 | 2/2002 | Spears |
| 6,366,751 B1 | 4/2002 | Shakuto |
| 6,380,264 B1 | 4/2002 | Jameson |
| 6,382,601 B1 | 5/2002 | Ohnari |
| 6,386,751 B1 * | 5/2002 | Wootan et al. ............. 366/170.3 |
| 6,398,402 B1 | 6/2002 | Thomas |
| 6,402,361 B1 | 6/2002 | Reinemuth |
| 6,412,714 B1 | 7/2002 | Witsken |
| 6,413,418 B2 | 7/2002 | Brahmbhatt |
| 6,431,742 B2 | 8/2002 | Mori |
| 6,443,610 B1 | 9/2002 | Shechter |
| 6,451,328 B1 | 9/2002 | Ionita-Manzatu |
| 6,454,997 B1 | 9/2002 | Divino |
| 6,458,071 B1 | 10/2002 | Jacobson |
| 6,474,264 B1 | 11/2002 | Grimberg |
| 6,474,862 B2 | 11/2002 | Farrell |
| 6,481,649 B1 | 11/2002 | Schmidt |
| 6,485,003 B2 | 11/2002 | Speece |
| 6,488,401 B1 | 12/2002 | Seaman |
| 6,488,765 B1 | 12/2002 | Tseng |
| 6,494,055 B1 | 12/2002 | Meserole |
| 6,499,671 B1 | 12/2002 | Sands |
| 6,521,248 B1 | 2/2003 | Holloway |
| 6,524,475 B1 | 2/2003 | Herrington |
| 6,530,895 B1 | 3/2003 | Keirn |
| 6,538,041 B1 | 3/2003 | Marelli |
| 6,540,436 B2 | 4/2003 | Ogi |
| 6,551,492 B2 | 4/2003 | Hanaoka |
| 6,557,492 B1 | 5/2003 | Robohm |
| 6,576,130 B2 | 6/2003 | Wallace |
| 6,582,387 B2 | 6/2003 | Derek |
| 6,586,441 B2 | 7/2003 | Borroni |
| 6,596,235 B2 | 7/2003 | Divino |
| 6,602,468 B2 | 8/2003 | Patterson |
| 6,613,280 B2 | 9/2003 | Myrick |
| 6,619,399 B1 | 9/2003 | Chatterji |
| 6,627,784 B2 | 9/2003 | Hudson |
| 6,632,014 B2 | 10/2003 | Steinberg |
| 6,649,145 B2 | 11/2003 | McGrath |
| 6,655,830 B1 | 12/2003 | Seaman |
| 6,669,966 B1 | 12/2003 | Antelman |
| 6,676,900 B1 | 1/2004 | Divino |
| 6,682,215 B2 | 1/2004 | Kinsley |
| 6,682,732 B1 | 1/2004 | Blake |
| 6,688,883 B2 | 2/2004 | Tseng |
| 6,689,262 B2 | 2/2004 | Senkiw |
| 6,702,949 B2 * | 3/2004 | Wood ............................ 210/750 |
| 6,705,755 B1 | 3/2004 | Innings |
| 6,730,211 B2 | 5/2004 | Hanaoka |
| 6,733,172 B2 | 5/2004 | Lee |
| 6,749,329 B2 | 6/2004 | Shechter |
| 6,752,529 B2 | 6/2004 | Holl |
| 6,764,213 B2 | 7/2004 | Shechter |
| 6,782,924 B2 | 8/2004 | Daoud |
| 6,796,702 B2 | 9/2004 | Wire |
| 6,821,438 B2 | 11/2004 | Hadley |
| 6,837,986 B2 | 1/2005 | Hanaoka |
| 6,857,774 B2 | 2/2005 | Kozyuk |
| 6,869,212 B2 * | 3/2005 | Uesugi et al. ............. 366/164.6 |
| 6,905,523 B2 | 6/2005 | Vainshelboim |
| 6,910,448 B2 * | 6/2005 | Thoma ............................ 122/26 |
| 6,935,768 B2 | 8/2005 | Lowe |
| 6,935,770 B2 | 8/2005 | Schueler |
| 6,936,179 B2 | 8/2005 | DeWald |

| | | |
|---|---|---|
| 6,936,221 B1 | 8/2005 | Divino |
| 6,955,713 B2 | 10/2005 | Rittner |
| 6,958,163 B2 | 10/2005 | Ionita-Manzatu |
| 6,959,669 B2* | 11/2005 | Thoma ............ 122/26 |
| 6,974,546 B2* | 12/2005 | Wood ............ 210/750 |
| 7,008,535 B1 | 3/2006 | Spears |
| 7,037,842 B2 | 5/2006 | Verhaverbeke |
| 7,069,073 B2 | 6/2006 | Henley |
| 7,089,886 B2* | 8/2006 | Thoma ............ 122/26 |
| 7,090,753 B2 | 8/2006 | Sumita |
| 7,121,714 B2* | 10/2006 | Parker Metcalfe et al. ............ 366/175.1 |
| 7,128,278 B2 | 10/2006 | Archambeau |
| 7,137,620 B2 | 11/2006 | Thomas |
| 7,137,621 B1 | 11/2006 | Bagley |
| 7,179,375 B2* | 2/2007 | Wood ............ 210/195.1 |
| 7,198,254 B2 | 4/2007 | Holloway |
| 7,201,225 B2* | 4/2007 | Smith et al. ............ 166/250.01 |
| 7,223,246 B2 | 5/2007 | Don |
| 7,237,943 B2* | 7/2007 | Brown ............ 366/303 |
| 7,241,723 B2 | 7/2007 | Zhang |
| 7,243,910 B2 | 7/2007 | Bagley |
| 7,255,881 B2 | 8/2007 | Gillis |
| 7,316,501 B2* | 1/2008 | Thoma ............ 366/168.1 |
| 7,334,781 B2* | 2/2008 | Donnelly ............ 261/90 |
| 7,360,755 B2* | 4/2008 | Hudson et al. ............ 261/84 |
| 7,387,262 B2* | 6/2008 | Thoma ............ 237/12.3 R |
| 7,396,441 B2 | 7/2008 | Senkiw |
| 7,654,728 B2* | 2/2010 | Wood et al. ............ 366/170.3 |
| 7,690,833 B2* | 4/2010 | Metcalfe et al. ............ 366/146 |
| 7,749,692 B2 | 7/2010 | Mano |
| 7,770,814 B2 | 8/2010 | Archambeau |
| 7,806,584 B2* | 10/2010 | Wootan et al. ............ 366/170.3 |
| 7,832,920 B2* | 11/2010 | Wood et al. ............ 366/170.3 |
| 7,887,698 B2* | 2/2011 | Wood ............ 210/199 |
| 7,919,534 B2* | 4/2011 | Wood et al. ............ 516/10 |
| 8,349,191 B2* | 1/2013 | Wood ............ 210/760 |
| 2001/0003291 A1 | 6/2001 | Uematsu |
| 2001/0022755 A1 | 9/2001 | Holtzapple |
| 2001/0031740 A1 | 10/2001 | Unger |
| 2002/0045742 A1 | 4/2002 | Jones |
| 2002/0136662 A1 | 9/2002 | Myrick |
| 2002/0138034 A1 | 9/2002 | Derek |
| 2002/0164379 A1 | 11/2002 | Nishihara |
| 2002/0184820 A1 | 12/2002 | Mauney |
| 2002/0187203 A1 | 12/2002 | Cioca |
| 2003/0017001 A1 | 1/2003 | Ogi |
| 2003/0022288 A1 | 1/2003 | Zuker |
| 2003/0042174 A1 | 3/2003 | Austin |
| 2003/0057163 A1* | 3/2003 | Wood ............ 210/749 |
| 2003/0072212 A1* | 4/2003 | Wood et al. ............ 366/170.3 |
| 2003/0083610 A1 | 5/2003 | McGrath |
| 2003/0188740 A1 | 10/2003 | Tribelsky |
| 2003/0199089 A1 | 10/2003 | Surber |
| 2003/0232114 A1 | 12/2003 | Dekleva |
| 2004/0004042 A1 | 1/2004 | Hadley |
| 2004/0019319 A1 | 1/2004 | Derek |
| 2004/0089746 A1* | 5/2004 | Archambeau et al. ...... 239/533.3 |
| 2004/0090862 A1 | 5/2004 | Uesugi |
| 2004/0118701 A1 | 6/2004 | Senkiw |
| 2004/0126468 A1 | 7/2004 | Holloway |
| 2004/0129112 A1 | 7/2004 | Gillis |
| 2004/0142377 A1 | 7/2004 | Unett |
| 2004/0166171 A1 | 8/2004 | McGrath et al. |
| 2004/0222106 A1 | 11/2004 | Hough |
| 2004/0235732 A1 | 11/2004 | Zhou |
| 2004/0241154 A1 | 12/2004 | Davis |
| 2004/0245186 A1* | 12/2004 | Wood ............ 210/749 |
| 2004/0248909 A1 | 12/2004 | Sun |
| 2004/0258687 A1 | 12/2004 | Waldman |
| 2004/0266693 A1 | 12/2004 | Rubin |
| 2005/0047270 A1* | 3/2005 | Wood et al. ............ 366/170.3 |
| 2005/0048034 A1 | 3/2005 | Fraser |
| 2005/0096458 A1 | 5/2005 | Dumas Milne Edwards |
| 2005/0139808 A1 | 6/2005 | Alimi |
| 2005/0142157 A1 | 6/2005 | Alimi |
| 2005/0196370 A1 | 9/2005 | Yu |
| 2005/0196462 A1 | 9/2005 | Alimi |
| 2005/0249712 A1 | 11/2005 | Leonard |
| 2005/0259510 A1* | 11/2005 | Thoma ............ 366/168.1 |
| 2005/0263607 A1* | 12/2005 | Thoma ............ 237/12 |
| 2005/0273018 A1 | 12/2005 | Don |
| 2006/0030900 A1 | 2/2006 | Eckert |
| 2006/0039902 A1 | 2/2006 | Young |
| 2006/0039910 A1 | 2/2006 | Comeau |
| 2006/0045796 A1 | 3/2006 | Anderle |
| 2006/0054205 A1 | 3/2006 | Yabe |
| 2006/0098528 A1* | 5/2006 | Wood ............ 366/170.3 |
| 2006/0135585 A1 | 6/2006 | Day |
| 2006/0146644 A1 | 7/2006 | Holloway |
| 2006/0150491 A1 | 7/2006 | Senkiw |
| 2006/0198901 A9 | 9/2006 | Holloway, Jr. |
| 2006/0204458 A1 | 9/2006 | Holloway |
| 2006/0216360 A1 | 9/2006 | Upadhyay |
| 2006/0235350 A1 | 10/2006 | Alimi |
| 2006/0241546 A1 | 10/2006 | Alimi |
| 2006/0253060 A1 | 11/2006 | Alimi |
| 2006/0272947 A1 | 12/2006 | Bagley |
| 2006/0272954 A1 | 12/2006 | Sumita |
| 2006/0273018 A1 | 12/2006 | Bagley |
| 2006/0273021 A1 | 12/2006 | Bagley |
| 2006/0273029 A1 | 12/2006 | Bagley |
| 2006/0273281 A1 | 12/2006 | Bagley |
| 2006/0273282 A1 | 12/2006 | Bagley |
| 2006/0273475 A1 | 12/2006 | Bagley |
| 2006/0275423 A1 | 12/2006 | Bagley |
| 2006/0292240 A1 | 12/2006 | Bagley |
| 2006/0292241 A1 | 12/2006 | Bagley |
| 2007/0003497 A1 | 1/2007 | Holloway |
| 2007/0021331 A1 | 1/2007 | Fraser |
| 2007/0077553 A1 | 4/2007 | Bentwich |
| 2007/0141163 A1 | 6/2007 | Vitaliano |
| 2007/0173460 A1 | 7/2007 | Alimi |
| 2007/0173755 A1 | 7/2007 | Alimi |
| 2007/0189972 A1 | 8/2007 | Chiba |
| 2007/0196357 A1 | 8/2007 | Alimi |
| 2007/0196434 A1 | 8/2007 | Alimi |
| 2007/0205161 A1 | 9/2007 | Chiba |
| 2007/0210180 A1* | 9/2007 | Archambeau et al. ............ 239/8 |
| 2007/0237787 A1 | 10/2007 | Leonard |
| 2007/0286795 A1 | 12/2007 | Chiba |
| 2007/0287917 A1 | 12/2007 | Takahashi |
| 2008/0050452 A1 | 2/2008 | Chen |
| 2008/0057486 A1 | 3/2008 | Mano |
| 2008/0063720 A1 | 3/2008 | Gounko |
| 2008/0139674 A1* | 6/2008 | Archambeau et al. ......... 514/789 |
| 2008/0146679 A1* | 6/2008 | Archambeau et al. ......... 514/789 |
| 2008/0153795 A1 | 6/2008 | Occleston |
| 2008/0219088 A1* | 9/2008 | Wood et al. ............ 366/170.1 |
| 2008/0220089 A1 | 9/2008 | Hojo |
| 2009/0082264 A1 | 3/2009 | Fischer |
| 2009/0227459 A1* | 9/2009 | Watson et al. ............ 435/366 |
| 2009/0247458 A1* | 10/2009 | Watson et al. ............ 514/12 |
| 2009/0263495 A1* | 10/2009 | Watson et al. ............ 424/600 |
| 2009/0274730 A1* | 11/2009 | Watson et al. ............ 424/400 |
| 2009/0274771 A1* | 11/2009 | Watson et al. ............ 424/600 |
| 2010/0003333 A1* | 1/2010 | Watson et al. ............ 424/489 |
| 2010/0004189 A1* | 1/2010 | Watson et al. ............ 514/29 |
| 2010/0008997 A1* | 1/2010 | Watson et al. ............ 424/489 |
| 2010/0009008 A1* | 1/2010 | Watson et al. ............ 424/600 |
| 2010/0015235 A1* | 1/2010 | Watson et al. ............ 424/489 |
| 2010/0021464 A1* | 1/2010 | Archambeau et al. ...... 424/139.1 |
| 2010/0028441 A1* | 2/2010 | Watson et al. ............ 424/489 |
| 2010/0028442 A1* | 2/2010 | Archambeau et al. ......... 424/489 |
| 2010/0028443 A1* | 2/2010 | Watson et al. ............ 424/489 |
| 2010/0029764 A1* | 2/2010 | Watson et al. ............ 514/546 |
| 2010/0038244 A1* | 2/2010 | Wood et al. ............ 204/468 |
| 2010/0098659 A1 | 4/2010 | Watson |
| 2010/0098687 A1 | 4/2010 | Watson |
| 2010/0186680 A1 | 7/2010 | Matsumura et al. |
| 2010/0252492 A1* | 10/2010 | Wood ............ 210/205 |
| 2010/0297193 A1* | 11/2010 | Archambeau et al. ......... 424/400 |
| 2010/0303871 A1* | 12/2010 | Watson et al. ............ 424/400 |
| 2010/0303917 A1* | 12/2010 | Watson et al. ............ 424/489 |
| 2010/0303918 A1* | 12/2010 | Watson et al. ............ 424/489 |
| 2010/0310609 A1 | 12/2010 | Watson |
| 2010/0310664 A1* | 12/2010 | Watson et al. ............ 424/489 |
| 2010/0310665 A1* | 12/2010 | Watson et al. ............ 424/489 |

| | | | |
|---|---|---|---|
| 2010/0311167 A1* | 12/2010 | Wood et al. ............... | 435/375 |
| 2010/0316723 A1* | 12/2010 | Watson et al. ............. | 424/489 |
| 2011/0008462 A1* | 1/2011 | Wood et al. ............... | 424/613 |
| 2011/0075507 A1* | 3/2011 | Wootan et al. ............. | 366/124 |
| 2011/0081384 A1* | 4/2011 | Archambeau et al. ...... | 424/400 |
| 2011/0104804 A1* | 5/2011 | Wood et al. ............... | 435/404 |
| 2012/0015083 A1 | 1/2012 | Wood | |
| 2012/0034696 A1 | 2/2012 | Wood | |
| 2012/0039884 A1 | 2/2012 | Watson | |
| 2012/0039951 A1 | 2/2012 | Watson | |
| 2012/0039958 A1 | 2/2012 | Watson | |
| 2012/0114702 A1* | 5/2012 | Watson et al. ............. | 424/600 |

FOREIGN PATENT DOCUMENTS

| | | |
|---|---|---|
| DE | 3436049 | 4/1986 |
| DE | 4317078 | 11/1994 |
| DE | 10105118 | 8/2002 |
| DE | 10227818 | 8/2004 |
| EP | 0363009 | 4/1990 |
| EP | 0555498 | 8/1993 |
| EP | 0682000 | 11/1995 |
| EP | 0880993 | 12/1998 |
| EP | 1201296 | 10/2001 |
| EP | 1797869 | 6/2007 |
| GB | 1279736 | 6/1972 |
| JP | 53-146264 | 12/1978 |
| JP | 56-161893 | 12/1981 |
| JP | 01-171627 | 7/1989 |
| JP | 01171627 A * | 7/1989 |
| JP | 03-169332 | 7/1991 |
| JP | 03169332 A * | 7/1991 |
| JP | 04-290531 | 10/1992 |
| JP | 04290531 A * | 10/1992 |
| JP | 50-96470 | 4/1993 |
| JP | 06-114254 | 4/1994 |
| JP | 06114254 A * | 4/1994 |
| JP | 06-262050 | 9/1994 |
| JP | 06262050 A * | 9/1994 |
| JP | 07-327547 | 12/1995 |
| JP | 08-198969 | 8/1996 |
| JP | 09-122465 | 5/1997 |
| JP | 2003-144887 | 5/2003 |
| JP | 2003-520820 | 7/2003 |
| JP | 2003 340938 | 9/2003 |
| JP | 2004 074131 | 3/2004 |
| JP | 2005 110552 | 4/2005 |
| JP | 2005-523147 | 8/2005 |
| JP | 2005 245817 | 9/2005 |
| JP | 2005 246293 | 9/2005 |
| JP | 2005 246294 | 9/2005 |
| JP | 2006 223239 | 8/2006 |
| JP | 2006-273730 | 10/2006 |
| JP | 2007 275089 | 10/2007 |
| JP | 2008 063258 | 3/2008 |
| JP | 2008 093611 | 4/2008 |
| JP | 2008 093612 | 4/2008 |
| JP | 2008 237950 | 10/2008 |
| JP | 2008 259456 | 10/2008 |
| JP | 2009 039600 | 2/2009 |
| RU | 2091151 | 9/1997 |
| RU | 2131761 | 6/1999 |
| RU | 2165787 | 4/2001 |
| RU | 2166987 | 5/2001 |
| RU | 2284853 | 4/2005 |
| SU | 127999 | 1/1960 |
| SU | 162461 | 12/1961 |
| SU | 280441 | 11/1970 |
| SU | 495099 | 3/1976 |
| SU | 495862 | 12/1976 |
| SU | 889078 | 12/1981 |
| SU | 921611 | 4/1982 |
| SU | 1281290 | 1/1987 |
| SU | 1337098 | 9/1987 |
| SU | 1584990 | 8/1990 |
| SU | 1706683 | 1/1992 |
| SU | 1768269 | 10/1992 |
| SU | 1773469 | 11/1992 |
| SU | 1820861 | 6/1993 |
| WO | WO 92/05792 | 4/1992 |
| WO | WO 95/35501 | 12/1995 |
| WO | WO 98/30319 | 7/1998 |
| WO | WO 00/02651 | 1/2000 |
| WO | WO 00/20109 | 4/2000 |
| WO | WO 01/54704 | 8/2001 |
| WO | WO 01/87471 | 11/2001 |
| WO | WO 02/24222 | 3/2002 |
| WO | WO 02/35234 | 5/2002 |
| WO | WO 02/38510 | 5/2002 |
| WO | WO 02/060458 | 8/2002 |
| WO | WO 02/062455 | 8/2002 |
| WO | WO 03/044430 | 5/2003 |
| WO | WO 03/089123 | 10/2003 |
| WO | WO 2004/013049 | 2/2004 |
| WO | WO 2004/016344 | 2/2004 |
| WO | WO 2004/022098 | 3/2004 |
| WO | WO 2004/112649 | 12/2004 |
| WO | WO 2005/030649 | 4/2005 |
| WO | WO 2005/032243 | 4/2005 |
| WO | WO 2005/084718 | 9/2005 |
| WO | WO 2005/084786 | 9/2005 |
| WO | WO 2005/085141 | 9/2005 |
| WO | WO 2005/113026 | 12/2005 |
| WO | WO 2006/029385 | 3/2006 |
| WO | WO 2006/088210 | 8/2006 |
| WO | WO 2006/133113 | 12/2006 |
| WO | WO 2007/096149 | 8/2007 |
| WO | WO 2008/018932 | 2/2008 |
| WO | WO 2008/052143 | 5/2008 |
| WO | WO 2008/115290 | 9/2008 |
| WO | WO 2009/055614 | 4/2009 |
| WO | WO 2009/055620 | 4/2009 |
| WO | WO 2009/055729 | 4/2009 |
| WO | WO 2009/055824 | 4/2009 |
| WO | WO 2010/048425 | 4/2010 |
| WO | WO 2010/048455 | 4/2010 |

OTHER PUBLICATIONS

Austin, et al., "Xylene monooxygenase, a membrane-spanning non-heme diiron enzyme that hydroxylates hydrocarbons via a substrate radical intermediate," Journal of Inorganic Chemistry, 8:733-740, 2003.

Billington et al., "Signaling and regulation of G protein-coupled receptors in airway smooth muscle," Respiratory Research 4(2):1-23, 2003.

Bonanno, "Corneal Metabolic Activity in Humans: Corneal Oxygen Consumption," Indiana University School of Optometry Faculty Research, retrieved Apr. 9, 2003, from http://www.opt.indiana.edu/people/faculty/bonanno/oxygen.htm (4 pages).

Bragg et al., "Hydrated Electron Dynamics: From Clusters to Bulk," Science Magazine, 360(5696):669-671, Sep. 16, 2004.

Brazeau et al., "Intermediate Q from Soluble Methane Monooxygenase Hydroxylates the Mechanistic Substrate Probe Norcarane: Evidence for a Stepwise Reaction," Journal of the American Chemical Society, 123(481:11831-11837, Dec. 5, 2001.

Bucy et al., "Initial increase in blood CD4+ lymphocytes after HIV antiretroviral therapy reflects redistribution from lymphoid tissues," The Journal of Clinical Investigation 103(10):1391-1398, 1999.

Bunkin et al., "Existence of charged submicrobubble clusters in polar liquids as revealed by correlation between optical cavitation and electrical conductivity," Colloids and Surfaces A: Physicochemical and Engineering Aspects, 1996, pp. 207-212, vol. 110.

Campbell et al., "Redox Modulation of L-Type Calcium Channels in Feret Ventricular Myocytes," Journal of General Physiology, 1996, pp. 277-293, vol. 108.

Chaplin, "Declustered Water, Anomalous Water and Crystals," retrieved Jul. 10, 2006, from http://Isbu.ac.uk/water/anmlous.html (4 pages).

Compilation of: (1) Abstract of Wunderlich et al., "In vivo observation of oxygen-supersaturated water in the human mouth and stomach," Magnetic Resonance Imaging, 22(4):551-556, 2004; (2) Abstract of Divino et al., "Injection of highly supersaturated oxygen solutions without nucleation," Journal of Biomechanical Engineering, 124(6):676-683, 2002; (3) Product Information from O2Canada Water, Inc.; (4) Production Information from FBC Technologies, "O2x-Box® Super Oxygenation Process"; and (5) Wayne State Univierisity Press Release entitled "Researcher Discovers Potential Approach to Hyperoxygenate Blood," Apr. 4, 2006 (4 pages).
De Angelis et al., "Electronic Structure and Reactivity of Isomeric Oxo-Mn(V) Porphyrins: Effects of Spin-State Crossing and pKa Modulation," Inorganic Chemistry, 45(10):4268-4276, Feb. 22, 2006.
Faul, "Sonochemistry—General Overview," retrieved Nov. 21, 2002, from http://www.und.ac.za/prg/sonochem/ultragen.html (2 pages).
Florusse et al., "Stable Low-Pressure Hydrogen Clusters Stored in a Binary Clathrate Hydrate," Science Magazine, 306:469-471, Oct. 15, 2004.
Frauenfelder et al., "The role of structure, energy landscape, dynamics, and allostery in the enzymatic function of myoglobin," Proceedings of the National Academy of Sciences, 98(5):2370-2374, Feb. 27, 2001.
Gill et al., "Nanoparticles: Characteristics, Mechanisms of Action, and Toxicity in Pulmonary Drug Delivery—a Review." Journal of biomedical Nanotechnology, 3(2):107-119, 2007.
Groves, "High-valent iron in chemical and biological oxidations," Journal of Inorganic Biochemistry, 100:434-447, Jan. 14, 2006.
Groves, "Reactivity and mechanisms of metalloporphyrin-catalyzed oxidations," Journal of Porphyrins and Phthalocyanines, 4:350-352, 2002.
Hammer et al., "How Do Small Water Clusters Bind an Excess Electron," Science Magazine, 306(5696):675-679, Sep. 16, 2004.
Harvitt, "Corneal Oxygen Availability and Metabolism with Contact Lens Wear" and Harvitt et al., "Re-evaluation of the Oxygen Diffision Model for Predicting Minimum Contact Lens Dk/t Values Needed to Avoid Corneal Anoxia," retrieved Apr. 9, 2003, from http://vision.berkeley.edu/sarver/mdsl_harvitt_research.html (abstracts only) (2 pages).
Headrick et al., "Spectral Signatures of Hydrated Proton Vibrations in Water Clusters," Science Magazine, 308:1765-1770, Jun. 17, 2005.
Hogaboam, C.M. et al., "Collagen Deposition in a Non-Fibrotic Lung Granuloma Model after Nitric Oxide Inhibition," Am. J. Pathol., 153(6): 1861-1872, 1998.
Jia et al., "Atomic-Resolution Measurement of Oxygen Concentration in Oxide Materials," Science Magazine, 303:2001-2004, Mar. 26, 2004.
Jin et al., "Unusual Kinetic Stability of a Ground-State Singlet Oxomanganese(V) Porphyrin. Evidence for a Spin State Crossing Effect," Journal of the American Chemical Society, 121:2923-2924, 1999.
Life 02 International (Asia) Co., Ltd., retrieved Jun. 3, 2003, from www.lifeo2asia.com/medical.html (1 page).
Lowenstein et al., "Nitric Oxide: A Physiologic Messenger," Annals of Internal Medicine, 1994, pp. 227-237, vol. 120.
Lower, "The BunkHouse: Water pseudoscience gallery, Gallery of water-related pseudoscience, Junk science in the marketplace," retrieved Jul. 25, 2006, from http:// chem1.com/CO/gallery.html (18 pages).
Luo et al., "Mycobactin-mediated iron acquisition within macrophages," Nature Chemical Biology, 1(3):149-153, Aug. 2005.
Miyazaki et al., "Infrared Spectroscopic Evidence for Protonated Water Clusters Forming Nanoscale Cages," Science Magazine, 304:1134-1137, Apr. 29, 2004.
Moe et al., "Remarkable Aliphatic Hydroxylation by the Diiron Enzyme Toluene 4-Monooxygenase in reactions with Radical or Cation Diagnostic Probes Norcarane, 1,1-Dimethylcyclopropane, and 1,1-Diethylcyclopropane," American Chemical Society, 43:15688-15701, Jul. 1, 2004.
Morris, "The physiological causes of contact lens complications," Optometry Today, :pp. 28-33, Dec. 3, 1999.
Murga et al., "Activation of Akt/Protein Kinase B by G-protein," Jul. 24, 1998, The Journal of Biological Chemistry, vol. 273, No. 30, pp. 19080-19085.
Nguyen et al., "Neuroprotection by NGF and BDNF Against Neurotoxin-Exerted Apoptotic Death in Neural Stem Cells are Mediated through Trk Receptors, Activating P13-Kinase and MAPK Pathways," Neurochemical Research 2009, pp. 942,951, vol. 34.

Nozaki et al., "New Enhancers for the Chemiluminescent Peroxidase Catalysed Chemiluminescent Oxidation of Pyrogallol and Purpurogallin," Journal of Bioluminescence Chemiluminescence, 1995, pp. 151-156, vol. 10.
Ohgaki et al., "Physicochemical approach to nanobubble solutions," Chemical Engineering Science, 2010, pp. 1296-1300, vol. 65.
Paik et al., "Electrons in Finite-Sized Water Cavities: Hydration Dynamics Observed in Real Time," Science Express, 306(5696):672-675, Sep. 16, 2004.
Pan et al., "Role of the Rho GTPas in Bradykinin-Stimulated Nuclear Factor-kB Activation and IL-1β Gene Expression in Cultured Human Epithelial Cells," J. Immunol., 1998, 160: 3038-3045, The Scripps Research Institute, La Jolla.
Park et al., "Nitric oxide regulates nitric oxide synthase-2 gene expression by inhibiting NF-KB binding to DNA," The Biochemical Journal, 1997, pp. 609-613, vol. 322.
Patent Office of the Russian Federation, "Official Action," Application No. 2004133560/15(036500), Jan. 27, 2006, original in Russian plus English translation (6 pages).
"Protonated Water Clusters in Interstellar Clouds, the Upper Atmosphere and Biomolecules," retrieved Oct. 29, 2004, from http:// pro3.chem.pitt.edu/richard/prot_clust_nature.html (1 page).
Rutgeerts et al., "Review Article: the limitations of corticosteroid therapy in Crohn's disease," Alimentary Pharmacology & Therapeutics, 2001, pp. 1515-1525, vol. 15.
Salzman et al., "Nitrix oxide dilates tight junctions and depletes ATP in cultured Caco-2BB3 intestinal epithelial monolayers," American Journal of Physiology, Gastrointestinal and Livery Physiology, 1995, pp. G361-G373, vol. 268 (abstract only).
Schmidt et al., "A role for Rho in receptor- and G protein-stimulated phospholipase C. Reduction in phosphatidylinositol 4,5-bisophosphate by Clostridium difficile toxin B," Naunyn Schmiedebergs Arch Pharmacol. 354(2):87-94, Jul. 1996 (abstract only).
Science Week (1) "Chemistry: On Protonated Water Clusters" (points made by Zwier [Science 2004 204:1119]); "On Water Structure" (points made by Head-Gordon et al. [Chem. Rev. 2002 102:2651]); "Liquid Water: Current Research Problems" (points made by Keutsch et al. [Proc. Nat. Acad. Sci. 2001 98:10533]) (5 pages).
Shin et al., "Infrared Signature of Structures Associated with the H+(H2O)n (n = 6 to 27) Clusters," Science Magazine, 304:1137-1140, May 21, 2004.
Tristani-Firouzi M., H.L. Reeve, S. Tolarova, E.K. Weir, and S.L. Archer. Oxygen-induced constriction of rabbit ductus arteriosus via inhibition of a 4-aminopyridine-, voltage-sensitive potassium channel. J. Clin. Invest. 98:1959-1965, 1996.
Wang, "Radical Clocks: Molecular Stopwatches for timing Radical Reactions," pp. 65-72, Apr. 27, 2006.
Wojciak-Stothard et al., "Rac and Rho play opposing roles in the regulation of hypoxia/reoxygenation-induced permeability changes in pulmonary artery endothelial cells," Am. J. of Lung Cell Mol. Physiol 288:L749-L760, 2005.
Wronski et al., "Interfacial area in a reactor with helicoidal flow for the two-phase gas-liquid system," Chemical Engineering Journal, 2005, pp. 71-79, vol. 105.
Zwier, "The Structure of Protonated Water Clusters," Science Magazine, 304 (5674):1119-1120, Apr. 29, 2004.
Gomes et al., "Calcium Channel Blocker Prevents T Helper Type 2 Cell-mediated Airway Inflammation," Am J Respir Crit Care Med.; 175:1117-1124, 2007.
Guerra et al. "The effect of oxygen free radicals on calcium current and dihydropyridine binding sites in guinea-pig ventricular myocytes," British Journal of Pharmacology, 1996, pp. 1278-1284, vol. 118, Institute of Pharmacology, University of Ferrara and *Department of Pharmacology, University of Firenze, Italy.
Stoll et al., "Inflammation and atherosclerosis: novel insights into plaque formation and destabilization," Stroke, Jul. 2006, 37(7):pp. 1923-1932.

* cited by examiner

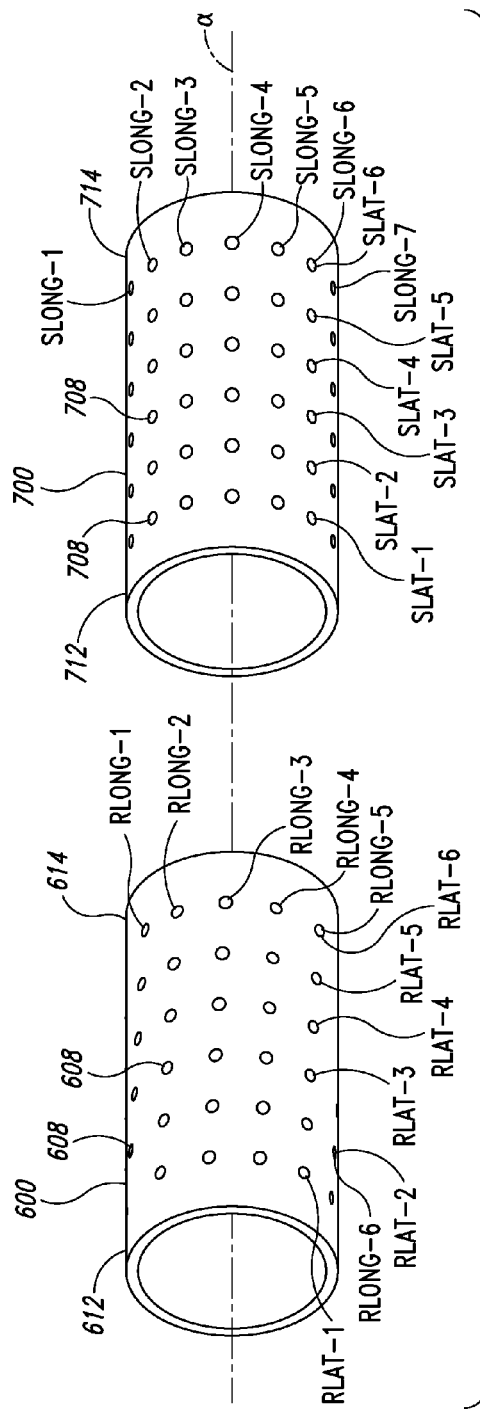
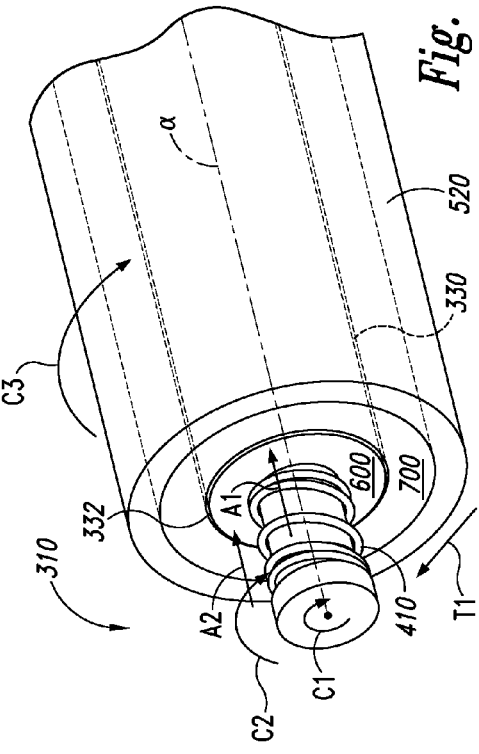
Fig. 8
Fig. 9

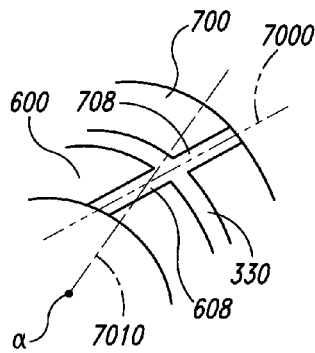
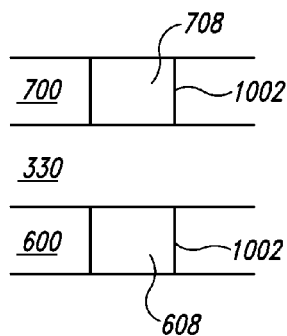
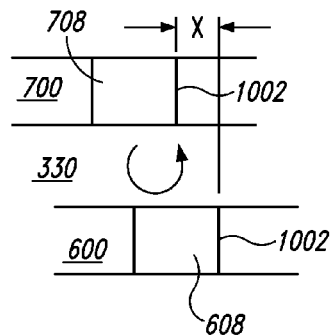
*Fig. 19*     *Fig. 20*     *Fig. 21*
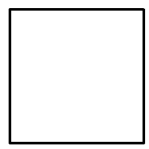
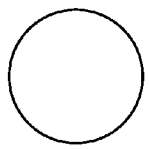
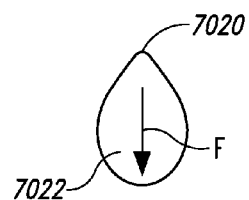
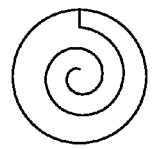
*Fig. 22*     *Fig. 23*     *Fig. 24*     *Fig. 25*
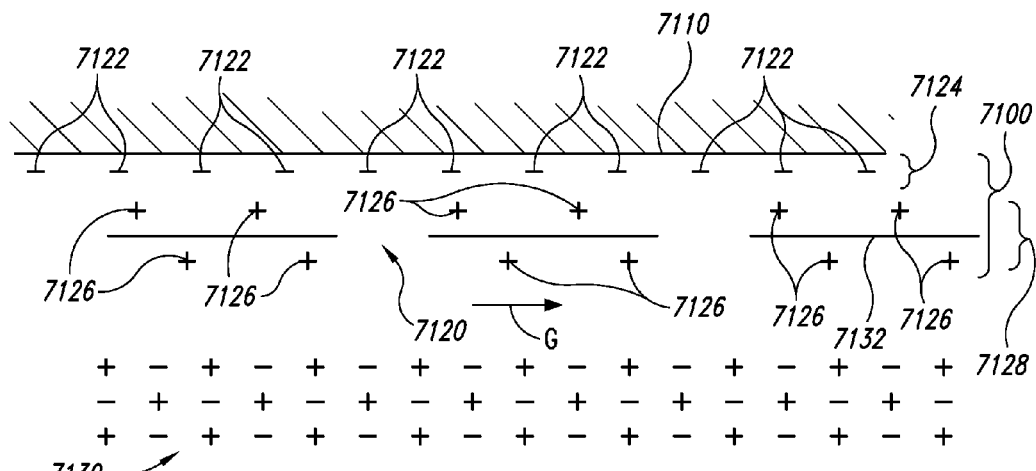
*Fig. 26*

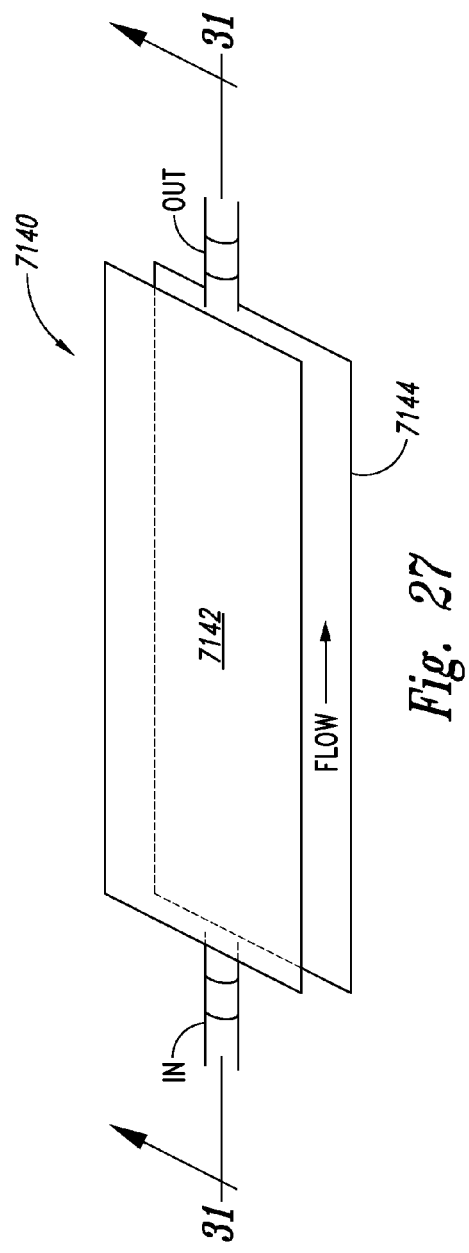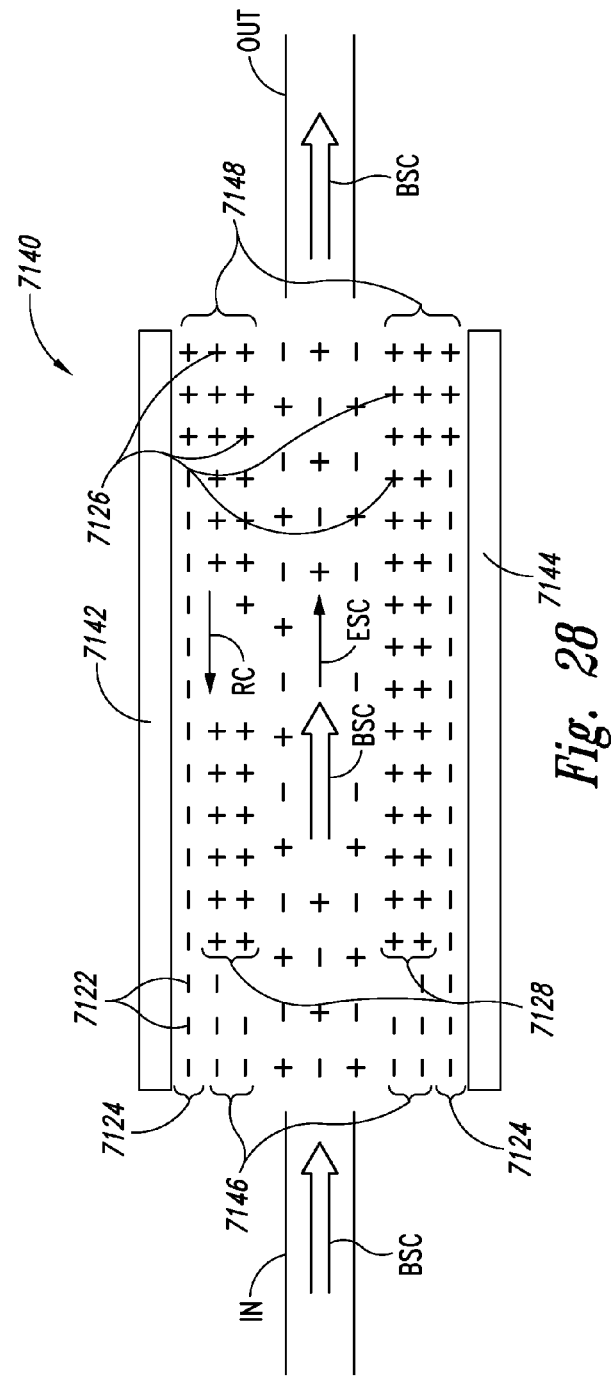

MIXING DEVICE FOR CREATING AN OUTPUT MIXTURE BY MIXING A FIRST MATERIAL AND A SECOND MATERIAL

CROSS REFERENCE TO RELATED APPLICATION(S)

This application is a continuation of U.S. patent application Ser. No. 11/924,589, filed Oct. 25, 2007 of same title (now issued as U.S. Pat. No. 7,832,920), which claims the benefit of priority to U.S. Provisional Application Nos. 60/862,904, filed Oct. 25, 2006, 60/862,955, filed Oct. 25, 2006, and 60/982,38, filed Oct. 24, 2007.

BACKGROUND OF THE INVENTION

1. Field of the Invention

The present invention is directed generally to mixing devices and more particularly to mixing devices that mix two or more materials between surfaces, including such as between a rotating rotor and a stationary stator.

2. Description of the Related Art

FIG. 1 provides a partial block diagram, partial cross-sectional view of a prior art device 10 for diffusing or emulsifying one or two gaseous or liquid materials ("infusion materials") into another gaseous or liquid material ("host material") reproduced from U.S. Pat. No. 6,386,751, incorporated herein by reference in its entirety. The device 10 includes a housing configured to house a stator 30 and a rotor 12. The stator 30 encompasses the rotor 12. A tubular channel 32 is defined between the rotor 12 and the stator 30. The generally cylindrically shaped rotor 12 has a diameter of about 7.500 inches and a length of about 6.000 inches providing a length to diameter ratio of about 0.8.

The rotor 12 includes a hollow cylinder, generally closed at both ends. A gap exists between each of the first and second ends of the rotor 12 and a portion of the housing 34. A rotating shaft 14 driven by a motor 18 is coupled to the second end of the rotor 12. The first end of the rotor 12 is coupled to an inlet 16. A first infusion material passes through the inlet 16 and into the interior of the rotor 12. The first infusion material passes from the interior of the rotor 12 and into the channel 32 through a plurality of openings 22 formed in the rotor 12.

The stator 30 also has openings 22 formed about its circumference. An inlet 36 passes a second infusion material to an area 35 between the stator 30 and the housing 34. The second infusion material passes out of the area 35 and into the channel 32 through openings 22.

An external pump (not shown) is used to pump the host material into a single inlet port 37. The host material passes through a single inlet port 37 and into the channel 32 where it encounters the first and second infusion materials, which enter the channel 32 through openings 22. The infusion materials may be pressurized at their source to prevent the host material from passing through openings 22.

The inlet port 37, is configured and positioned such that it is located along only a relatively small portion (<about 5%) of the annular inlet channel 32, and is substantially parallel to the axis of rotation of the rotor 12 to impart an axial flow toward a portion of the channel 32 into the host material.

Unfortunately, before entering the tubular channel 32, the host material must travel in tortuous directions other than that of the axial flow (e.g., including in directions substantially orthogonal thereto) and down into and between the gap formed between the first end of the rotor 12 and the housing 34 (i.e., down a portion of the first end of the rotor adjacent to the inlet 16 between the end of the rotor 12 and the housing 34). The non-axial and orthogonal flow, and the presence of the host material in the gap between the first end of the rotor 12 and the housing 34 causes undesirable and unnecessary friction. Further, it is possible for a portion of the host material to become trapped in eddy currents swirling between the first end of the rotor and the housing. Additionally, in the device 10, the host material must negotiate at least two right angles to enter any aspect of the annual of the annular inlet of the tubular channel 32.

A single outlet port 40 is formed in the housing 34. The combined host material and infusion material(s) exit the channel 32 via the outlet 40. The outlet port 40, which is also located along only a limited portion (<about 5%) of the annular outlet of tubular channel 32, is substantially parallel to the axis of rotation of the rotor 12 to impart or allow for an axial flow of the combined materials away from the limited portion of the annular outlet of tubular channel 32 into the outlet port 40. An external pump 42 is used to pump the exiting fluid through the outlet port 40.

Unfortunately, before exiting the channel 32, a substantial portion of the exiting material must travel in a tortuous direction other than that of the axial flow (e.g., including in directions substantially orthogonal thereto) and down into and between the gap formed between the second end of the rotor 12 and the housing 34 (i.e., down a portion of the second end of the rotor adjacent to the shaft 14 between the end of the rotor 12 and the housing 34). As mentioned above, the non-axial and orthogonal flow, and the presence of the host material in the other gap between the end (in this case, the second end) of the rotor 12 and the housing 34 causes additional undesirable and unnecessary friction. Further, it is possible for a portion of the host material to become trapped in eddy currents swirling between the second end of the rotor and the housing. Additionally, in the device 10, a substantial portion of the exiting combined material must negotiate at least two right angles as it exits form the annular exit of the tubular channel 32 into the outlet port 40.

As is apparent to those of ordinary skill in the art, the inlet port 37 imparts only an axial flow to the host material. Only the rotor 21 imparts a circumferential flow into the host material. Further, the outlet port 40 imparts or provides for only an axial flow into the exiting material. Additionally, the circumferential flow velocity vector is imparted to the material only after it enters the annular inlet 37 of the tubular channel 32, and subsequently the circumferential flow vector must be degraded or eliminated as the material enters the exit port 40. There is, therefore, a need for a progressive circumferential acceleration of the material as it passes in the axial direction through the channel 32, and a circumferential deceleration upon exit of the material from the channel 32. These aspects, in combination with the tortuous path that the material takes from the inlet port 37 to the outlet port 40, create a substantial friction and flow resistance over the path that is accompanied by a substantial pressure differential (26 psi, at 60 gallons/min flow rate) between the inlet 37 and outlet 40 ports, and these factors, inter alia, combine to reduce the overall efficiency of the system.

BRIEF DESCRIPTION OF THE SEVERAL VIEWS OF THE DRAWING(S)

FIG. 8 is a perspective view of a rotor and a stator of the mixing device of FIG. 2.

FIG. 9 is a perspective view of an inside of a first chamber of the mixing device of FIG. 2.

FIG. 19 is an enlarged fragmentary cross-sectional view taken through a plane orthogonal to an axis of rotation of the rotor depicting an alternate configuration of through-holes formed in the rotor and through-holes formed in the stator.

FIG. 20 is an enlarged fragmentary cross-sectional view taken through a plane passing through and extending along the axis of rotation of the rotor depicting a configuration of through-holes formed in the rotor and through-holes formed in the stator.

FIG. 21 is an enlarged fragmentary cross-sectional view taken through a plane passing through and extending along the axis of rotation of the rotor depicting an alternate offset configuration of through-holes formed in the rotor and through-holes formed in the stator.

FIG. 22 is an illustration of a shape that may be used to construct the through-holes of the rotor and/or the apertures of the stator.

FIG. 23 is an illustration of a shape that may be used to construct the through-holes of the rotor and/or the apertures of the stator.

FIG. 24 is an illustration of a shape that may be used to construct the through-holes of the rotor and/or the apertures of the stator.

FIG. 25 is an illustration of a shape that may be used to construct the through-holes of the rotor and/or the apertures of the stator.

FIG. 26 is an illustration of an electrical double layer ("EDL") formed near a surface.

FIG. 27 is a perspective view of a model of the inside of the mixing chamber.

FIG. 28 is a cross-sectional view of the model of FIG. 27.

FIGS. 45A and 45B illustrate a graphical representation of a exemplary embodiments of a bioreactor system 3300a.

DETAILED DESCRIPTION OF THE INVENTION

Overview

Figure 2:
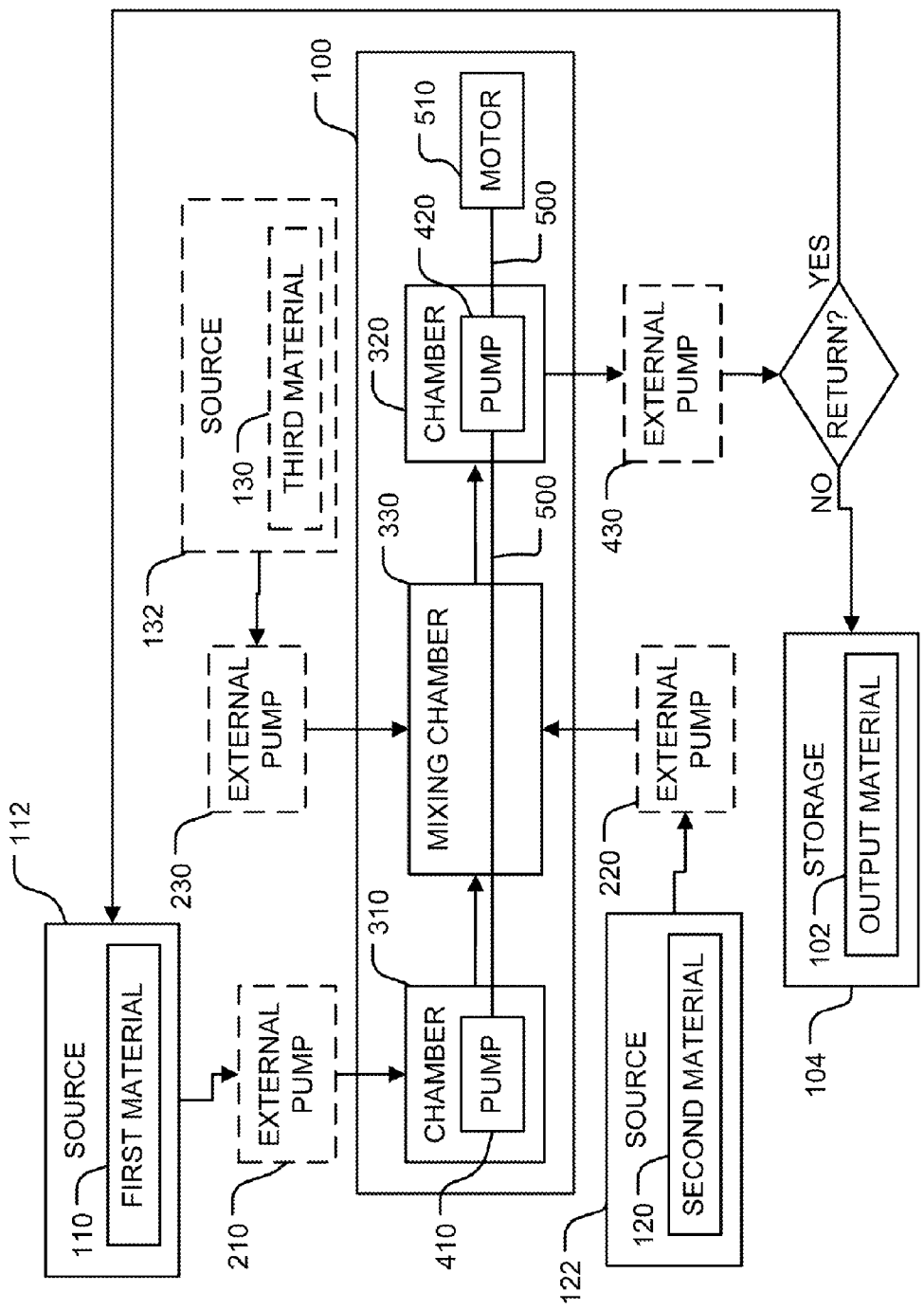
FIG. 2 is block diagram of an exemplary embodiment of a mixing device.

FIG. 2 provides a block diagram illustrating some of the components of a mixing device 100 and the flow of material into, within, and out of the device. The mixing device 100 combines two or more input materials to form an output material 102, which may be received therefrom into a storage vessel 104. The mixing device 100 agitates the two or more input materials in a novel manner to produce an output material 102 having novel characteristics. The output material 102 may include not only a suspension of at least one of the input materials in at least one of the other input materials (e.g., emulsions) but also a novel combination (e.g., electrostatic combinations) of the input materials, a chemical compound resulting from chemical reactions between the input materials, combinations having novel electrostatic characteristics, and combinations thereof.

The input materials may include a first material 110 provided by a source 112 of the first material, a second material 120 provided by a source 122 of the second material, and optionally a third material 130 provided by a source 132 of the third material. The first material 110 may include a liquid, such as water, saline solution, chemical suspensions, polar liquids, non-polar liquids, colloidal suspensions, cell growing media, and the like. In some embodiments, the first material 110 may include the output material 102 cycled back into the mixing device 100. The second material 120 may consist of or include a gas, such as oxygen, nitrogen, carbon dioxide, carbon monoxide, ozone, sulfur gas, nitrous oxide, nitric oxide, argon, helium, bromine, and combinations thereof, and the like. In preferred embodiments, the gas is or comprises oxygen. The optional third material 130 may include either a liquid or a gas. In some embodiments, the third material 130 may be or include the output material 102 cycled back into the mixing device 100 (e.g., to one or more of the pumps 210, 220 or 230, and/or into the chamber 310, and/or 330).

Optionally, the first material 110, the second material 120, and the optional third material 130 may be pumped into the mixing device 100 by an external pump 210, an external pump 220, and an external pump 230, respectively. Alternatively, one or more of the first material 110, the second material 120, and the optional third material 130 may be stored under pressure in the source 112, the source 122, and the source 132, respectively, and may be forced into the mixing device 100 by the pressure. The invention is not limited by the method used to transfer the first material 110, the second material 120, and optionally, the third material 130 into the mixing device 100 from the source 112, the source 122, and the source 132, respectively.

The mixing device 100 includes a first chamber 310 and a second chamber 320 flanking a mixing chamber 330. The three chambers 310, 320, and 330 are interconnected and form a continuous volume.

The first material 110 is transferred into the first chamber 310 and flows therefrom into the mixing chamber 330. The first material 110 in the first chamber 310 may be pumped into the first chamber 310 by an internal pump 410. The second material 120 is transferred into the mixing chamber 330. Optionally, the third material 130 may be transferred into the mixing chamber 330. The materials in the mixing chamber 330 are mixed therein to form the output material 102. Then, the output material 102 flows into the second chamber 320 from which the output material 102 exits the mixing device 100. The output material 102 in the mixing chamber 330 may be pumped into the second chamber 320 by an internal pump 420. Optionally, the output material 102 in the second chamber 320 may be pumped therefrom into the storage vessel 104 by an external pump 430 (e.g., alone or in combination with the internal pump 410 and/or 420).

In particular aspects, a common drive shaft 500 powers both the internal pump 410 and the internal pump 420. The drive shaft 500 passes through the mixing chamber 330 and provides rotational force therein that is used to mix the first material 110, the second material 120, and optionally, the third material 130 together. The drive shaft 500 is powered by a motor 510 coupled thereto.

Figure 3:
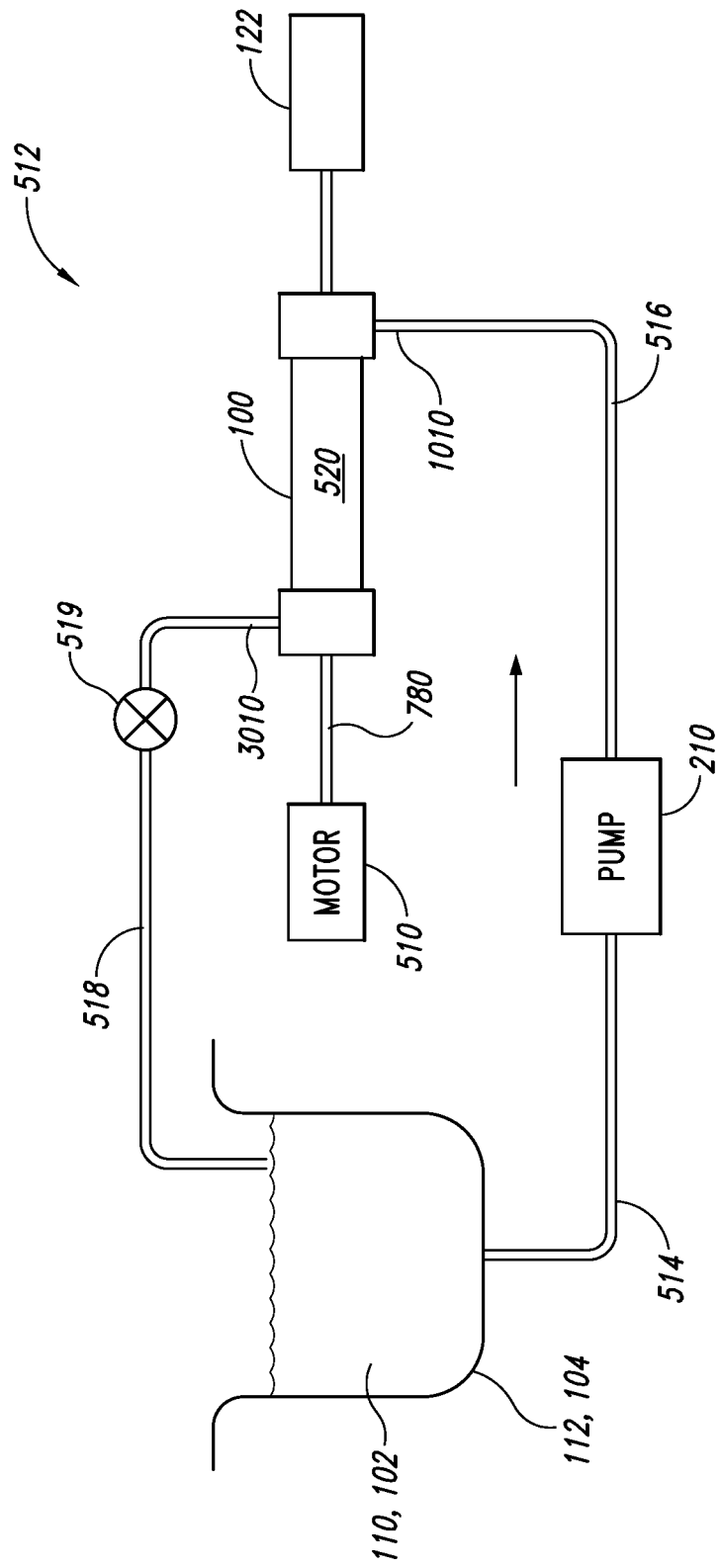
FIG. 3 is an illustration of an exemplary system for delivering a first material to the mixing device of FIG. 2.

FIG. 3 provides a system 512 for supplying the first material 110 to the mixing device 100 and removing the output material 102 from the mixing device 100. In the system 512, the storage vessel 104 of the output material 102 and the source 112 of the first material 110 are combined. The external pump 210 is coupled to the combined storage vessel 104 and source 112 by a fluid conduit 514 such as hose, pipe, and the like. The external pump 210 pumps the combined first material 110 and output material 102 from the combined storage vessel 104 and source 112 through the fluid conduit 514 and into a fluid conduit 516 connecting the external pump 210 to the mixing device 100. The output material 102 exits the mixing device 100 through a fluid conduit 518. The fluid conduit 518 is coupled to the combined storage vessel 104 and source 112 and transports the output material 102 exiting the mixing device 100 to the combined storage vessel 104 and source 112. The fluid conduit 518 includes a valve 519 that establishes an operating pressure or back pressure within the mixing device 100.

Referring to FIGS. 2, 4-10, and 11, a more detailed description of various components of an embodiment of the mixing device 100 will be provided. The mixing device 100 is scalable. Therefore, dimensions provided with respect to various components may be used to construct an embodiment of the device or may be scaled to construct a mixing device of a selected size.

Figure 4:
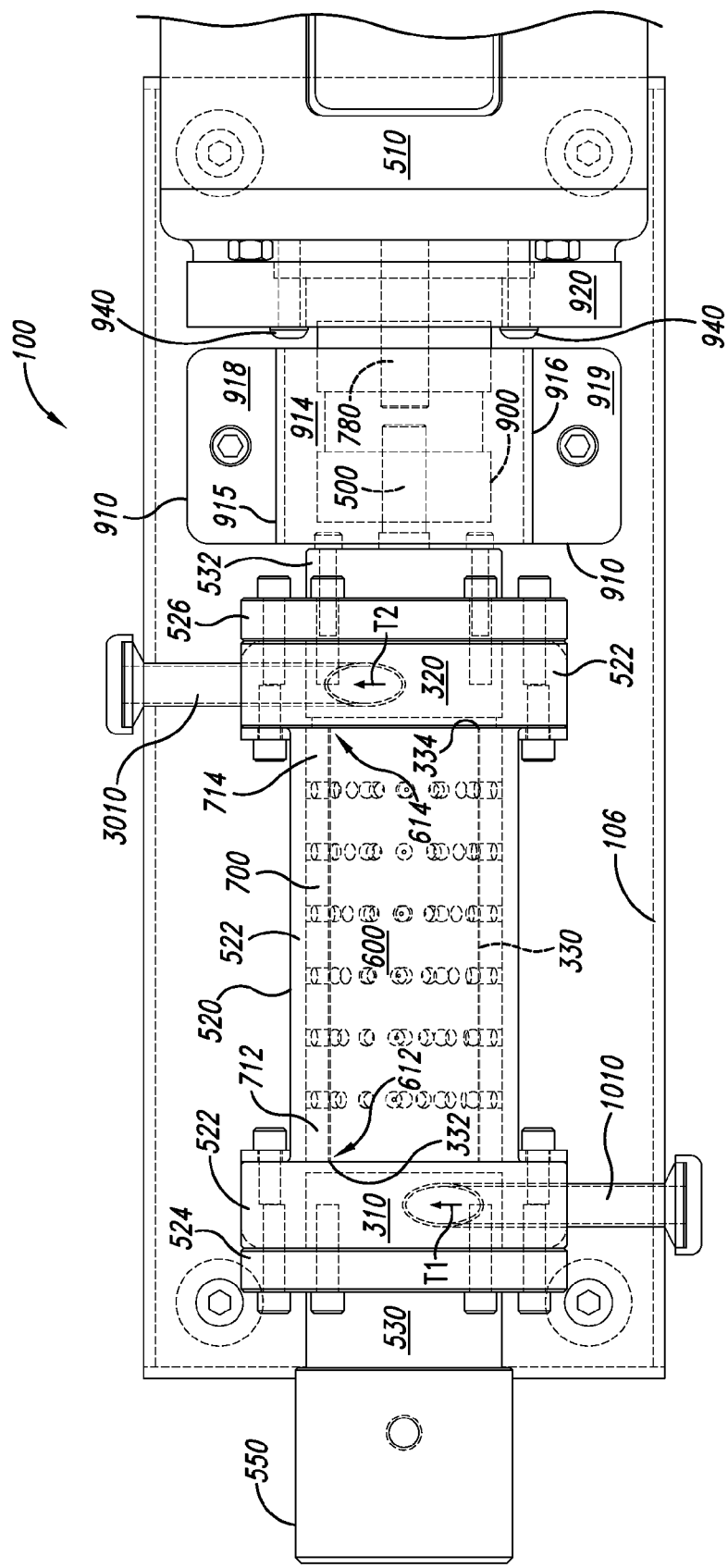
FIG. 4 is a fragmentary partial cross-sectional view of a top portion of the mixing device of FIG. 2.

Turning to FIG. 4, the mixing device 100 includes a housing 520 that houses each of the first chamber 310, the mixing chamber 330, and the second chamber 320. As mentioned above, the mixing device 100 includes the drive shaft 500, which rotates during operation of the device. Therefore, the mixing device 100 may vibrate or otherwise move. Optionally, the mixing device 100 may be coupled to a base 106, which may be affixed to a surface such as the floor to maintain the mixing device 100 in a substantially stationary position.

The housing 520 may be assembled from two or more housing sections. By way of example, the housing 520 may include a central section 522 flanked by a first mechanical seal housing 524 and a second mechanical seal housing 526. A bearing housing 530 may be coupled to the first mechanical seal housing 524 opposite the central section 522. A bearing housing 532 may be coupled to the second mechanical seal housing 526 opposite the central section 522. Optionally, a housing section 550 may be coupled to the bearing housings 530.

Figure 5:
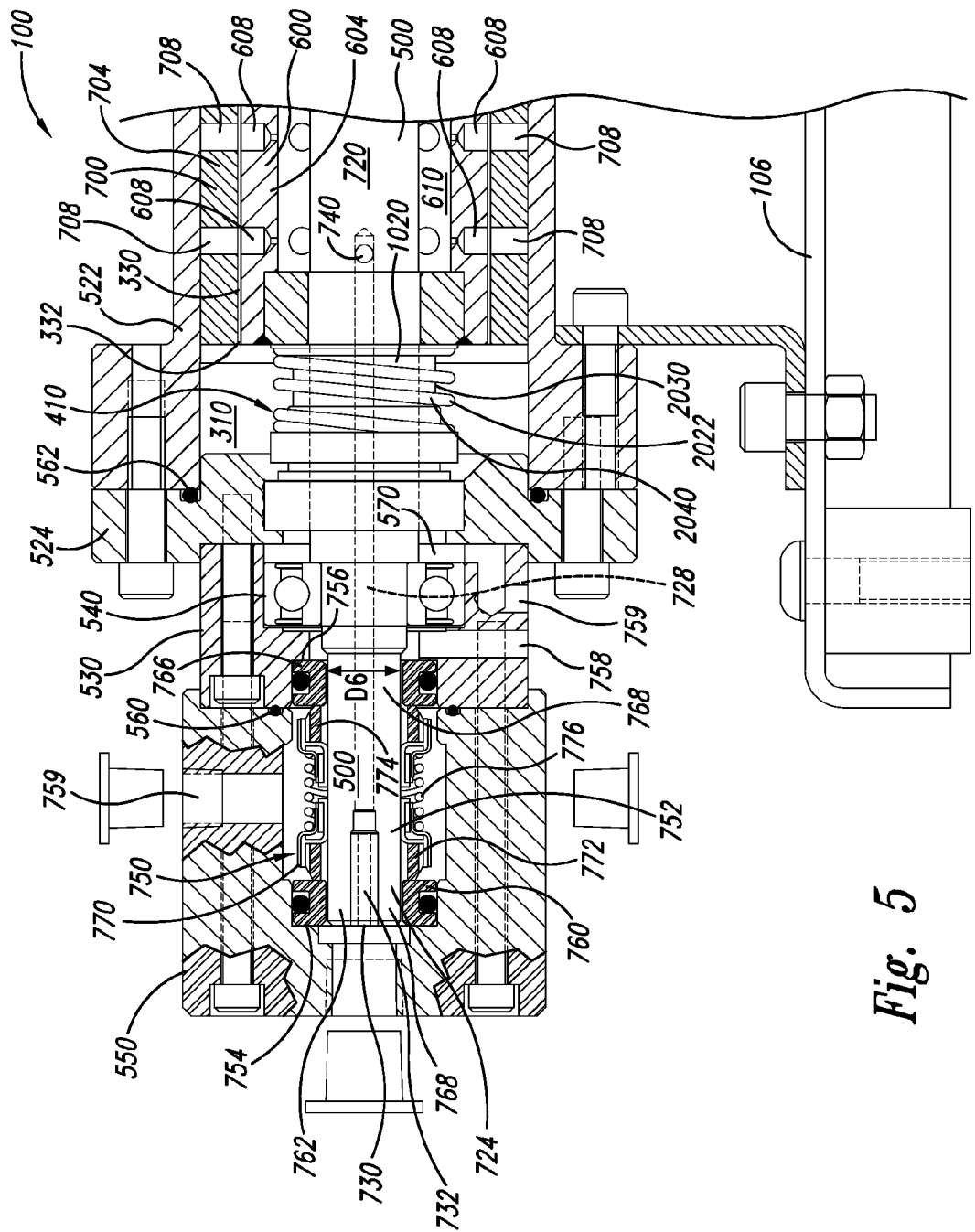
FIG. 5 is a fragmentary cross-sectional view of a first side portion of the mixing device of FIG. 2.
Figure 6:
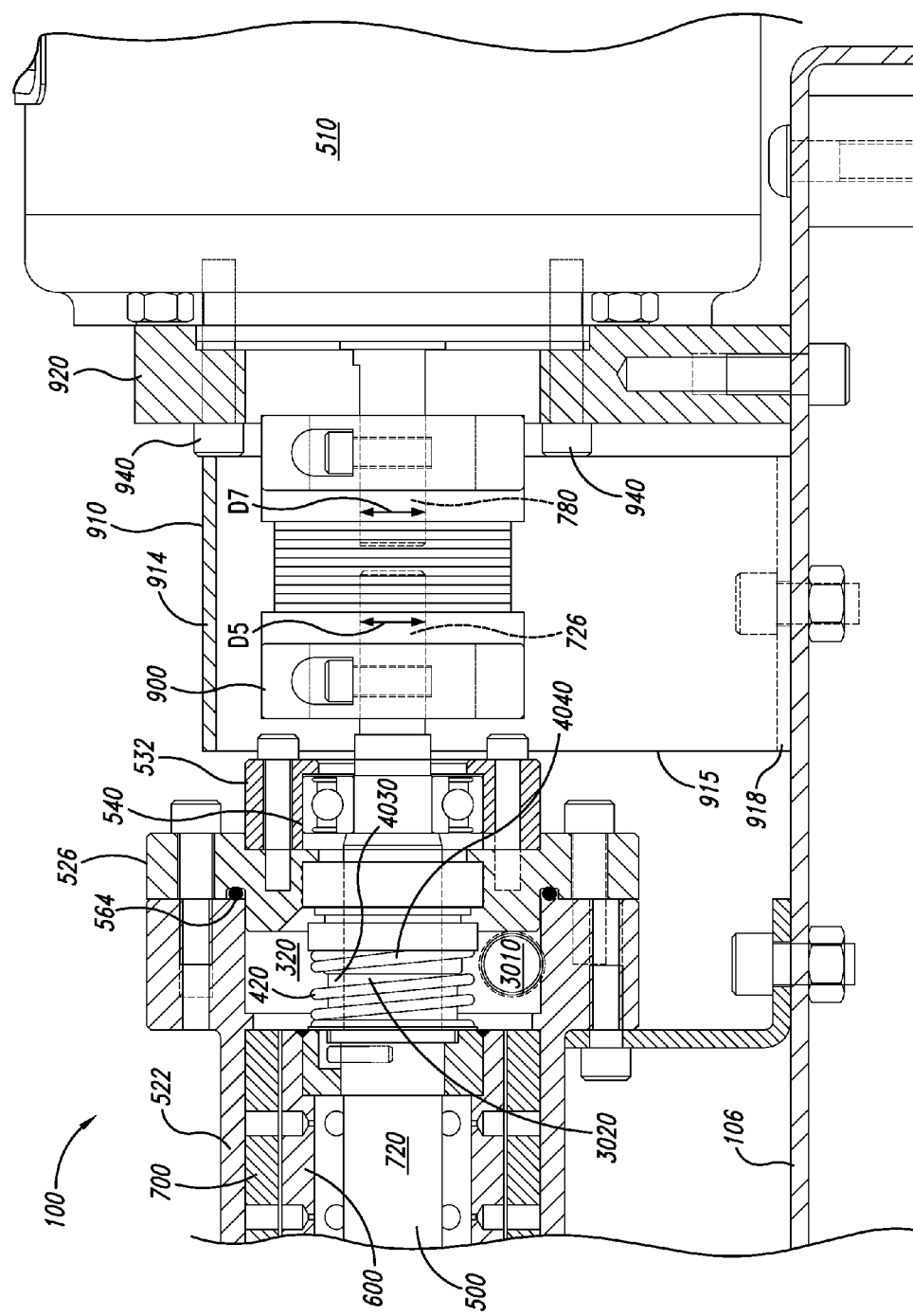
FIG. 6 is a fragmentary cross-sectional view of a second side portion of the mixing device of FIG. 2.

Each of the bearing housings 530 and 532 may house a bearing assembly 540 (see FIGS. 5 and 6). The bearing assembly 540 may include any suitable bearing assembly known in the art including a model number "202SZZST" manufactured by SKF USA Inc, of Kulpsville, Pa., operating a website at www.skf.com.

Seals may be provided between adjacent housing sections. For example, o-ring 560 (see FIG. 5) may be disposed between the housing section 550 and the bearing housing 530, o-ring 562 (see FIG. 5) may be disposed between the first mechanical seal housing 524 and the central section 522, and o-ring 564 (see FIG. 6) may be disposed between the second mechanical seal housing 526 and the central section 522.

Mixing Chamber 330

Figure 7:
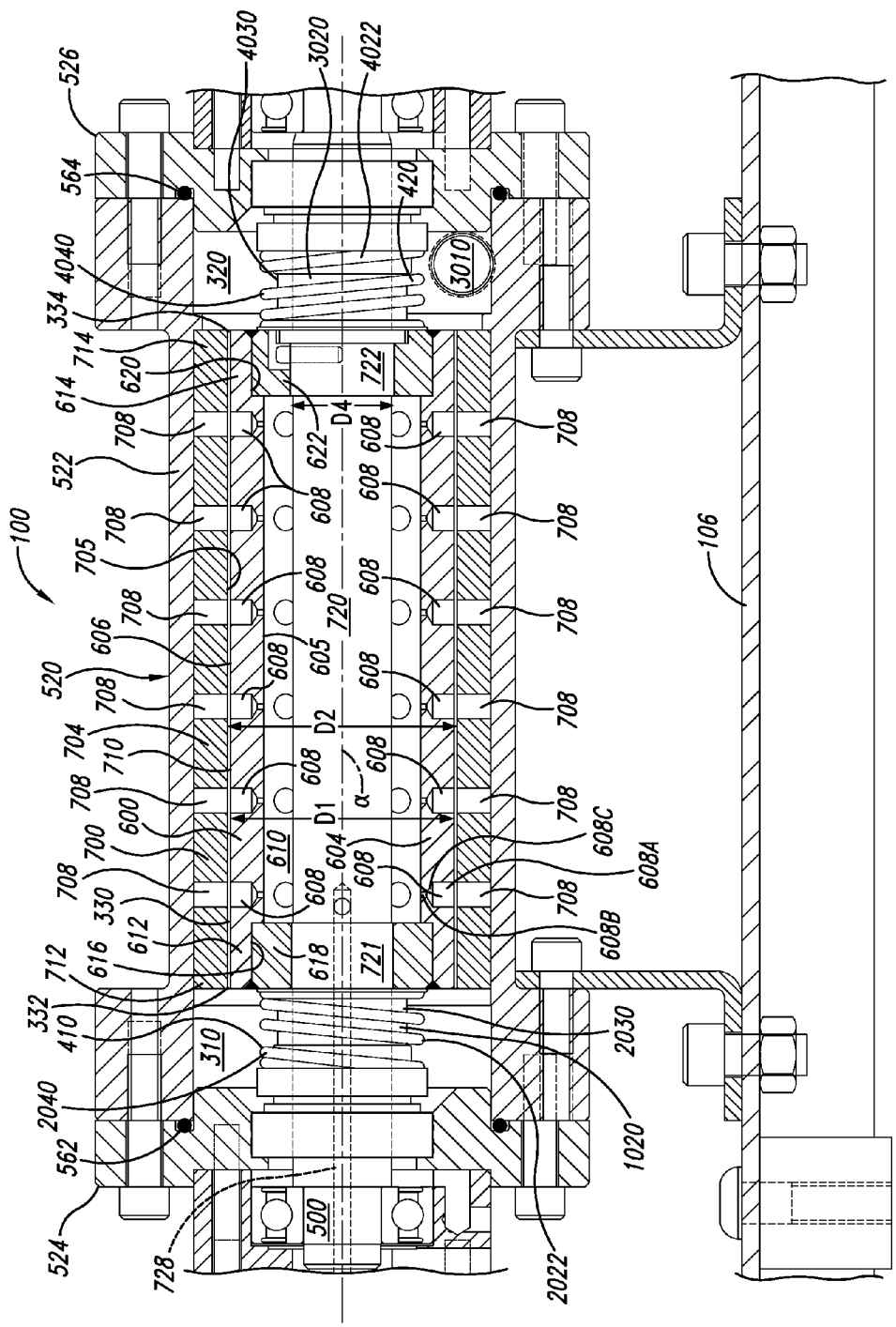
FIG. 7 is a fragmentary cross-sectional view of a side portion of the mixing device of FIG. 2 located between the first side portion of FIG. 5 and the second side portion of FIG. 6.

Turning now to FIG. 7, the mixing chamber 330 is disposed inside the central section 522 of the housing 520 between the first mechanical seal housing 524 and the second mechanical seal housing 526. The mixing chamber 330 is formed between two components of the mixing device 100, a rotor 600 and a stator 700. The rotor 600 may have a sidewall 604 with an inside surface 605 defining a generally hollow inside portion 610 and an outside surface 606. The sidewall 604 may be about 0.20 inches to about 0.75 inches thick. In some embodiments, the sidewall 604 is about 0.25 inches thick. However, because the mixing device 100 may be scaled to suit a particular application, embodiments of the device having a sidewall 604 that is thicker or thinner than the values provided are within the scope of the present teachings. The sidewall 604 includes a first end portion 612 and a second end portion 614 and a plurality of through-holes 608 formed between the first end portion 612 and the second end portion 614. Optionally, the outside surface 606 of the sidewall 604 may include other features such as apertures, projections, textures, and the like. The first end portion 612 has a relieved portion 616 configured to receive a collar 618 and the second end portion 614 has a relieved portion 620 configured to receive a collar 622.

The rotor 600 is disposed inside the stator 700. The stator 700 has a sidewall 704 with an inside surface 705 defining a generally hollow inside portion 710 into which the rotor 600 is disposed. The sidewall 704 may be about 0.1 inches to about 0.3 inches thick. In some embodiments, the sidewall 604 is about 1.5 inches thick. The stator 700 may be non-rotatably coupled to the housing 520 in a substantially stationary position. Alternatively, the stator 700 may integrally formed with the housing 520. The sidewall 704 has a first end portion 712 and a second end portion 714. Optionally, a plurality of apertures 708 are formed in the sidewall 704 of the stator 700 between the first end portion 712 and the second end portion 714. Optionally, the inside surface 705 of the sidewall 704 may include other features such as through-holes, projections, textures, and the like.

The rotor 600 rotates with respect to the stationary stator 700 about an axis of rotation "a" in a direction indicated by arrow "C3" in FIG. 9. Each of the rotor 600 and the stator 700 may be generally cylindrical in shape and have a longitudinal axis. The rotor 600 has an outer diameter "D1" and the stator 700 may have an inner diameter "D2." The diameter "D1" may range, for example, from about 0.5 inches to about 24 inches. In some embodiments, the diameter "D1" is about 3.04 inches. In some embodiments, the diameter "D1" is about 1.7 inches. The diameter "D2," which is larger than the diameter "D1," may range from about 0.56 inches to about 24.25 inches. In some embodiments, the diameter "D2" is about 4 inches. Therefore, the mixing chamber 330 may have a ring-shaped cross-sectional shape that is about 0.02 inches to about 0.125 inches thick (i.e., the difference between the diameter "D2" and the diameter "D1"). In particular embodiments, the mixing chamber 330 is about 0.025 inches thick. The channel 32 between the rotor 12 and the stator 34 of prior art device 10 (see FIG. 1) has a ring-shaped cross-sectional shape that is about 0.09 inches thick. Therefore, in particular embodiments, the thickness of the mixing chamber 330 is less than about one third of the channel 32 of the prior art device 10.

The longitudinal axis of the rotor 600 may be aligned with its axis of rotation "α." The longitudinal axis of the rotor 600 may be aligned with the longitudinal axis of the stator 700. The rotor 600 may have a length of about 3 inches to about 6 inches along the axis of rotation "α." In some embodiments, the rotor 600 may have a length of about 5 inches along the axis of rotation "α." The stator 700 may have a length of about 3 inches to about 6 inches along the axis of rotation "α." In some embodiments, the stator 700 may have a length of about 5 inches along the axis of rotation "α."

While the rotor 600 and the stator 700 have been depicted as having a generally cylindrical shape, those of ordinary skill in the art appreciate that alternate shapes may be used. For example, the rotor 600 and the stator 700 may be conically, spherically, arbitrarily shaped, and the like. Further, the rotor 600 and the stator 700 need not be identically shaped. For example, the rotor 600 may be cylindrically shaped and the stator 700 rectangular shaped or vise versa.

The apertures 708 of the stator 700 and the through-holes 608 depicted in FIGS. 4-7 are generally cylindrically shaped. The diameter of the through-holes 608 may range from about 0.1 inches to about 0.625 inches. The diameter of the apertures 708 may range from about 0.1 inches to about 0.625 inches. One or more of apertures 708 of the stator 700 may have a diameter that differs from the diameters of the other apertures 708. For example, the apertures 708 may increase in diameter from the first end portion 712 of the stator 700 to the second end portion 714 of the stator 700, the apertures 708 may decrease in diameter from the first end portion 712 of the stator 700 to the second end portion 714 of the stator 700, or the diameters of the apertures 708 may vary in another manner along the stator 700. One or more of through-holes 608 of the rotor 600 may have a diameter that differs from the diameters of the other through-holes 608. For example, the through-holes 608 may increase in diameter from the first end portion 612 of the rotor 600 to the second end portion 614 of the rotor 600, the through-holes 608 may decrease in diameter from the first end portion 612 of the rotor 600 to the second end portion 614 of the rotor 600, or the diameters of the through-holes 608 may vary in another manner along the rotor 600.

As described below with reference to alternate embodiments, the apertures 708 and the through-holes 608 may have shapes other than generally cylindrical and such embodiments are within the scope of the present invention. For example, the through-holes 608 may include a narrower portion, an arcuate portion, a tapered portion, and the like. Referring to FIG. 7, each of the through-holes 608 includes an outer portion 608A, a narrow portion 608B, and a tapered portion 608C providing a transition between the outer portion 608A and the narrow portion 608B. Similarly, the apertures 708 may include a narrower portion, an arcuate portion, a tapered portion, and the like.

FIG. 8 provides a non-limiting example of a suitable arrangement of the apertures 708 of the stator 700 and the through-holes 608 of the rotor 600. The apertures 708 of the stator 700 may be arranged in substantially parallel lateral rows "SLAT-1" through "SLAT-6" substantially orthogonal to the axis of rotation "α." The apertures 708 of the stator 700 may also be arranged in substantially parallel longitudinal rows "SLONG-1" through "SLONG-7" substantially parallel with the axis of rotation "α." In other words, the apertures 708 of the stator 700 may be arranged in a grid-like pattern of orthogonal rows (i.e., the lateral rows are orthogonal to the longitudinal rows) having the longitudinal rows "SLONG-1" through "SLONG-7" substantially parallel with the axis of rotation "α."

Like the apertures 708 of the stator 700, the through-holes 608 of the rotor 600 may be arranged in substantially parallel lateral rows "RLAT-1" through "RLAT-6" substantially orthogonal to the axis of rotation "α." However, instead of being arranged in a grid-like pattern of orthogonal rows, the through-holes 608 of the rotor 600 may also be arranged in substantially parallel rows "RLONG-1" through "RLONG-7" that extend longitudinally along a helically path. Alternatively, the through-holes 608 of the rotor 600 may also be arranged in substantially parallel rows "RLONG-1" through "RLONG-7" that extend longitudinally at an angle other than parallel with the axis of rotation "α."

The apertures 708 of the stator 700 and the through-holes 608 of the rotor 600 may be configured so that when the rotor 600 is disposed inside the stator 700 the lateral rows "SLAT-1" to "SLAT-6" at least partially align with the lateral rows "RLAT-1" to "RLAT-6," respectively. In this manner, as the rotor 600 rotates inside the stator 700, the through-holes 608 pass by the apertures 708.

The through-holes 608 in each of the lateral rows "RLAT-1" to "RLAT-6" may be spaced apart laterally such that all of the through-holes 608 in the lateral row align, at least partially, with the apertures 708 in a corresponding one of the lateral rows "SLAT-1" to "SLAT-6" of the stator 700 at the same time. The longitudinally extending rows "RLONG-1" through "RLONG-6" may be configured such that the through-holes 608 in the first lateral row "RLAT-1" in each of the longitudinally extending rows passes completely by the apertures 708 of the corresponding lateral row "SLAT-1" before the through-holes 608 in the last lateral row "RLAT-6" begin to partially align with the apertures 708 of the corresponding last lateral row "SLAT-6" of the stator 700.

While, in FIG. 8, six lateral rows and six longitudinally extending rows have been illustrated with respect to the rotor 600 and six lateral rows and seven longitudinally extending rows have been illustrated with respect stator 700, it is apparent to those of ordinary skill in the art that alternate numbers of lateral rows and/or longitudinal rows may be used with respect to the rotor 600 and/or stator 700 without departing from the present teachings.

To ensure that only one pair of openings between corresponding lateral rows will be coincident at any one time, the number of apertures 708 in each of the lateral rows "SLAT-1" to "SLAT-6" on the stator 700 may differ by a predetermined number (e.g., one, two, and the like) the number of through-holes 608 in each of the corresponding lateral rows "RLAT-1" to "RLAT-6" on the rotor 600. Thus, for example, if lateral row "RLAT-1" has twenty through-holes 608 evenly spaced around the circumference of rotor 600, the lateral row "SLAT-1" may have twenty apertures 708 evenly spaced around the circumference of stator 700.

Returning to FIG. 7, the mixing chamber 330 has an open first end portion 332 and an open second end portion 334. The through-holes 608 formed in the sidewall 604 of the rotor 600 connect the inside portion 610 of the rotor 600 with the mixing chamber 330.

The rotor 600 is rotated inside the stator 700 by the drive shaft 500 aligned with the axis of rotation "a" of the rotor 600. The drive shaft 500 may be coupled to the first end portion 612 and the second end portion 614 of the rotor 600 and extend through its hollow inside portion 610. In other words, a portion 720 of the drive shaft 500 is disposed in the hollow inside portion 610 of the rotor 600.

The collar 618 is configured to receive a portion 721 of the drive shaft 500 disposed in the hollow inside portion 610 and the collar 622 is configured to receive a portion 722 of the drive shaft 500 disposed in the hollow inside portion 610.

The portion 721 has an outer diameter "D3" that may range from about 0.5 inches to about 2.5 inches. In some embodiments, the diameter "D3" is about 0.625 inches. The portion 722 has an outer diameter "D4" that may be substantially similar to the diameter "D3," although, this is not required. The diameter "D4" may range from about 0.375 inches to about 2.5 inches.

The rotor 600 may be non-rotationally affixed to the portion 721 and the portion 722 of the drive shaft 500 by the collar 618 and the collar 622, respectively. By way of example, each of the collars 618 and 622 may be installed inside relieved portions 616 and 620, respectively. Then, the combined rotor 600 and collars 618 and 622 may be heated to expand them. Next, the drive shaft 500 is inserted through the collars 618 and 622 and the assembly is allowed to cool. As the collars 618 and 622 shrink during cooling, they tighten around the portions 722A and 722B of the drive shaft 500, respectively, gripping it sufficiently tightly to prevent the drive shaft 500 from rotating relative to the rotor 600. The collar 618, which does not rotate with respect to either the portion 721 or the relieved portion 616, translates the rotation of the drive shaft 500 to the first end portion 612 the rotor 600. The collar 622, which does not rotate with respect to either the portion 722 or the relieved portion 620, translates the rotation of the drive shaft 500 to the second end portion 614 of the rotor 600. The drive shaft 500 and the rotor 600 rotate together as a single unit.

The drive shaft 500 may have a first end portion 724 (see FIG. 5) and a second end portion 726 (see FIG. 6). The first end portion 724 may have a diameter "D5" of about 0.5 inches to about 1.75 inches. In particular embodiments, the diameter "D5" may be about 1.25 inches. The second end portion 726 may have a diameter "D6" that may be substantially similar to diameter "D5."

The second material 120 may be transported into the mixing chamber 330 through one of the first end portion 724 and the second end portion 726 of the rotating drive shaft 500. The other of the first end portion 724 and the second end portion 726 of the drive shaft 500 may be coupled to the motor 510. In the embodiment depicted in FIGS. 5 and 6, the second material 120 is transported into the mixing chamber 330 through the first end portion 724 and the second end portion 726 of the drive shaft 500 is coupled to the motor 510.

Turning to FIG. 5, the drive shaft 500 may have a channel 728 formed therein that extends from first end portion 724 into the portion 720 disposed in the inside portion 610 of the rotor 600. The channel 728 has an opening 730 formed in the first end portion 724. When the mixing device 100 is operating, the second material 120 is introduced into the channel 728 through the opening 730.

A valve 732 may be disposed inside a portion of the channel 728 located in the first end portion 724 of the drive shaft 500. The valve 732 may restrict or otherwise control the backward flow of the second material 120 from inside the hollow inside portion 610 through the channel 728 and/or the forward flow of the second material 120 into the channel 728. The valve 732 may include any valve known in the art including a check valve. A suitable check valve includes a part number "CKFA1876205A," free flow forward check valve, manufactured by The Lee Company USA having an office in Bothell, Wash. and operating a website at www.theleeco.com.

The drive shaft 500 may include an aperture 740 located in the inside portion 610 of the rotor 600 that connects the channel 728 with the inside portion 610 of the rotor 600. While only a single aperture 740 is illustrated in FIG. 5, it is apparent to those of ordinary skill in the art that multiple apertures may be used to connect the channel 728 with the inside portion 610 of the rotor 600.

Referring to FIG. 2, optionally, the external pump 220 may pump the second material 120 into the mixing device 100. The pump 220 may include any suitable pump known in the art. By way of non-limiting example, the pump 220 may include any suitable pump known in the art including a diaphragm pump, a chemical pump, a peristaltic pump, a gravity fed pump, a piston pump, a gear pump, a combination of any of the aforementioned pumps, and the like. If the second material 120 is a gas, the gas may be pressurized and forced into the opening 730 formed in the first end portion 724 of the drive shaft 500 by releasing the gas from the source 122.

The pump 220 or the source 122 is coupled to the channel 728 by the valve 732. The second material 120 transported inside the channel 728 exits the channel 728 into the inside portion 610 of the rotor 600 through the aperture 740. The second material 120 subsequently exits the inside portion 610 of the rotor 600 through the through-holes 608 formed in the sidewall 608 of the rotor 600.

Referring to FIG. 5, the mixing device 100 may include a seal assembly 750 coupled to the first end portion 724 of the drive shaft 500. The seal assembly 750 is maintained within a chamber 752 defined in the housing 520. The chamber 752 has a first end portion 754 spaced across the chamber from a second end portion 756. The chamber 752 also includes an input port 758 and an output port 759 that provide access into the chamber 752. The chamber 752 may be defined by housing section 550 and the bearing housing 530. The first end portion 754 may be formed in the housing section 550 and the second end portion 756 may be adjacent to the bearing housing 530. The input port 758 may be formed in the bearing housing 530 and the output port 759 may be formed in the housing section 550.

The seal assembly 750 includes a first stationary seal 760 installed in the first end portion 754 of the chamber 752 in the housing section 550 and the bearing housing 530. The first stationary seal 760 extends around a portion 762 of the first end portion 724 of the drive shaft 500. The seal assembly 750 also includes a second stationary seal 766 installed in the second end portion 756 of the chamber 752 in the bearing housing 530. The second stationary seal 766 extends around a portion 768 of the first end portion 724 of the drive shaft 500.

The seal assembly 750 includes a rotating assembly 770 that is non-rotatably coupled to the first end portion 724 of the drive shaft 500 between the portion 762 and the portion 768. The rotating assembly 770 rotates therewith as a unit. The rotating assembly 770 includes a first seal 772 opposite a second seal 774. A biasing member 776 (e.g., a spring) is located between the first seal 772 and the second seal 774. The biasing member 776 biases the first seal 772 against the first stationary seal 760 and biases the second seal 774 against the second stationary seal 766.

A cooling lubricant is supplied to the chamber 752 and around rotating assembly 770. The lubricant enters the chamber 752 through the input port 758 and exits the chamber 752 through output port 759. The lubricant may lubricate the bearing assembly 540 housed by the bearing housing 530. A chamber 570 may be disposed between the bearing housing 530 and the mechanical seal housing 524. The bearing housing 530 may also include a second input port 759 connected to the chamber 570 into which lubricant may be pumped. Lubricant pumped into the chamber 570 may lubricate the bearing assembly 540. The seal assembly 750 may significantly, if not greatly, reduce frictional forces within this portion of the device caused by the rotation of the rotor 600 and may increase the active life of the seals 770. The seals may include surfaces constructed using silicon carbide.

Referring to FIG. 9, as the rotor 600 rotates about the axis of rotation "a" in the direction indicated by arrow "C1," the rotor expels the second material 120 into the mixing chamber 330. The expelled bubbles, droplets, particles, and the like of the second material 120 exit the rotor 600 and are imparted with a circumferential velocity (in a direction indicated by arrow "C3") by the rotor 600. The second material 120 may forced from the mixing chamber 330 by the pump 220 (see FIG. 2), the centrifugal force of the rotating rotor 600, buoyancy of the second material 120 relative to the first material 110, and a combination thereof.

Motor 510

Returning to FIG. 6, the second end portion 726 of the drive shaft 500 may be coupled to a rotating spindle 780 of a motor 510 by a coupler 900. The spindle 780 may have a generally circular cross-sectional shape with a diameter "D7" of about 0.25 inches to about 2.5 inches. In particular embodiments, the diameter "D7" may be about 0.25 inches to about 1.5 inches. While in the embodiment depicted in FIG. 6, the diameter "D5" of the first end portion 724 of the drive shaft 500 is substantially equal to the diameter "D7" and the spindle 780, embodiments in which one of the diameter "D5" and the diameter "D7" is larger than the other are within the scope of the present invention.

Referring also to FIG. 4, it may be desirable to cover or shield the coupler 900. In the embodiment illustrated in FIGS. 4 and 6, a drive guard 910 covers the coupler 900. The drive guard 910 may be generally U-shaped having a curved portion 914 flanked by a pair of substantially linear portions 915 and 916. The distal end of each of the substantially linear portions 915 and 916 of the drive guard 910 may have a flange 918 and 919, respectively. The drive guard 910 may be fastened by each of its flanges 918 and 919 to the base 106.

The motor 510 may be supported on the base 106 by a support member 920. The support member 920 may be coupled to the motor 510 near the spindle 780. In the embodiment depicted, the support member 920 includes a through-hole through which the spindle 780 passes. The support member 920 may be coupled to the motor 510 using any method known in the art, including bolting the support member 920 to the motor 510 with one or more bolts 940.

The coupler 900 may include any coupler suitable for transmitting a sufficient amount of torque from the spindle 780 to the drive shaft 500 to rotate the rotor 600 inside to the stator 700. In the embodiment illustrated in FIGS. 4 and 6, the coupler 900 is a bellows coupler. A bellows coupler may be beneficial if the spindle 780 and the drive shaft 500 are misaligned. Further, the bellows coupler may help absorb axial forces exerted on the drive shaft 500 that would otherwise be translated to the spindle 780. A suitable bellows coupler includes a model "BC32-8-8-A," manufactured by Ruland Manufacturing Company, Inc. of Marlborough, Mass., which operates a website at www.ruland.com.

The motor 510 may rotate the rotor 600 at about 0.1 revolutions per minute ("rpm") to about 7200 rpm. The motor 510 may include any motor suitable for rotating the rotor 600 inside to the stator 700 in accordance with the present teachings. By way of non-limiting example, a suitable motor may include a one-half horsepower electric motor, operating at 230/460 volts and 3450 per minute ("rpm"). A suitable motor includes a model "C4T34NC4C" manufactured by LEESON Electric Corporation of Grafton, Wis., which operates a website at www.leeson.com.

First Chamber 310

Turning to FIGS. 4 and 7, the first chamber 320 is disposed inside the central section 522 of the housing 520 between the first mechanical seal housing 524 and the first end portions 612 and 712 of the rotor 600 and the stator 700, respectively. The first chamber 310 may be annular and have a substantially circular cross-sectional shape. The first chamber 310 and the mixing chamber 330 form a continuous volume. A portion 1020 of the drive shaft 500 extends through the first chamber 310.

As may best be viewed in FIG. 4, the first chamber 310 has an input port 1010 through which the first material 110 enters the mixing device 100. The first material 110 may be pumped inside the first chamber 310 by the external pump 210 (see FIG. 2). The external pump 210 may include any pump known in the art for pumping the first material 110 at a sufficient rate to supply the first chamber 310.

The input port 1010 is oriented substantially orthogonally to the axis of rotation "α." Therefore, the first material 110 enters the first chamber 310 with a velocity tangential to the portion 1020 of the drive shaft 500 extending through the first chamber 310. The tangential direction of the flow of the first material 110 entering the first chamber 310 is identified by arrow "T1." In the embodiment depicted in FIGS. 4 and 7, the input port 1010 may be offset from the axis of rotation "α." As is apparent to those of ordinary skill in the art, the direction of the rotation of the drive shaft 500 (identified by arrow "C1" in FIG. 9), has a tangential component. The input port 1010 is positioned so that the first material 110 enters the first chamber 310 traveling in substantially the same direction as the tangential component of the direction of rotation of the drive shaft 500.

The first material 110 enters the first chamber 310 and is deflected by the inside of the first chamber 310 about the portion 1020 of the drive shaft 500. In embodiments wherein the first chamber 310 has a substantially circular cross-sectional shape, the inside of the first chamber 310 may deflect the first material 110 in a substantially circular path (identified by arrow "C2" in FIG. 9) about the portion 1020 of the drive shaft 500. In such an embodiment, the tangential velocity of the first material 110 may cause it to travel about the axis of rotation "α" at a circumferential velocity, determined at least in part by the tangential velocity.

Once inside the first chamber 310, the first material 110 may be pumped from the first chamber 310 into the mixing chamber 330 by the pump 410 residing inside the first chamber 310. In embodiments that include the external pump 210 (see FIG. 2), the external pump 210 may be configured to pump the first material 110 into the first chamber 310 at a rate at least as high as a rate at which the pump 410 pumps the first material 110 from the first chamber 310.

The first chamber 310 is in communication with the open first end portion 332 of the mixing chamber 330 and the first material 110 inside the first chamber 310 may flow freely into the open first end portion 332 of the mixing chamber 330. In this manner, the first material 110 does not negotiate any corners or bends between the mixing chamber 330 and the first chamber 310. In the embodiment depicted, the first chamber 310 is in communication with the entire open first end portion 332 of the mixing chamber 330. The first chamber 310 may be filled completely with the first material 110.

The pump 410 is powered by the portion 1020 of the drive shaft 500 extending through the first chamber 310. The pump 410 may include any pump known in the art having a rotating pump member 2022 housed inside a chamber (i.e., the first chamber 310) defined by a stationary housing (i.e., the housing 520). Non-limiting examples of suitable pumps include rotary positive displacement pumps such as progressive cavity pumps, single screw pumps (e.g., Archimedes screw pump), and the like.

The pump 410 depicted in FIGS. 7 and 9, is generally referred to as a single screw pump. In this embodiment, the pump member 2022 includes a collar portion 2030 disposed around the portion 1020 of the drive shaft 500. The collar portion 2030 rotates with the portion 1020 of the drive shaft 500 as a unit. The collar portion 2030 includes one or more fluid displacement members 2040. In the embodiment depicted in FIGS. 7 and 9, the collar portion 2030 includes a single fluid displacement member 2040 having a helical shape that circumscribes the collar portion 2030 along a helical path.

Referring to FIG. 9, the inside of the first chamber 310 is illustrated. The pump 410 imparts an axial flow (identified by arrow "A1" and arrow "A2") in the first material 110 inside the first chamber 310 toward the open first end portion 332 of the mixing chamber 330. The axial flow of the first material 110 imparted by the pump 410 has a pressure that may exceed the pressure obtainable by the external pump of the prior art device 10 (see FIG. 1).

The pump 410 may also be configured to impart a circumferential flow (identified by arrow "C2") in the first material 110 as it travels toward the open first end portion 332 of the mixing chamber 330. The circumferential flow imparted in the first material 110 before it enters the mixing chamber 330 causes the first material 110 to enter the mixing chamber 330 already traveling in the desired direction at an initial circumferential velocity. In the prior art device 10 depicted in FIG. 1, the first material 110 entered the channel 32 of the prior art device 10 without a circumferential velocity. Therefore, the rotor 12 of the prior art device 10 alone had to impart a circumferential flow into the first material 110. Because the first material 110 is moving axially, in the prior art device 10, the first material 110 traversed at least a portion of the channel 32 formed between the rotor 12 and the stator 30 at a slower circumferential velocity than the first material 110 traverses the mixing chamber 330 of the mixing device 100. In other words, if the axial velocity of the first material 110 is the same in both the prior art device 10 and the mixing device 100, the first material 110 may complete more revolutions around the rotational axis "α" before traversing the axial length of the mixing chamber 330, than it would complete before traversing the axial length of the channel 32. The additional revolutions expose the first material 110 (and combined first material 110 and second material 120) to a substantially larger portion of the effective inside surface 706 (see FIG. 7) of the stator 700.

In embodiments including the external pump 210 (see FIG. 2), the circumferential velocity imparted by the external pump 210 combined with the input port 1010 being oriented according to the present teachings, may alone sufficiently increase the revolutions of the first material 110 (and combined first material 110 and second material 120) about the rotational axis "α." Further, in some embodiments, the circumferential velocity imparted by the pump 210 and the circumferential velocity imparted by the pump 410 combine to achieve a sufficient number of revolutions of the first material 110 (and combined first material 110 and second material 120) about the rotational axis "α." As is appreciated by those of ordinary skill in the art, other structural elements such as the cross-sectional shape of the first chamber 310 may contribute to the circumferential velocity imparted by the pump 210, the pump 410, and a combination thereof.

Figure 10:
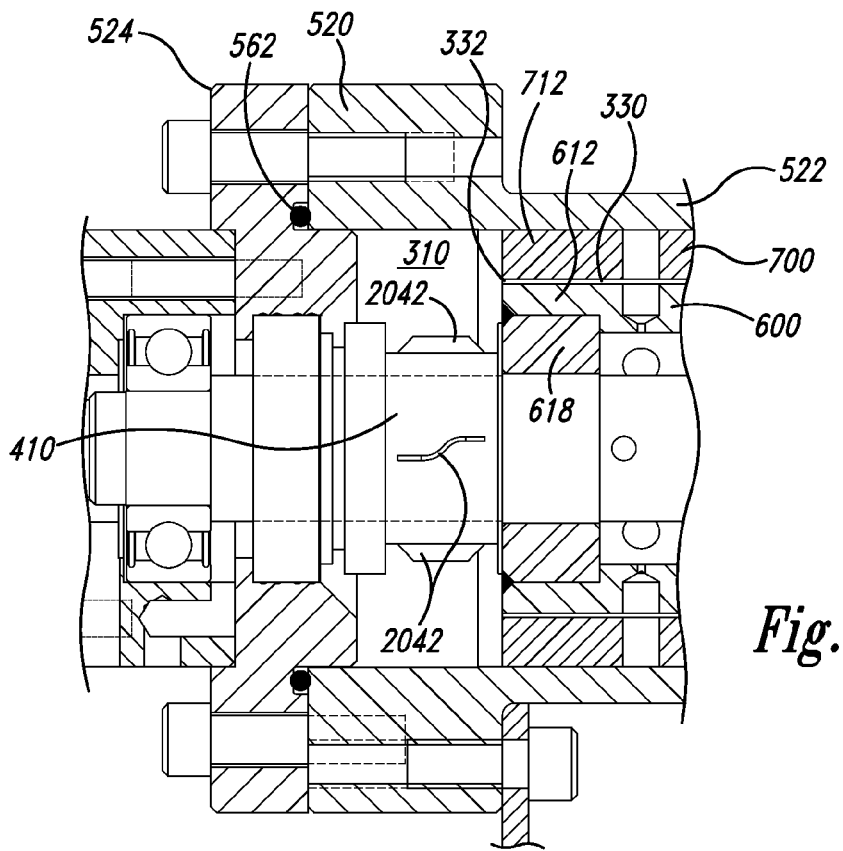
FIG. 10 is a fragmentary cross-sectional view of the inside of a first chamber of the mixing device of FIG. 2 including an alternate embodiment of the pump 410.

In an alternate embodiment depicted in FIG. 10, the pump 410 may include one or more vanes 2042 configured to impart a circumferential flow in the first material 110 as it travels toward the open first end portion 332 of the mixing chamber 330.

Second Chamber 320

Turning now to FIGS. 4 and 7, the second chamber 320 is disposed inside the central section 522 of the housing 520 between the second mechanical seal housing 526 and the second end portions 614 and 714 of the rotor 600 and the stator 700, respectively. The second chamber 320 may be substantially similar to the first chamber 310. However, instead of the input port 1010, the second chamber 320 may include an output port 3010. A portion 3020 of the drive shaft 500 extends through the second chamber 320.

The second chamber 320 and the mixing chamber 330 form a continuous volume. Further, the first chamber 310, the mixing chamber 330, and the second chamber 320 form a continuous volume. The first material 110 flows through the mixing device 100 from the first chamber 310 to the mixing chamber 330 and finally to the second chamber 320. While in the mixing chamber 330, the first material 110 is mixed with the second material 120 to form the output material 102. The output material 102 exits the mixing device 100 through the output port 3010. Optionally, the output material 102 may be returned to the input port 1010 and mixed with an additional quantity of the second material 120, the third material 130, or a combination thereof.

The output port 3010 is oriented substantially orthogonally to the axis of rotation "α" and may be located opposite the input port 1010 formed in the first chamber 310. The output material 102 enters the second chamber 320 from the mixing chamber 330 having a circumferential velocity (in the direction indicated by arrow "C3" in FIG. 9) imparted thereto by the rotor 600. The circumferential velocity is tangential to the portion 3020 of the drive shaft 500 extending through the second chamber 320. In the embodiment depicted in FIGS. 4, 6, and 7, the output port 3010 may be offset from the axis of rotation "α." The output port 3010 is positioned so that the output material 102, which enters the second chamber 320 traveling in substantially the same direction in which the drive shaft 500 is rotating (identified in FIG. 9 by arrow "C1"), is traveling toward the output port 3010.

The output material 102 enters the second chamber 320 and is deflected by the inside of the second chamber 320 about the portion 3020 of the drive shaft 500. In embodiments wherein the second chamber 320 has a substantially circular cross-sectional shape, the inside of the second chamber 320 may deflect the output material 102 in a substantially circular path about the portion 3020 of the drive shaft 500.

Referring to FIG. 2, optionally, the output material 102 may be pumped from inside the second chamber 320 by the external pump 430. The external pump 430 may include any pump known in the art for pumping the output material 102 at a sufficient rate to avoid limiting throughput of the mixing device 100. In such an embodiment, the external pump 430 may introduce a tangential velocity (in a direction indicated by arrow "T2" in FIGS. 4 and 11) to at least a portion of the output material 102 as the external pump 430 pumps the output material 102 from the second chamber 320. The tangential velocity of the portion of the output material 102 may cause it to travel about the axis of rotation "α" at a circumferential velocity, determined in part by the tangential velocity.

Pump 420

Turning to FIGS. 6 and 7, the pump 420 residing inside the second chamber 320 may pump the output material 102 from the second chamber 320 into the output port 3010 and/or from the mixing chamber 330 into the second chamber 320. In embodiments that include the external pump 430, the external pump 430 may be configured to pump the output material 102 from the second chamber 320 at a rate at least as high as a rate at which the pump 420 pumps the output material 102 into the output port 3010.

The second chamber 320 is in communication with the open second end portion 334 of the mixing chamber 330 and the output material 102 inside the mixing chamber 330 may flow freely from the open second end portion 334 into the second chamber 320. In this manner, the output material 102 does not negotiate any corners or bends between the mixing chamber 330 and the second chamber 320. In the embodiment depicted, the second chamber 320 is in communication with the entire open second end portion 334 of the mixing chamber 330. The second chamber 320 may be filled completely with the output material 102.

The pump 420 is powered by the portion 3020 of the drive shaft 500 extending through the second chamber 320. The pump 420 may be substantially identical to the pump 410. Any pump described above as suitable for use as the pump 410 may be used for the pump 420. While the pump 410 pumps the first material 110 into the mixing chamber 330, the pump 420 pumps the output material 102 from the mixing chamber 330. Therefore, both the pump 410 and the pump 420 may be oriented to pump in the same direction.

As is appreciated by those of ordinary skill in the art, the first material 110 may differ from the output material 102. For example, one of the first material 110 and the output material 102 may be more viscous than the other. Therefore, the pump 410 may differ from the pump 420. The pump 410 may be configured to accommodate the properties of the first material 110 and the pump 420 may be configured to accommodate the properties of the output material 102.

The pump 420 depicted in FIGS. 6 and 7, is generally referred to as a single screw pump. In this embodiment, the pump member 4022 includes a collar portion 4030 disposed around the portion 3020 of the drive shaft 500. The collar portion 4030 rotates with the portion 3020 of the drive shaft 500 as a unit. The collar portion 4030 includes one or more fluid displacement members 4040. The collar portion 4030 includes a single fluid displacement member 4040 having a helical shape that circumscribes the collar portion 4030 along a helical path.

Figure 11:
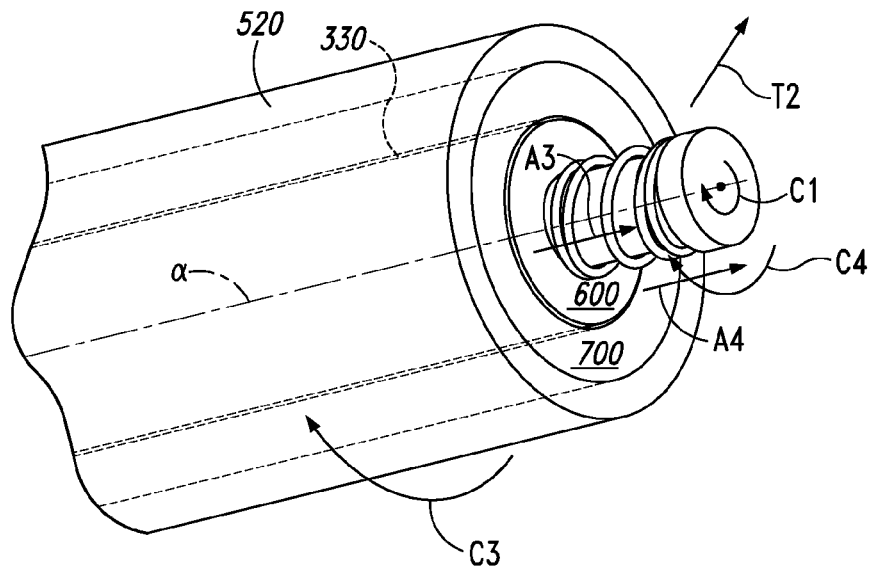
FIG. 11 is a perspective view of an inside of a second chamber of the mixing device of FIG. 2.

Referring to FIG. 11, the inside of the second chamber 320 is illustrated. The pump 420 imparts an axial flow (identified by arrow "A3" and arrow "A4") in the output material 102 inside the second chamber 320 away from the open second end portion 334 of the mixing chamber 330.

The pump 420 may be configured to impart a circumferential flow (identified by arrow "C4") in the output material 102 as it travels away from the open second end portion 334 of the mixing chamber 330. The circumferential flow imparted in the output material 102 may help reduce an amount of work required by the rotor 600. The circumferential flow also directs the output material 102 toward the output port 3010.

In an alternate embodiment, the pump 420 may have substantially the same configuration of the pump 410 depicted in FIG. 10. In such an embodiment, the one or more vanes 2042 are configured to impart a circumferential flow in the output material 102 as it travels away from the open second end portion 334 of the mixing chamber 330.

As is apparent to those of ordinary skill, various parameters of the mixing device 100 may be modified to obtain different mixing characteristics. Exemplary parameters that may be modified include the size of the through-holes 608, the shape of the through-holes 608, the arrangement of the through-holes 608, the number of through-holes 608, the size of the apertures 708, the shape of the apertures 708, the arrangement of the apertures 708, the number of apertures 708, the shape of the rotor 600, the shape of the stator 700, the width of the mixing chamber 330, the length of the mixing chamber 330, rotational speed of the drive shaft 500, the axial velocity imparted by the internal pump 410, the circumferential velocity imparted by the internal pump 410, the axial velocity imparted by the internal pump 420, the circumferential velocity imparted by the internal pump 420, the configuration of disturbances (e.g., texture, projections, recesses, apertures, and the like) formed on the outside surface 606 of the rotor 600, the configuration of disturbances (e.g., texture, projections, recesses, apertures, and the like) formed on the inside surface 706 of the stator 700, and the like.

Alternate Embodiment

Figure 12:
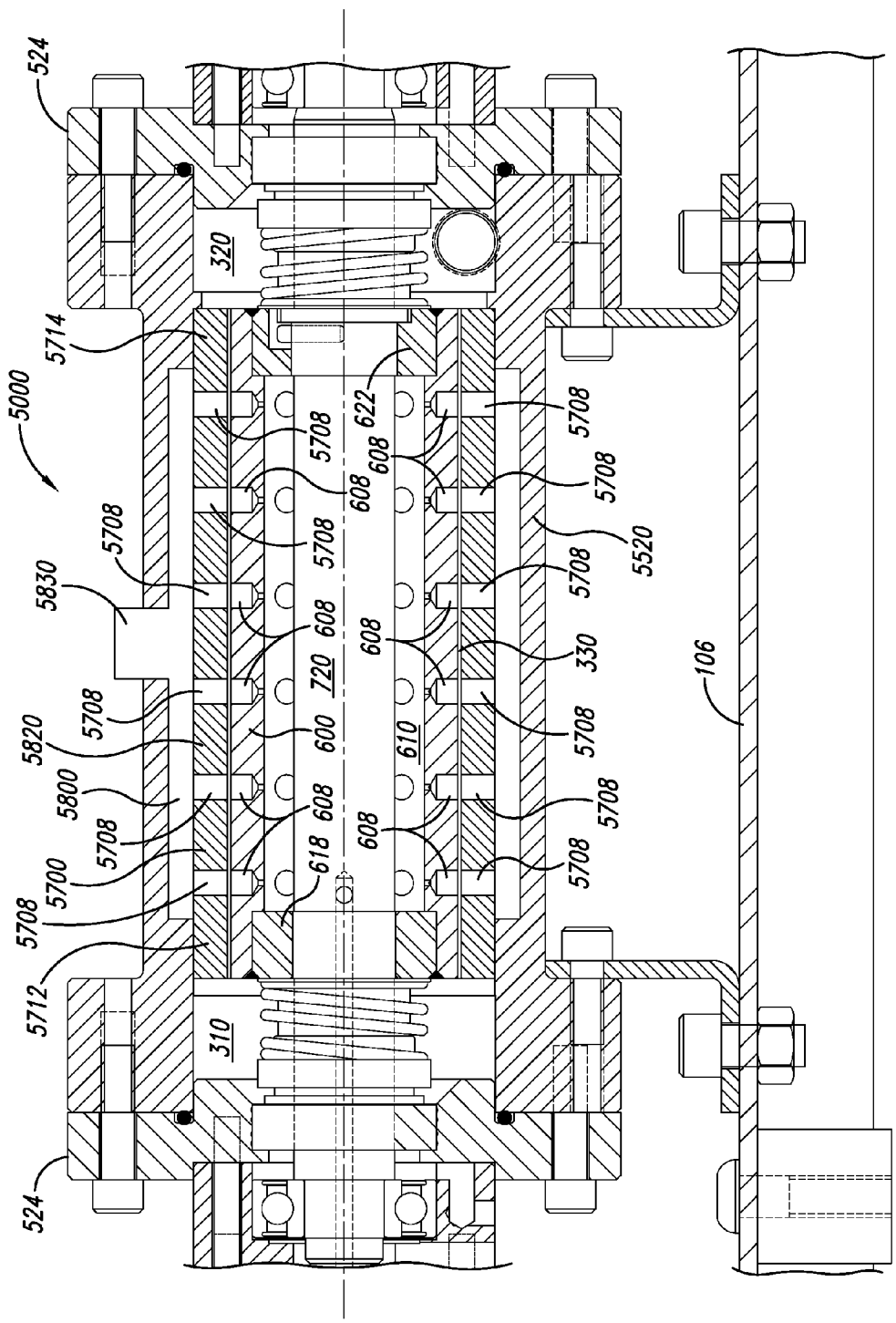
FIG. 12 is a fragmentary cross-sectional view of a side portion of an alternate embodiment of the mixing device.

Referring to FIG. 12, a mixing device 5000 is depicted. The mixing device 5000 is an alternate embodiment of the mixing device 100. Identical reference numerals have been used herein to identify components of the mixing device 5000 that are substantially similar corresponding components of the mixing device 100. Only components of the mixing device 5000 that differ from the components of the mixing device 100 will be described.

The mixing device 5000 includes a housing 5500 for housing the rotor 600 and the stator 5700. The stator 5700 may be non-rotatably couple by its first end portion 5712 and its second end portion 5714 to the housing 5500. A chamber 5800 is defined between the housing 5500 and a portion 5820 of the stator 5700 flanked by the first end portion 5712 and the second end portion 5714. The housing 5500 includes an input port 5830 which provides access into the chamber 5800. The input port 5830 may be oriented substantially orthogonally to the axis of rotation "α," however, this is not a requirement.

The stator 5700 includes a plurality of through-holes 5708 that connect the chamber 5800 and the mixing chamber 330 (defined between the rotor 600 and the stator 5700). An external pump 230 may be used to pump the third material 130 (which may be identical to the second material 120) into the chamber 5800 via the input port 5830. The third material 130 pumped into the chamber 5800 may enter the mixing chamber 330 via the through-holes 5708 formed in the stator 5700. The third material 130 may forced from the channel 5800 by the pump 230, buoyancy of the third material 130 relative to the first material 110, and a combination thereof. As the rotor 600 rotates, it may also draw the third material 130 from the channel 5800 into the mixing chamber 330. The third material 130 may enter the mixing chamber 330 as bubbles, droplets, particles, and the like, which are imparted with a circumferential velocity by the rotor 600.

Alternate Embodiment

Figure 13:
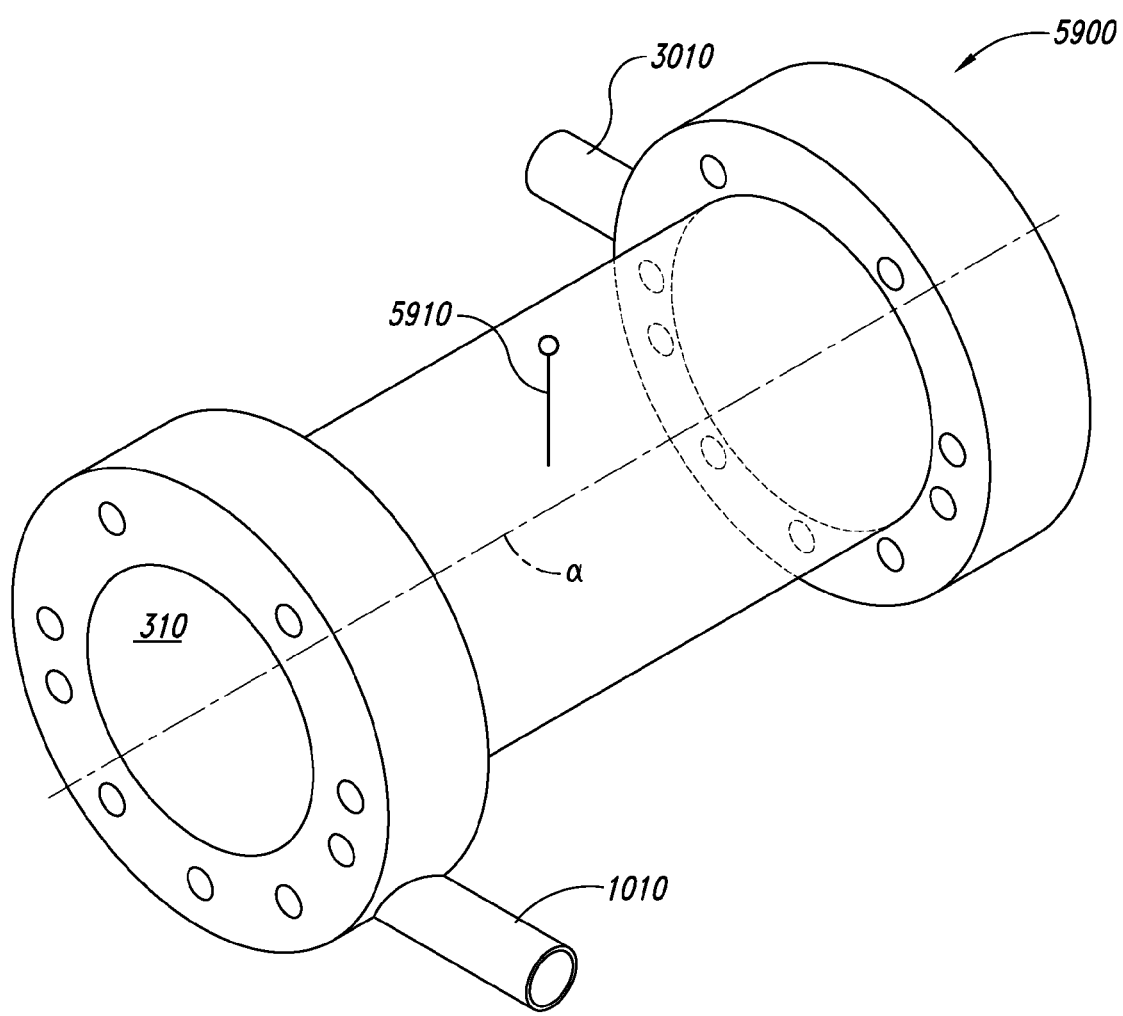
FIG. 13 is a perspective view of an alternate embodiment of a central section of the housing for use with an alternate embodiment of the mixing device.
Figure 14:
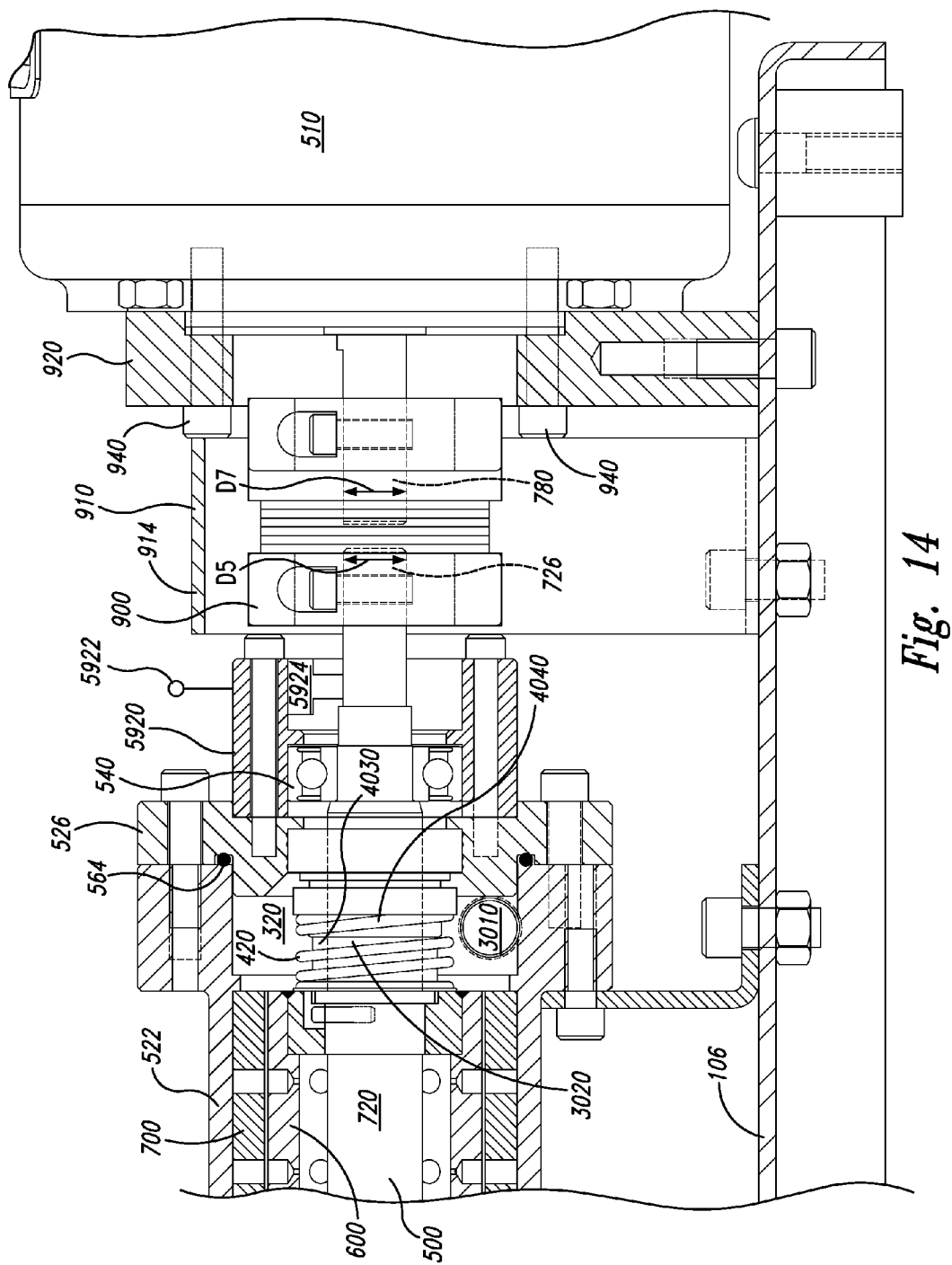
FIG. 14 is a fragmentary cross-sectional view of an alternate embodiment of a bearing housing for use with an alternate embodiment of the mixing device.

An alternate embodiment of the mixing device 100 may be constructed using a central section 5900 depicted in FIG. 13 and a bearing housing 5920 depicted in FIG. 14. FIG. 13 depicts the central section 5900 having in its interior the stator 700 (see FIG. 7). Identical reference numerals have been used herein to identify components associated with the central section 5900 that are substantially similar corresponding components of the mixing device 100. Only components of the central section 5900 that differ from the components of the central section 522 will be described. The central section 5900 and the stator 700 are both constructed from a conductive material such as a metal (e.g., stainless steel). The input port 1010 and the output port 3010 are both constructed from a nonconductive material such as plastic (e.g., PET, TEFLON®, nylon, PVC, polycarbonate, ABS, DELRIN®, polysulfone, etc.).

An electrical contact 5910 is coupled to the central section 5900 and configured to deliver a charge thereto. The central section 5900 conducts an electrical charge applied to the electrical contact 5910 to the stator 700. In further embodiments, the central section 5900 may be constructed from a nonconductive material. In such embodiments, the electrical contact 5910 may pass through the central section 5900 and coupled to the stator 700. The electric charge applied by the electrical contact 5910 to the stator 700 may help facilitate redox or other chemical reactions inside the mixing chamber 330.

Optionally, insulation (not shown) may be disposed around the central section 5900 to electrically isolate it from the environment. Further, insulation may be used between the central section 5900 and the first and second mechanical seals 524 and 526 that flank it to isolate it electrically from the other components of the mixing device.

Turning now to FIG. 14, the bearing housing 5920 will be described. The bearing housing 5920 is disposed circumferentially around the portion 726 of the drive shaft 500. An electrical contact 5922 is coupled to the bearing housing 5920. A rotating brush contact 5924 provides an electrical connection between the drive shaft 500 and the electrical contact 5922.

In this embodiment, the drive shaft 500 and the rotor 600 are both constructed from a conductive material such as a metal (e.g., stainless steel). The bearing housing 5920 may be constructed from either a conductive or a nonconductive material. An electrical charge is applied to the drive shaft 500 by the electrical contact 5922 and the rotating brush contact 5924. The electrical charge is conducted by the drive shaft 500 to the rotor 600.

The alternate embodiment of the mixing device 100 constructed using the central section 5900 depicted in FIG. 13 and the bearing housing 5920 depicted in FIG. 14 may be operated in at least two ways. First, the electrical contacts 5910 and 5922 may be configured not to provide an electrical charge to the stator 700 and the rotor 600, respectively. In other words, neither of the electrical contacts 5910 and 5922 are connected to a current source, a voltage source, and the like.

Alternatively, the electrical contacts 5910 and 5922 may be configured to provide an electrical charge to the stator 700 and the rotor 600, respectively. For example, the electrical contacts 5910 and 5922 may be coupled to a DC voltage source (not shown) supplying a steady or constant voltage across the electrical contacts 5910 and 5922. The negative terminal of the DC voltage source may be coupled to either of the electrical contacts 5910 and 5922 and the positive terminal of the DC voltage source may be coupled to the other of the electrical contacts 5910 and 5922. The voltage supplied across the electrical contacts 5910 and 5922 may range from about 0.0001 volts to about 1000 volts. In particular embodiments, the voltage may range from about 1.8 volts to about 2.7 volts. By way of another example, a pulsed DC voltage having a duty cycle of between about 1% to about 99% may be used.

While the above examples of methods of operating the mixing device apply a DC voltage across the electrical contacts 5910 and 5922, as is apparent to those of ordinary skill in the art, a symmetrical AC voltage or non symmetrical AC voltage having various shapes and magnitudes may be applied across the electrical contacts 5910 and 5922 and such embodiments are within the scope of the present invention.

Mixing Inside the Mixing Chamber 330

As mentioned above, in the prior art device 10 (shown in FIG. 1), the first material 110 entered the channel 32 between the rotor 12 and the stator 30 via a single limited input port 37 located along only a portion of the open second end of the channel 32. Likewise, the output material 102 exited the channel 32 via a single limited output port 40 located along only a portion of the open first end of the channel 32. This arrangement caused undesirable and unnecessary friction. By replacing the single limited inlet port 37 and the single limited outlet port 40 with the chambers 310 and 320, respectively, friction has been reduced. Moreover, the first material 110 does not negotiate a corner before entering the mixing chamber 330 and the output material 102 does not negotiate a corner before exiting the mixing chamber 330. Further, the chambers 310 and 320 provide for circumferential velocity of the material prior to entering, and after exiting the channel 32.

Accordingly, pressure drop across the mixing device 100 has been substantially reduced. In the embodiments depicted in FIGS. 2, 4-9, and 11, the pressure drop between the input port 1010 and the output port 3010 is only approximately 12 psi when the mixing device 100 is configured to produce about 60 gallons of the output material 102 per minute. This is an improvement over the prior art device 10 depicted in FIG. 1, which when producing about 60 gallons of output material per minute was at least 26 psi. In other words, the pressure drop across the mixing device 100 is less than half that experienced by the prior art device 10.

According to additional aspects, the inclusion of pumps 410 and 420, which are powered by the drive shaft 500, provides a configuration that is substantially more efficient in mixing materials and that requires less energy than the external pumps used in the prior art.

Micro-Cavitation

During operation of the mixing device 100, the input materials may include the first material 110 (e.g., a fluid) and the second material 120 (e.g., a gas). The first material 110 and the second material 120 are mixed inside the mixing chamber 330 formed between the rotor 600 and the stator 700. Rotation of the rotor 600 inside the stator 700 agitates the first material 110 and the second material 120 inside the mixing chamber 330. The through-holes 608 formed in the rotor 600 and/or the apertures 708 formed in the stator 700 impart turbulence in the flow of the first material 110 and the second material 120 inside the mixing chamber 330.

Figure 15:
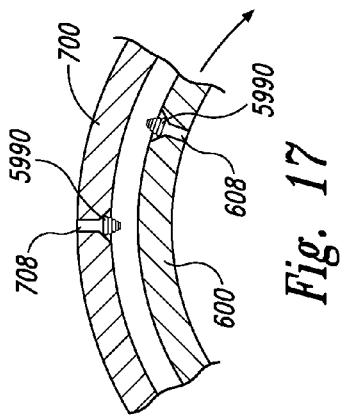
FIG. 15 is a cross-sectional view of the mixing chamber of the mixing device of FIG. 2 taken through a plane orthogonal to the axis of rotation depicting a rotary flow pattern caused by cavitation bubbles when a through-hole of the rotor approaches (but is not aligned with) an aperture of the stator.
Figure 16:
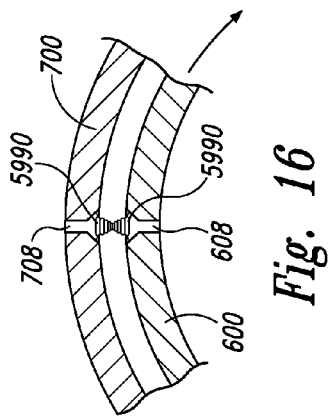
FIG. 16 is a cross-sectional view of the mixing chamber of the mixing device of FIG. 2 taken through a plane orthogonal to the axis of rotation depicting a rotary flow pattern caused by cavitation bubbles when the through-hole of the rotor is aligned with the aperture of the stator.
Figure 17:
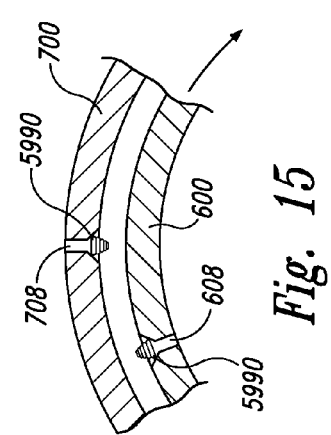
FIG. 17 is a cross-sectional view of the mixing chamber of the mixing device of FIG. 2 taken through a plane orthogonal to the axis of rotation depicting a rotary flow pattern caused by cavitation bubbles when a through-hole of the rotor that was previously aligned with the aperture of the stator is no longer aligned therewith.

Without being limited by theory, the efficiency and persistence of the diffusion of the second material 120 into the first material 110 is believed to be caused in part by micro-cavitation, which is described in connection with FIGS. 15-17. Whenever a material flows over a smooth surface, a rather laminar flow is established with a thin boundary layer that is stationary or moving very slowly because of the surface tension between the moving fluid and the stationary surface. The through-holes 608 and optionally, the apertures 708, disrupt the laminar flow and can cause localized compression and decompression of the first material 110. If the pressure during the decompression cycle is low enough, voids (cavitation bubbles) will form in the material. The cavitation bubbles generate a rotary flow pattern 5990, like a tornado, because the localized area of low pressure draws the host material and the infusion material, as shown in FIG. 15. When the cavitation bubbles implode, extremely high pressures result. As two aligned openings (e.g., one of the apertures 708 and one of the through-holes 608) pass one another, a succussion (shock wave) occurs, generating significant energy. The energy associated with cavitation and succussion mixes the first material 110 and the second material 120 together to an extremely high degree, perhaps at the molecular level.

The tangential velocity of the rotor 600 and the number of openings that pass each other per rotation may dictate the frequency at which the mixing device 100. It has been determined that operating the mixing device 100 within in the ultrasonic frequency range can be beneficial in many applications. It is believed that operating the mixing device 100 in the ultrasonic region of frequencies provides the maximum succession shock energy to shift the bonding angle of the fluid molecule, which enables it to transport an additional quantity of the second material 120 which it would not normally be able to retain. When the mixing device 100 is used as a diffuser, the frequency at which the mixing device 100 operates appears to affect the degree of diffusion, leading to much longer persistence of the second material 120 (infusion material) in the first material 110 (host material).

Figure 18:
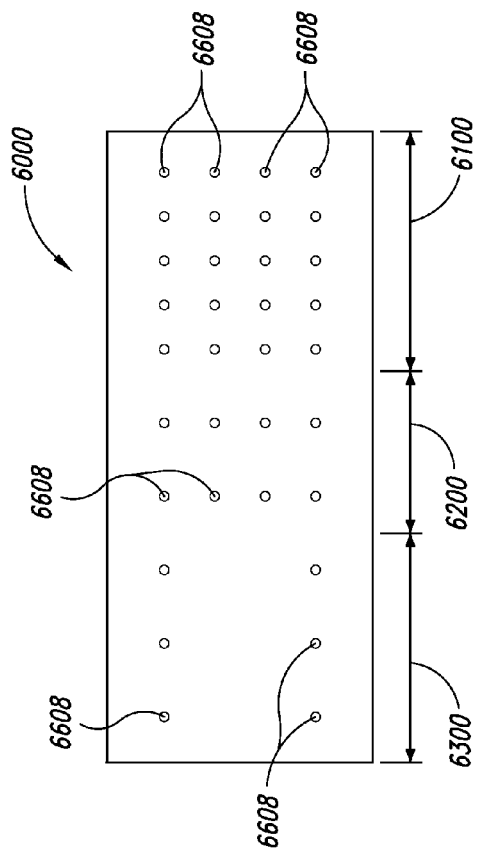
FIG. 18 is a side view of an alternate embodiment of a rotor.

Referring now to FIG. 18, an alternate embodiment of the rotor 600, rotor 6000 is provided. The cavitations created within the first material 110 in the mixing chamber 330 may be configured to occur at different frequencies along the length of the mixing chamber 330. The frequencies of the cavitations may be altered by altering the number and/or the placement of the through-holes 6608 along the length of the rotor 600. Each of the through-holes 6608 may be substantially similar to the through-holes 608 (discussed above).

By way of non-limiting example, the rotor 6000 may be subdivided into three separate exemplary sections 6100, 6200, and 6300. The through-holes 6608 increase in density from the section 6100 to the section 6200, the number of holes in the section 6100 being greater than the number of holes in the section 6200. The through-holes 6608 also increase in density from the section 6200 to the section 6300, the number of holes in the section 6200 being greater than the number of holes in the section 6300. Each of the sections 6100, 6200, and 6300 create succussions within their particular area at a different frequency due to the differing numbers of through-holes 6608 formed therein.

By manufacturing the rotor 6000 with a desired number of through-holes 6608 appropriately arranged in a particular area, the desired frequency of the succussions within the mixing chamber 330 may be determined. Similarly, the desired frequency of the cavitations may be determined by a desired number of apertures 708 appropriately arranged in a particular area upon the stator 700 within which the rotor 600 rotates. Further, the desired frequency (or frequencies) of the succussions within the mixing chamber 330 may be achieved by selecting both a particular number and arrangement of the apertures 708 formed in the stator 700 and a particular number and arrangement of the through-holes 608 formed in the rotor 600.

FIGS. 19-21, depict various alternative arrangements of the apertures 708 formed in the stator 700 and the through-holes 608 formed in the rotor 600 configured to achieve different results with respect to the cavitations created. FIG. 19 illustrates a configuration in which the apertures 708 and the through-holes 608 are aligned along an axis 7000 that is not parallel with any line (e.g., line 7010) drawn through the axis of rotation "a" of the rotor 600. In other words, if the rotor 600 has a cylindrical shape, the axis 7000 does not pass through the center of the rotor 600. Thus, the first material 110 within the mixing chamber 330 will not be oriented perpendicularly to the compressions and decompressions created by the apertures 708 and the through-holes 608. The compressions and decompressions will instead have a force vector that has at least a component parallel to the circumferential flow (in the direction of arrow "C3" of FIG. 9) of first material 110 within the mixing chamber 330.

Relative alignment of the apertures 708 and the through-holes 608 may also affect the creation of cavitations in the mixing chamber 330. FIG. 20 illustrates an embodiment in which the apertures 708 are in registration across the mixing chamber 330 with the through-holes 608. In this embodiment, rotation of the rotor 600 brings the through-holes 608 of the rotor into direct alignment with the apertures 708 of the stator 700. When in direct alignment with each other, the compressive and decompressive forces created by the apertures 708 and the through-holes 608 are directly aligned with one another.

In the embodiment depicted in FIG. 21, the apertures 708 and the through-holes 608 are offset by an offset amount "X" along the axis of rotation "α.". By way of non-limiting example, the offset amount "X" may be determined as a function of the size of the apertures 708. For example, the offset amount "X" may be approximately equal to one half of the diameter of the apertures 708. Alternatively, the offset amount "X" may be determined as a function of the size of the through-holes 608. For example, the offset amount "X" may be approximately equal to one half of the diameter of the through-holes 608. If features (e.g., recesses, projections, etc.) other than or in addition to the through-holes 608 and the apertures 708 are included in either the rotor 600 or the stator 700, the offset amount "X" may be determined as a function of the size of such features. In this manner, the compressive and decompressive forces caused by the apertures 708 of the stator 700 and the through-holes 608 of the rotor 600 collide at a slight offset causing additional rotational and torsional forces within the mixing chamber 330. These additional forces increase the mixing (e.g., diffusive action) of the second material 120 into the first material 110 within the mixing chamber 330.

Referring now to FIGS. 22-25, non-limiting examples of suitable cross-sectional shapes for the apertures 708 and the through-holes 608 are provided. The cross-sectional shape of the apertures 708 and/or the through-holes 608 may be square as illustrated in FIG. 22, circular as illustrated in FIG. 23, and the like.

Various cross-sectional shapes of apertures 708 and/or the through-holes 608 may be used to alter flow of the first material 110 as the rotor 600 rotates within the stator 700. For example, FIG. 24 depicts a teardrop cross-sectional shape having a narrow portion 7020 opposite a wide portion 7022. If the through-holes 608 have this teardrop shape, when the rotor 600 is rotated (in the direction generally indicated by the arrow "F"), the forces exerted on the first material 110, the second material 120, and optionally the third material 130 within the mixing chamber 330 increase as the materials pass from the wide portion 7022 of the teardrop to the narrow portion 7020.

Additional rotational forces can be introduced into the mixing chamber 330 by forming the apertures 708 and/or the through-holes 608 with a spiral configuration as illustrated in FIG. 25. Material that flows into and out of the apertures 708 and/or the through-holes 608 having the spiral configuration experience a rotational force induced by the spiral configuration. The examples illustrated in FIGS. 22-25 are provided as non-limiting illustrations of alternate embodiments that may be employed within the mixing device 100. By application of ordinary skill in the art, the apertures 708 and/or the through-holes 608 may be configured in numerous ways to achieve various successive and agitative forces appropriate for mixing materials within the mixing chamber 330.

Double Layer Effect

The mixing device 100 may be configured to create the output material 102 by complex and non-linear fluid dynamic interaction of the first material 110 and the second material 120 with complex, dynamic turbulence providing complex mixing that further favors electrokinetic effects (described below). The result of these electrokinetic effects may be observed within the output material 102 as charge redistributions and redox reactions, including in the form of solvated electrons that are stabilized within the output material.

Ionization or dissociation of surface groups and/or adsorption of ions from a liquid cause most solid surfaces in contact with the liquid to become charged. Referring to FIG. 26, an electrical double layer ("EDL") 7100 forms around exemplary surface 7110 in contact with a liquid 7120. In the EDL 7100, ions 7122 of one charge (in this case, negatively charged ions) adsorb to the surface 7120 and form a surface layer 7124 typically referred to as a Stern layer. The surface layer 7124 attracts counterions 7126 (in this case, positively charged ions) of the opposite charge and equal magnitude, which form a counterion layer 7128 below the surface layer 7124 typically referred to as a diffuse layer. The counterion layer 7128 is more diffusely distributed than the surface layer 7124 and sits upon a uniform and equal distribution of both ions in the bulk material 7130 below. For OH− and H+ ions in neutral water, the Gouy-Chapman model would suggest that the diffuse counterion layer extends about one micron into the water.

According to particular aspects, the electrokinetic effects mentioned above are caused by the movement of the liquid 7120 next to the charged surface 7110. Within the liquid 7120 (e.g., water, saline solution, and the like), the adsorbed ions 7122 forming the surface layer 7124 are fixed to the surface 7120 even when the liquid 7120 is in motion (for example, flowing in the direction indicated by arrow "G"); however, a shearing plane 7132 exists within the diffuse counterion layer 7128 spaced from the surface 7120. Thus, as the liquid 7120 moves, some of the diffuse counterions 7126 are transported away from the surface 7120, while the absorbed ions 7122 remain at the surface 7120. This produces a so-called 'streaming current.'

Within the mixing chamber 330, the first material 110, the second material 120, and optionally, the third material 130 are subject to an electromagnetic field created by the inside surface 705 of the stator 700 and/or the outside surface 606 of the rotor 600, a voltage between the inside surface 705 and the outside surface 606, and/or an electrokinetic effect (e.g., streaming current) caused by at least one EDL formed in the first material 110. The at least one EDL may be introduced into the first material 110 by at least one of the inside surface 705 of the stator 700 and the outside surface 606 of the rotor 600.

Movement of the first material 110 through the mixing chamber 330 relative to surface disturbances (e.g., the through-holes 608 and apertures 708) creates cavitations in the first material 110 within the mixing chamber 330, which may diffuse the second material 120 into the first material 110. These cavitations may enhance contact between of the first material 110 and/or the second material 120 with the electric double layer formed on the inside surface 705 of the stator 700 and/or the electric double layer formed on the outside surface 606 of the rotor 600. Larger surface to volume ratios of the mixing chamber, an increased dwell time of the combined materials within the mixing chamber, and further in combination with a smaller average bubble size (and hence substantially greater bubble surface area) provide for effectively imparting EDL-mediated effects to the inventive output materials.

In embodiments in which the inside surface 705 and the outside surface 606 are constructed from a metallic material, such as stainless steel, the motion of the liquid 7120 and/or the streaming current(s) facilitate redox reactions involving $H_2O$, $OH-$, $H+$, and $O_2$ at the inside surface 705 and the outside surface 606.

Referring to FIG. 27, without being limited by theory, it is believed a section 7140 of the mixing chamber 330 between the inside surface 705 and the outside surface 606 the may be modeled as a pair of parallel plates 7142 and 7144. If the first material 110 is a liquid, the first material 110 enters the section 7140 through an inlet "IN" and exits the section 7140 through an outlet "OUT." The inlet "IN" and the outlet "OUT" restrict the flow into and out of the section 7140.

Referring to FIG. 28, the area between the parallel plates 7142 and 7144 has a high surface area to volume ratio. Hence, a substantial portion of the counterion layer 7128 (and counterions 7126) may be in motion as the first material 110 moves between the plates 7142 and 7144. The number of counterions 7126 in motion may exceed the number allowed to enter the section 7140 by the inlet "IN" and the number allowed to exit the section 7140 by the outlet "OUT." The inlet "IN" and the outlet "OUT" feeding and removing the first material 110 from the section 7140, respectively, have far less surface area (and a lower surface area to volume ratio) than the parallel plates 7142 and 7144 and thereby reduce the portion of the counterions 7126 in motion in the first material 110 entering and leaving the section 7140. Therefore, entry and exit from the section 7140 increases the streaming current locally. While a background streaming current (identified by arrow "BSC") caused by the flowing first material 110 over any surface is always present inside the mixing device 100, the plates 7142 and 7144 introduce an increased "excess" streaming current (identified by arrow "ESC") within the section 7140.

Without a conductive return current (identified by arrow "RC") in the plates 7142 and 7144 in the opposite direction of the flow of the first material 110, an excess charge 7146 having the same sign as the adsorbing ions 7122 would accumulate near the inlet "IN," and an excess charge 7148 having the same sign as the counterion 7126 would accumulate near the at outlet "OUT." Because such accumulated charges 7146 and 7148, being opposite and therefore attracted to one another, cannot build up indefinitely the accumulated charges seek to join together by conductive means. If the plates 7142 and 7144 are perfectly electrically insulating, the accumulated charges 7146 and 7148 can relocate only through the first material 110 itself. When the conductive return current (identified by arrow "RC") is substantially equivalent to the excess streaming current (identified by arrow "ESC") in the section 7140, a steady-state is achieved having zero net excess streaming current, and an electrostatic potential difference between the excess charge 7146 near the inlet "IN," and the excess charge 7148 near the outlet "OUT" creating a steady-state charge separation therebetween.

The amount of charge separation, and hence the electrostatic potential difference between the excess charge 7146 near the inlet "IN," and the excess charge 7148 near the outlet "OUT," depends on additional energy per unit charge supplied by a pump (e.g., the rotor 600, the internal pump 410, and/or the external pump 210) to "push" charge against the opposing electric field (created by the charge separation) to produce the a liquid flow rate approximating a flow rate obtainable by a liquid without ions (i.e., ions 7122 and 7126).

If the plates 7142 and 7144 are insulators, the electrostatic potential difference is a direct measure of the EMF the pump (e.g., the rotor 600, the internal pump 410 and/or the external pump 210) can generate. In this case, one could measure the electrostatic potential difference using a voltmeter having a pair of leads by placing one of the leads in the first material 110 near the inlet "IN," and the other lead in the first material 110 near the outlet "OUT."

With insulating plates 7142 and 7144, any return current is purely an ion current (or flow of ions), in that the return current involves only the conduction of ions through the first material 110. If other conductive mechanisms through more conductive pathways are present between the excess charge 7146 near the inlet "IN," and the excess charge 7148 near the outlet "OUT," the return current may use those more conductive pathways. For example, conducting metal plates 7142 and 7144 may provide more conductive pathways; however, these more conductive pathways transmit only an electron current and not the ion current.

As is appreciated by those of ordinary skill, to transfer the charge carried by an ion to one or more electrons in the metal, and vise versa, one or more oxidation-reduction reactions must occur at the surface of the metal, producing reaction products. Assuming the first material 110 is water ($H_2O$) and the second material 120 is oxygen ($O_2$), a non-limiting example of a redox reaction, which would inject negative charge into the conducting plates 7142 and 7144 includes the following known half-cell reaction:

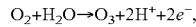

$O_2 + H_2O \rightarrow O_3 + 2H^+ + 2e^-$,

Again, assuming the first material 110 is water ($H_2O$) and the second material 120 is oxygen ($O_2$), a non-limiting example of a redox reaction includes the following known half-cell reaction, which would remove negative charge from the conducting plates 7142 and 7144 includes the following known half-cell reaction:

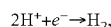

$2H^+ + e^- \rightarrow H_2$,

With conducting metal plates 7142 and 7144, most of the return current is believed to be an electron current, because the conducting plates 7142 and 7144 are more conductive than the first material 110 (provided the redox reactions are fast enough not to be a limiting factor). For the conducting metal plates 7142 and 7144, a smaller charge separation accumulates between the inlet "IN" and the outlet "OUT," and a much smaller electrostatic potential exists therebetween. However, this does not mean that the EMF is smaller.

As described above, the EMF is related to the energy per unit charge the pump provides to facilitate the flow of the first material 110 against the opposing electric field created by the charge separation. Because the electrostatic potential is smaller, the pump may supply less energy per unit charge to cause the first material 110 to flow. However, the above example redox reactions do not necessarily occur spontaneously, and thus may require a work input, which may be provided by the pump. Therefore, a portion of the EMF (that is not reflected in the smaller electrostatic potential difference) may be used to provide the energy necessary to drive the redox reactions.

In other words, the same pressure differentials provided by the pump to push against the opposing electric field created by the charge separation for the insulating plates 7142 and 7144, may be used both to "push" the charge through the conducting plates 7142 and 7144 and drive the redox reactions.

Figure 29:
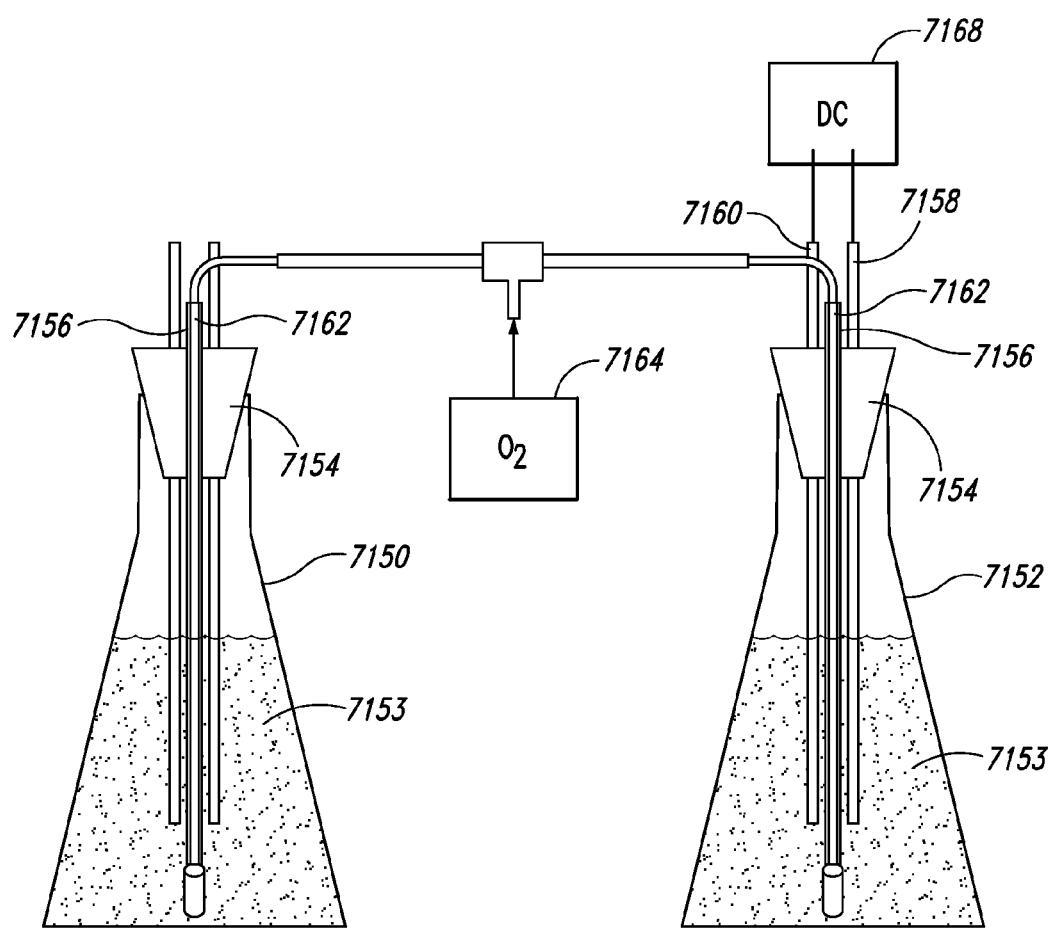
FIG. 29 is an illustration of an experimental setup.

Referring to FIG. 29, an experimental setup for an experiment conducted by the inventors is provided. The experiment included a pair of substantially identical spaced apart 500 ml standard Erlenmeyer flasks 7150 and 7152, each containing a volume of deionized water 7153. A rubber stopper 7154 was inserted in the open end of each of the flasks 7150 and 7152. The stopper 7154 included three pathways, one each for a hollow tube 7156, a positive electrode 7158, and a negative electrode 7160. With respect to each of the flasks 7150 and 7152, each of the hollow tube 7156, the positive electrode 7158, and the negative electrode 7160 all extended from outside the flask, through the stopper 7154, and into the deionized water 7153 inside the flask. The positive electrode 7158 and the negative electrode 7160 were constructed from stainless steel. The hollow tubes 7156 in both of the flasks 7150 and 7152 had an open end portion 7162 coupled to a common oxygen supply 7164. The positive electrode 7158 and the negative electrode 7160 inserted into the flask 7152 where coupled to a positive terminal and a negative terminal, respectively, of a DC power supply 7168. Exactly the same sparger was used in each flask.

Oxygen flowed through the hollow tubes 7156 into both of the flasks 7150 and 7152 at a flow rate (Feed) of about 1 SCFH to about 1.3 SCFH (combined flow rate). The voltage applied across the positive electrode 7158 and the negative electrode 7160 inserted into the flask 7152 was about 2.55 volts. This value was chosen because it is believed to be an electrochemical voltage value sufficient to affect all oxygen species. This voltage was applied continuously over three to four hours during which oxygen from the supply 7164 was bubbled into the deionized water 7153 in each of the flasks 7150 and 7152.

Testing of the deionized water 7153 in the flask 7150 with HRP and pyrogallol gave an HRP-mediated pyrogallol reaction activity, consistent with the properties of fluids produced with the alternate rotor/stator embodiments described herein. The HRP optical density was about 20% higher relative to pressure-pot or fine-bubbled solutions of equivalent oxygen content. The results of this experiment indicate that mixing inside the mixing chamber 330 involves a redox reaction. According to particular aspects, the inventive mixing chambers provide for output materials comprising added electrons that are stabilized by either oxygen-rich water structure within the inventive output solutions, or by some form of oxygen species present due to the electrical effects within the process.

Additionally, the deionized water 7153 in both of the flasks 7150 and 7152 was tested for both ozone and hydrogen peroxide employing industry standard colorimetric test ampoules with a sensitivity of 0.1 ppm for hydrogen peroxide and 0.6 ppm for ozone. There was no positive indication of either species up to the detection limits of those ampoules.

Dwell Time

Dwell time is an amount of time the first material 110, the second material 120, and optionally the third material 130 spend in the mixing chamber 330. The ratio of the length of the mixing chamber 330 to the diameter of the mixing chamber 330 may significantly affect dwell time. The greater the ratio, the longer the dwell time. As mentioned in the Background Section, the rotor 12 of the prior art device 10 (see FIG. 1) had a diameter of about 7.500 inches and a length of about 6.000 inches providing a length to diameter ratio of about 0.8. In contrast, in particular embodiments, the length of the mixing chamber 330 of the mixing device 100 is about 5 inches and the diameter "D1" of the rotor 600 is about 1.69 inches yielding a length to diameter ratio of about 2.95.

Dwell time represents the amount of time that the first material 110, the second material 120, and optionally the third material 130 are able to interact with the electrokinetic phenomena described herein. The prior art device 10 is configured to produce about 60 gallons of the output material 102 per minute and the mixing device 100 is configured to produce about 0.5 gallons of the output material 102 per minute, the prior art device 10 (see FIG. 1) had a fluid dwell time of about 0.05 seconds, whereas embodiments of the mixing device 100 have a substantially greater (about 7-times greater) dwell time of about 0.35 seconds. This longer dwell time allows the first material 110, the second material 120, and optionally the third material 130 to interact with each other and the surfaces 606 and 705 (see FIG. 7) inside the mixing chamber 330 for about 7 times longer than was possible in the prior art device 10.

With reference to Table I below, the above dwell times were calculated by first determining the flow rate for each device in gallons per second. In the case of the prior art device 10 was configured to operate at about 60 gallons of output material per minute, while the mixing device 100 is configured to operate over a broader range of flow rate, including at an optimal range of about 0.5 gallons of output material per minute. The flow rate was then converted to cubic inches per second by multiplying the flow rate in gallons per second by the number of cubic inches in a gallon (i.e., 231 cubic inches). Then, the volume (12.876 cubic inches) of the channel 32 of the prior art device 10 was divided by the flow rate of the device (231 cubic inches/second) to obtain the dwell time (in seconds) and the volume (0.673 cubic inches) of the mixing chamber 330 of the mixing device 100 was divided by the flow rate (1.925 cubic inches/second) of the device (in cubic inches per second) to obtain the dwell time (in seconds).

TABLE I

Table 1. Inventive device can accommodate a range of dwell times, including a substantially increased (e.g., 7-times) dwell time relative to prior art devices.

| Device | Flow Rate Gallons/ Minute | Flow Rate Gallons/ Second | Flow Rate Cubic Inches/ Second | Volume Mixing Chamber (Cubic Inches) | Dwell Time (Seconds) |
| --- | --- | --- | --- | --- | --- |
| Prior art device 10 | 60 | 1.000 | 231.000 | 12.876 | 0.056 |
| Mixing device 100 | 2 | 0.033 | 7.700 | 0.673 | 0.087 |
| Mixing device 100 | 0.5 | 0.008 | 1.925 | 0.673 | 0.350 |

Rate of Infusion

Figure 1:
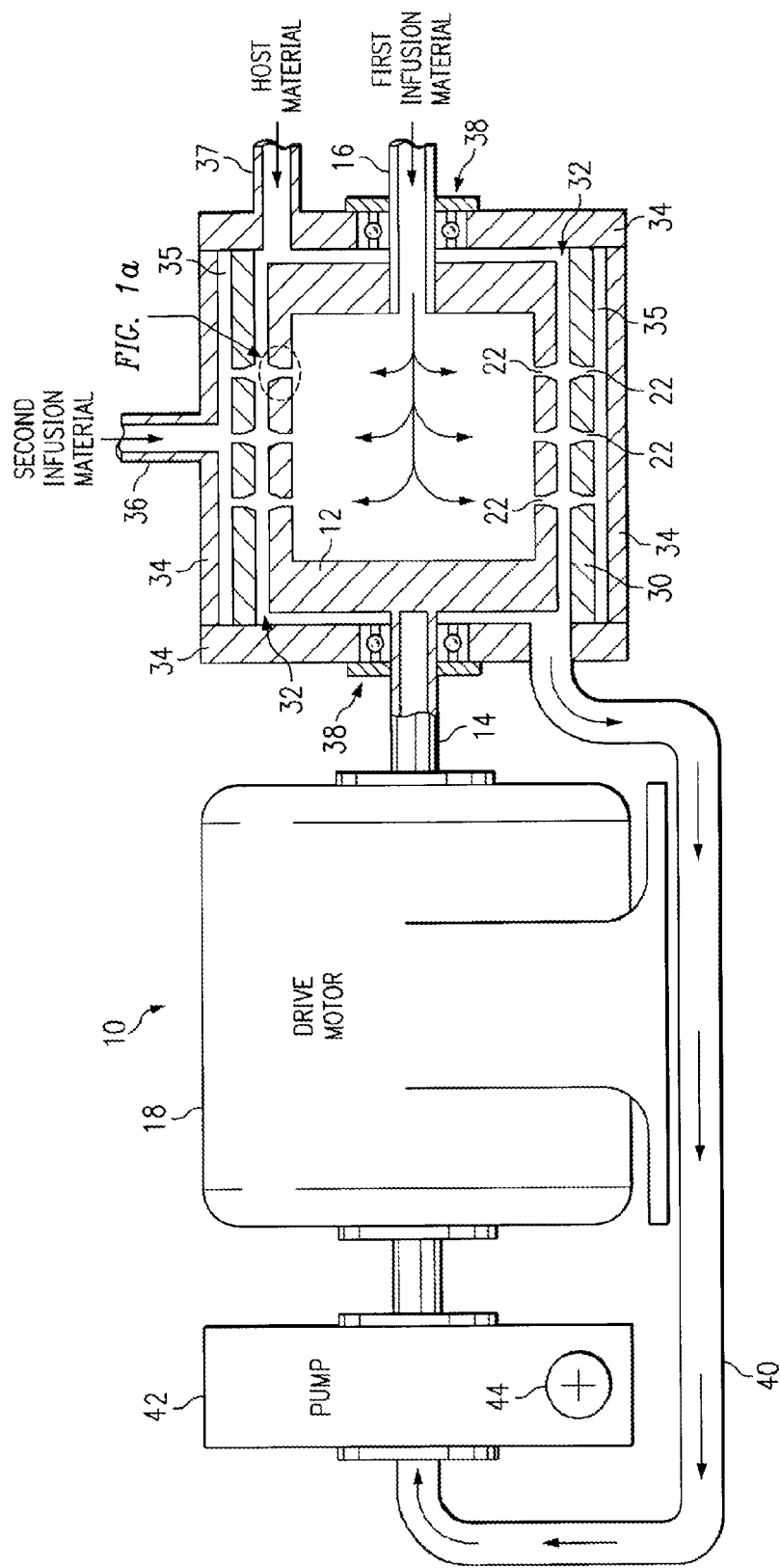
FIG. 1 is a partial cross-section, partial block diagram of a prior art mixing device.

Particular aspects of the mixing device 100 provide an improved oxygen infusion rate over the prior art, including over prior art device 10 (see FIG. 1). When the first material 110 is water and the second material 120 is oxygen, both of which are processed by the mixing device 100 in a single pass (i.e., the return block of FIG. 2 is set to "NO") at or near 20° Celsius, the output material 102 has a dissolved oxygen level of about 43.8 parts per million. In certain aspects, an output material having about 43.8 ppm dissolved oxygen is created in about 350 milliseconds via the inventive flow through the inventive non pressurized (non-pressure pot) methods. In contrast, when the first material 110 (water) and the second material 120 (oxygen) are both processed in a single pass at or near 20° Celsius by the prior art device 10, the output material had dissolved oxygen level of only 35 parts per million in a single pass of 56 milliseconds.

Output Material 102

When the first material 110 is a liquid (e.g., freshwater, saline, GATORADE®, and the like) and the second material 120 is a gas (e.g., oxygen, nitrogen, and the like), the mixing device 100 may diffuse the second material 120 into the first material 110. The following discusses results of analyses performed on the output material 102 to characterize one or more properties of the output material 102 derived from having been processed by the mixing device 100.

When the first material 110 is saline solution and the second material 120 is oxygen gas, experiments have indicated that a vast majority of oxygen bubbles produced within the saline solution are no greater than 0.1 micron in size.

Decay of Dissolved Oxygen Levels

Figure 30:
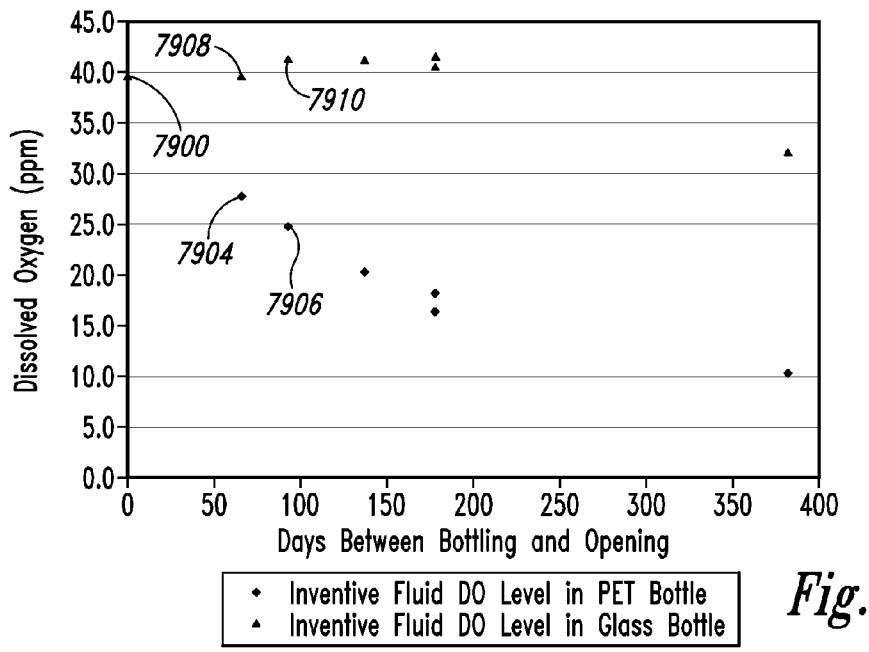
FIG. 30 illustrates dissolved oxygen levels in water processed with oxygen in the mixing device of FIG. 2 and stored a 500 ml thin walled plastic bottle and a 1,000 ml glass bottle each capped at 65° Fahrenheit.

Referring now to FIG. 30, there is illustrated the DO levels in water enriched with oxygen in the mixing device 100 and stored in a 500 ml thin-walled plastic bottle and a 1000 ml glass bottle out to at least 365 days. Each of the bottles was capped and stored at 65 degrees Fahrenheit. As can be seen in the Figure, the DO levels of the oxygen-enriched fluid remained fairly constant out to at least 365 days.

Figure 31:
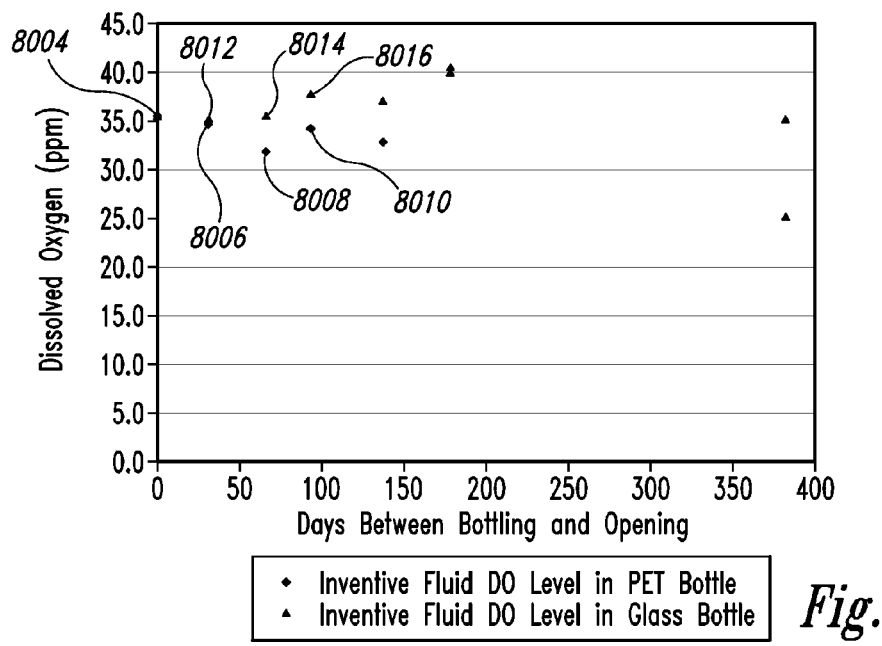
FIG. 31 illustrates dissolved oxygen levels in water processed with oxygen in the mixing device of FIG. 2 and stored in a 500 ml plastic thin walled bottle and a 1,000 ml glass bottle both refrigerated at 39° Fahrenheit.

Referring to FIG. 31, there is illustrated the DO levels in water enriched with oxygen in the mixing device 100 and stored in a 500 ml plastic thin-walled bottle and a 1000 ml glass bottle. Both bottles were refrigerated at 39 degrees Fahrenheit. Again, DO levels of the oxygen-enriched fluid remained steady and decreased only slightly out to at least 365 days.

Figure 32:
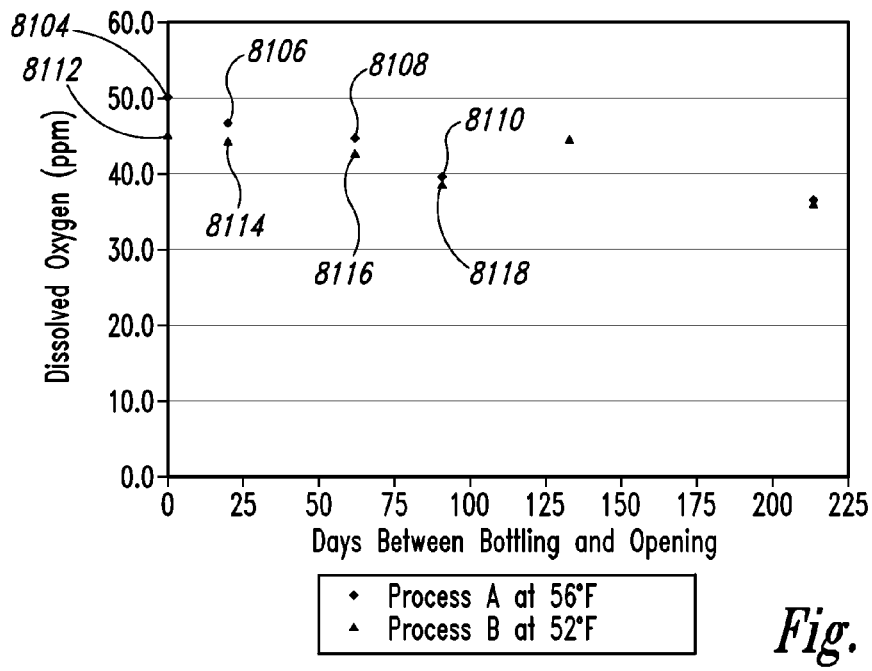
FIG. 32 illustrates the dissolved oxygen levels in GATORADE® processed with oxygen in the mixing device of FIG. 2 and stored in 32 oz. GATORADE® bottles having an average temperature of 55° Fahrenheit.

Referring now to FIG. 32, there is illustrated the dissolved oxygen levels in GATORADE® enriched with oxygen in the mixing device 100 and stored in 32 oz. GATORADE® bottles having an average temperature of 55 degrees Fahrenheit at capping. The GATORADE® bottles were subsequently refrigerated at 38 degrees Fahrenheit between capping and opening. During the experiment, a different bottle was opened at 20, 60, and 90 days, respectively, to measure the DO levels of the GATORADE® stored therein.

The GATORADE® within a first group of GATORADE® bottles was processed with oxygen in the mixing device 100 at approximately 56 degrees Fahrenheit. The DO levels of the GATORADE® at bottling were approximately 50 ppm as indicated by point 8104. A first bottle was opened at approximately 20 days, and the DO level of the GATORADE® was determined to be approximately 47 ppm as indicated by point 8106. A second bottle was then opened at 60 days, and the DO level of the GATORADE® was measured to be approximately 44 ppm as indicated by point 8108. Finally, a third bottle was opened at 90 days, and the DO level of the GATORADE® was determined to be slightly below 40 ppm as indicated by point 8110.

The GATORADE® within a second group of GATORADE® bottles was processed with oxygen in the mixing device 100 at approximately 52 degrees Fahrenheit. The initial DO level for GATORADE® stored in this group of bottles was 45 ppm as illustrated by point 8112. The GATORADE® in the bottle opened at 20 days had a DO level of only slightly lower than 45 ppm as indicated by point 8114. The second bottle of GATORADE® was opened at 60 days and the GATORADE® therein had a DO level of slightly more than 41 ppm. Finally, a third bottle of GATORADE® was opened at 90 days and the GATORADE® therein had a DO level of approximately 39 ppm as shown by point 8116. As before, with respect to the water test in the plastic and glass bottles (see FIG. 31), it can be seen that the DO levels remain at relatively high levels over the 90 day period and substantially higher than those levels present in normal (unprocessed) GATORADE® stored in 32 oz. GATORADE® bottles. Point 8010 is the level corresponding to inventive output fluid in a covered PET bottle.

Figure 33:
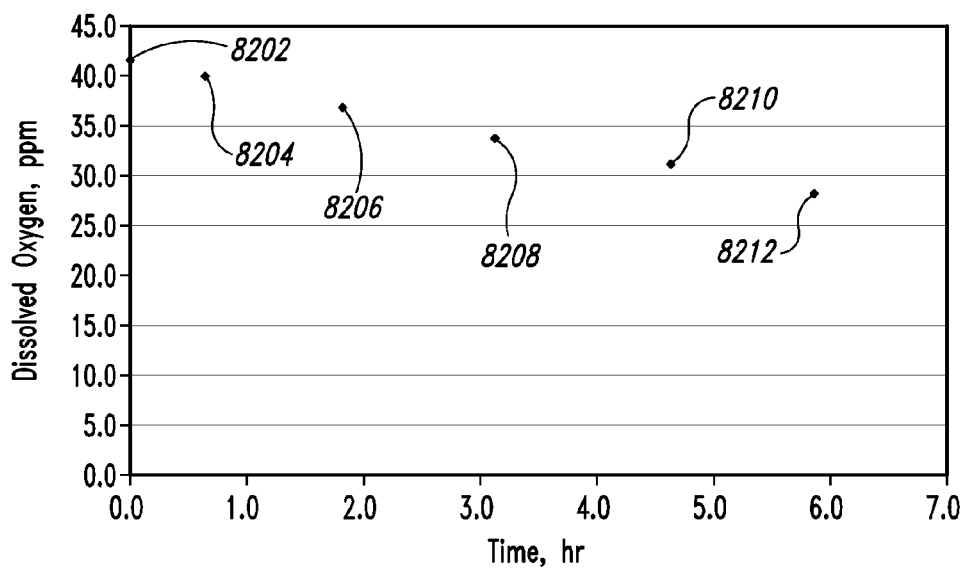
FIG. 33 illustrates the dissolved oxygen retention of a 500 ml braun balanced salt solution processed with oxygen in the mixing device of FIG. 2.

FIG. 33 illustrates the DO retention of 500 ml of braun balanced salt solution processed with oxygen in the mixing device 100 and kept at standard temperature and pressure in an amber glass bottle. The DO level of the solution before processing is 5 ppm. After processing in the mixing device 100, the DO level was increased to approximately 41 ppm (illustrated as point 8202). An hour after processing, the DO level dropped to approximately 40 ppm as indicated by point 8204. Two hours after processing, the DO level dropped to approximately 36 ppm as indicated by point 8206. The DO level dropped to approximately 34 ppm three hours after processing as indicated by point 8208. At approximately four and a half hours after processing, the DO level within the salt solution dropped to slightly more than 30 ppm. The final measurement was taken shortly before six hours after processing whereat the DO level had dropped to approximately 28 ppm. Thus, each of the experiments illustrated in FIGS. 30-33 illustrate that that the DO levels remain at relatively high levels over extended periods.

Because the output material 102 may be consumed by human beings, the materials used to construct the mixing device 100 should be suitable for food and/or pharmaceutical manufacture. By way of non-limiting example, the housing 520, the housing 5520, the rotor 600, the stator 700, and the stator 5700 may all be constructed from stainless steel.

Bubble Size Measurements

Experimentation was performed to determine a size of the bubbles of gas diffused within the fluid by the mixing device 100. While experiments were not performed to measure directly the size of the bubbles, experiments were performed that established that the bubble size of the majority of the gas bubbles within the fluid was smaller than 0.1 microns. In other words, the experiments determined a size threshold value below which the sizes of the majority of bubbles fall.

This size threshold value or size limit was established by passing the output material 102 formed by processing a fluid and a gas in the mixing device 100 through a 0.22 filter and a 0.1 micron filter. In performing these tests, a volume of the first material 110, in this case, a fluid, and a volume of the second material 120, in this case, a gas, were passed through the mixing device 100 to generate a volume of the output material 102 (i.e., a fluid having a gas diffused therein). Sixty milliliters of the output material 102 was drained into a 60 ml syringe. The DO level of the fluid was measured via the Winkler Titration. The fluid within the syringe was injected through a 0.22 micron filter into a 50 ml beaker. The filter comprised the Millipore Millex® GP50 filter. The DO level of the material in the 50 ml beaker was then measured. The experiment was performed three times to achieve the results illustrated in Table II below.

TABLE II

| DO IN SYRINGE | DO AFTER 0.22 MICRON FILTER |
|---|---|
| 42.1 ppm | 39.7 ppm |
| 43.4 ppm | 42.0 ppm |
| 43.5 ppm | 39.5 ppm |

As can be seen, the DO levels measured within the syringe and the DO levels measured within the 50 ml beaker were not changed drastically by passing the output material 102 through the 0.22 micron filter. The implication of this experiment is that the bubbles of dissolved gas within the output material 102 are not larger than 0.22 microns otherwise there would be a significantly greater reduction in the DO levels in the output material 102 passed through the 0.22 micron filter.

A second test was performed in which the 0.1 micron filter was substituted for the 0.22 micron filter. In this experiment, saline solution was processed with oxygen in the mixing device 100 and a sample of the output material 102 was collected in an unfiltered state. The DO level of the unfiltered sample was 44.7 ppm. The output material 102 was filtered using the 0.1 micron filter and two additional samples were collected. The DO level of the first sample was 43.4 ppm. The DO level of the second sample was 41.4 ppm. Then, the filter was removed and a final sample was taken from the unfiltered output material 102. The final sample had a DO level of 45.4 ppm. These results were consistent with those seen using the Millipore 0.22 micron filter. These results lead to the conclusion that there is a trivial reduction in the DO levels of the output material 102 passed through the 0.1 micron filter providing an indication that the majority of the bubbles in the processed saline solution are no greater than 0.1 micron in size.

As appreciated in the art, the double-layer (interfacial) (DL) appears on the surface of an object when it is placed into a liquid. This object, for example, might be that of a solid surface (e.g., rotor and stator surfaces), solid particles, gas bubbles, liquid droplets, or porous body. In the mixing device 100, bubble surfaces represent a significant portion of the total surface area present within the mixing chamber that may be available for electrokinetic double-layer effects. Therefore, in addition to the surface area and retention time aspects discussed elsewhere herein, the relatively small bubble sizes generated within the mixer 100 compared to prior art devices 10, may also contribute, at least to some extent, to the overall electrokinetic effects and output fluid properties disclosed herein. Specifically, in preferred embodiments, as illustrated by the mixer 100, all of the gas is being introduced via apertures on the rotor (no gas is being introduced through stator apertures. Because the rotor is rotating at a high rate (e.g., 3,400 rpm) generating substantial shear forces at and near the rotor surface, the bubble size of bubbles introduced via, and adjacent to the spinning rotor surface apertures would be expected to be substantially (e.g., 2 to 3-times smaller) smaller than those introduced via and near the stationary stator. The average bubble size of the prior art device 10 may, therefore, be substantially larger because at least half of the gas is introduced into the mixing chamber from the stationary stator apertures. Because the surface area of a sphere surface varies with $r^2$, any such bubble component of the electrokinetic surface area of the mixing device 100 may be substantially greater than that of the prior art diffusion device 10.

Therefore, without being bound by theory, not only does the mixing chamber of the mixing device 100 have (i) a substantially higher surface to volume ratio than that of the prior art device 10 (the prior art device 10 has a ratio of surface to volume of 10.9, whereas the present mixer 100 has a surface to volume ratio of 39.4), along with (ii) a 7-fold greater dwell-time, but (iii) the unique properties of the current output solutions may additionally reflect a contribution from the substantially larger bubble surface area in the mixing device 100. These distinguishing aspects reflect distinguishing features of the present mixing device 100, and likely each contribute to the unique electrokinetic properties of the inventive output materials/fluids.

Sparging Effects

Figure 34:
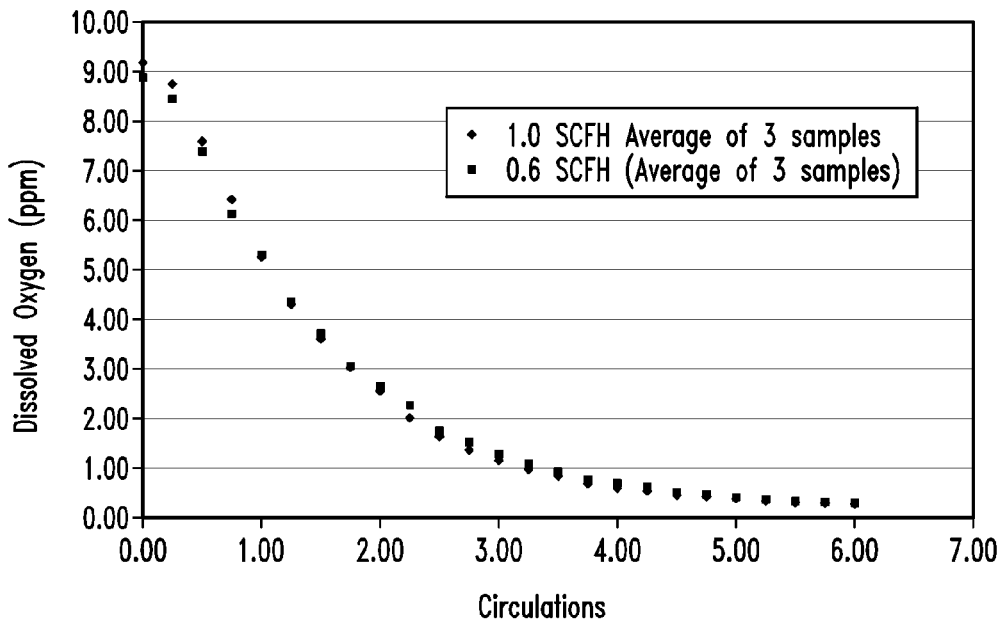
FIG. 34 illustrates a further experiment wherein the mixing device of FIG. 2 is used to sparge oxygen from water by processing the water with nitrogen in the mixing device of FIG. 2.
Figure 35:
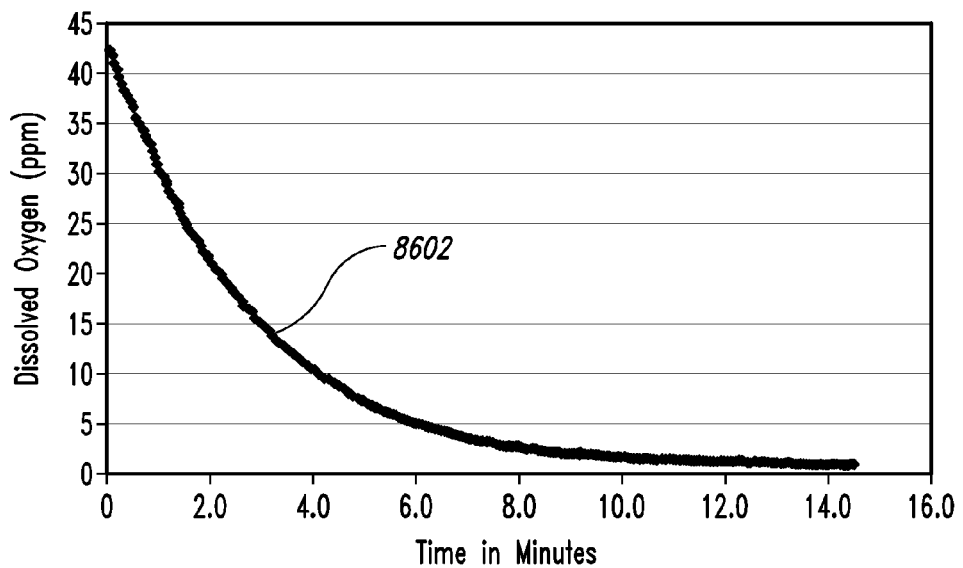
FIG. 35 illustrates the sparging of oxygen from water by the mixing device of FIG. 2 at standard temperature and pressure.

FIGS. 34-35 illustrate the sparging affects of the mixing device 100 on a fluid (e.g., the first material 110) passing therethrough. Sparging refers to "bubbling" an inert gas through a solution to remove a different dissolved gas(es) from the solution. In each of the examples illustrated in FIGS. 34 and 35, the second material 120 is nitrogen. The levels of dissolved oxygen in the output material 102 are measured at various points in time. As can be seen in the figures, the nitrogen gas sparges the oxygen from the fluid passing through the mixing device 100 causing the DO levels in the fluid to decay over a period of time.

The results of another experiment are illustrated in FIG. 34 wherein water is sparged with nitrogen using the mixing device 100. Two sets of experiments were conducted, the first having a gas flow rate of SCFH (Standard Cubic Feet per Hour) of 1 and the second having a gas flow rate of SCFH of 0.6 The fluid flow rate was about 0.5 gal/min. As can be seen, when the process is begun, the DO levels in each of the experiments was approximately 9 ppm. After only one minute, the DO levels had dropped to slightly above 5 ppm. At two minutes the DO levels had dropped to approximately 2.5 ppm. The DO level appears to level out at a minimum level at approximately 6 minutes wherein the DO level is slightly above zero (0). Thus, the nitrogen sparges the oxygen from the water relatively quickly.

FIG. 35 illustrates the sparging of oxygenated water in an 8 gallon tank at standard temperature and pressure. The decay rate of the DO in the water is illustrated by line 8602. As can be seen, initially the oxygenated water had a DO level of approximately 42 ppm. After 2 minutes of processing by the mixing device 100, the nitrogen sparged the oxygenated water such that the DO level dropped to slightly more than 20 ppm. At 6 minutes, the DO level dropped from greater than 40 ppm to only 6 ppm. The DO level of the oxygenated water reached a minimum value slightly greater than zero (0) at approximately 14 minutes after the beginning of the process. Thus, the above described sparging experiments illustrate that the mixing device 100 is capable of quickly sparging oxygen from water and replacing the oxygen with another gas such as nitrogen by processing oxygenated water with mixing device 100 for a rather short period of time. In other words, because total partial gas pressure in the fluid remained at approximately the same level despite the decrease in DO, the nitrogen gas replaced the oxygen in the fluid.

These figures illustrate the manner in which nitrogen may be diffused into water to sparge the oxygen from the water. However, any gas could be used to sparge a selected gas from any selected fluid and diffuse into the selected fluid the gas used to sparge the selected gas from the selected fluid. For example, the principals illustrated may also be applicable to sparging nitrogen from water or another fluid using oxygen. Further, any gas dissolved within a solution may be sparged therefrom using a different gas to take the place of the gas sparged from the solution. In other words, by processing a sparging gas and a solution containing a dissolved gas through the mixing device 100 for a relatively short period of time, the dissolved gas could be quickly and efficiently removed from the solution.

Molecular Interactions

A number of physicists have begun to describe the quantum properties of water. Conventionally, quantum properties are thought to belong to elementary particles of less than $10^{-10}$ meters, while the macroscopic world of our everyday life is referred to as classical, in that it behaves according to Newton's laws of motion. Between the macroscopic classical world and the microscopic quantum world is the mesoscopic domain, where the distinction between macroscopic and microscopic is becoming increasingly blurred. Indeed, physicists are discovering quantum properties in large collections of atoms and molecules in the nanometer to micrometer range, particularly when the molecules are packed closely together in a liquid phase.

Recently, chemists have made a surprising discovery that molecules form clusters that increase in size with dilution. These clusters measure several micrometers in diameter. The increase in size occurs non-linearly with dilution and depends on history, flying in the face of classical chemistry. Indeed, there is yet no explanation for this phenomena. It may well be yet another reflection of the strangeness of water that depends on its quantum properties.

In the mid 1990's, quantum physicist del Giudice and Preparata and other colleagues at the University of Milan, in Italy, argued that quantum coherent domains measuring 100 nanometers in diameter could arise in pure water. They show how the collective vibrations of water molecules in the coherent domain eventually become phase locked to the fluctuations of the global electromagnetic field. In this way, long lasting, stable oscillations could be maintained in water.

One way in which memory might be stored in water is through the excitation of long lasting coherent oscillations specific to one or more substances (such as a therapeutic agent) dissolved in the water. Interactions between the water molecules and the molecules of the substances dissolved in the water change the collective structure of the water, which would in turn determine the specific coherent oscillations that develop. If these oscillations become stabilized and maintained by phase coupling between the global field and the excited molecules, then, even when the dissolved substances are diluted away, the water may still carry the coherent oscillations that can seed other volumes of water on dilution.

The discovery that dissolved substances form increasingly large clusters is compatible with the existence of a coherent field in water that can transmit attractive resonance between molecules when the oscillations are in phase leading to clumping in dilute solutions. As a cluster of molecules increases in size, its electromagnetic signature is correspondingly amplified, reinforcing the coherent oscillations carried by the water.

One should expect changes in some physical properties in water that could be detectible. Unfortunately, all attempts to detect such coherent oscillations by usual spectroscopic and nuclear magnetic resonance methods have yielded ambiguous results. This is not surprising in view of the finding that cluster size of the dissolved molecules depends on the precise history of dilution rather than concentration of the molecules.

It is possible that despite variations in the cluster size of the dissolved molecules and detailed microscopic structure of the water, a specificity of coherent oscillations may nonetheless exist. Usual detection methods fail because they depend upon using the microscopic particles of individual molecules, or of small aggregates. Instead, what is needed is a method of detecting collective global properties over many, many molecules. Some obvious possibilities that suggest themselves are the measurements of freezing points and boiling points, viscosity, density, diffusivity, and magnet properties. One possibility for detecting changes in collective global properties of water is by means of crystallization. Crystals are formed from macroscopic collections of molecules. Like other measurements that depend on global properties, crystals simplify the subtle changes in the individual molecules that would have been undetectable otherwise.

Figure 36:
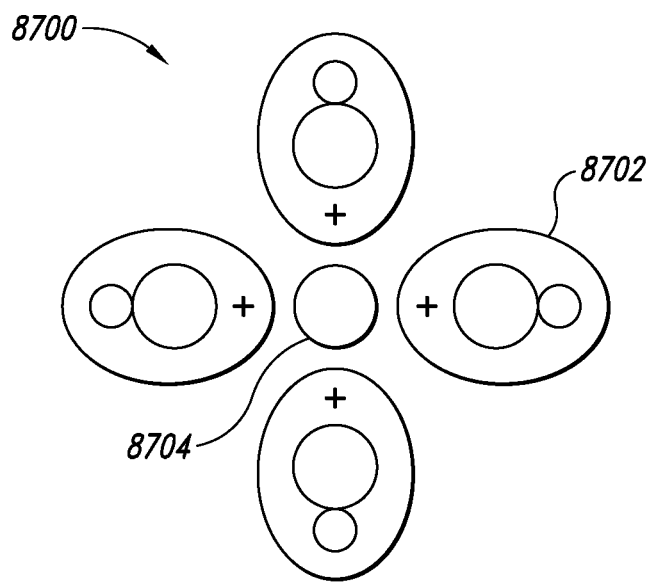
FIG. 36 is an illustration of a nanocage.
Figure 37:
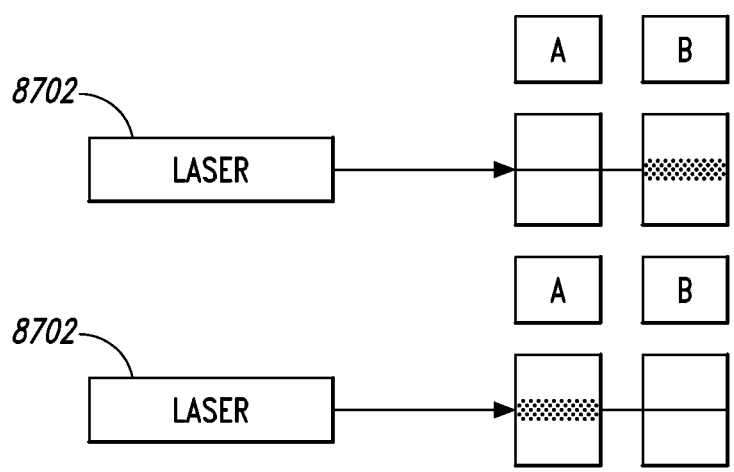
FIG. 37 illustrates the Rayleigh scattering effects produced by a sample of the water processed with oxygen by the mixing device of FIG. 2.
Figure 38:
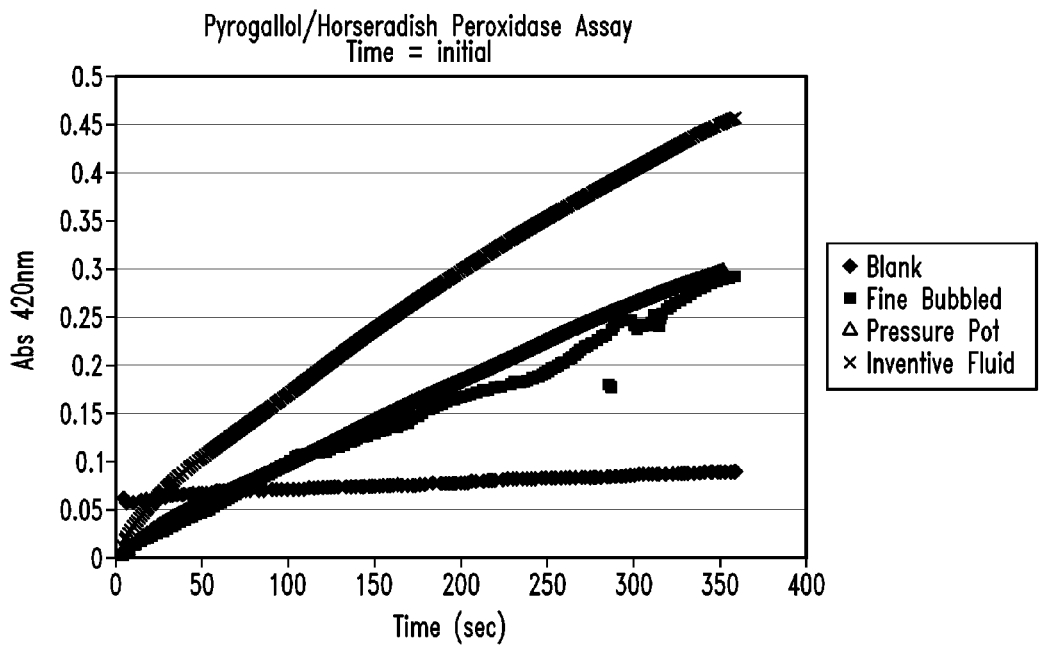
FIGS. 38-41 illustrate the inventive oxygen-enriched fluid tested positive for reactivity with horseradish peroxidase by pyrogallol, while the pressure pot and fine bubbled water samples had far less reactivity.
Figure 39:
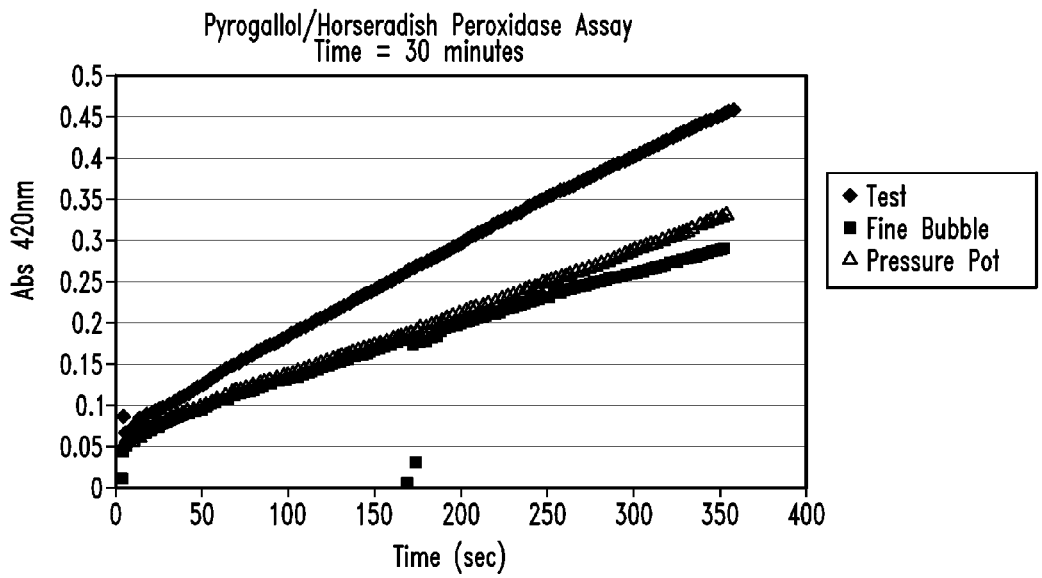
Figure 40:
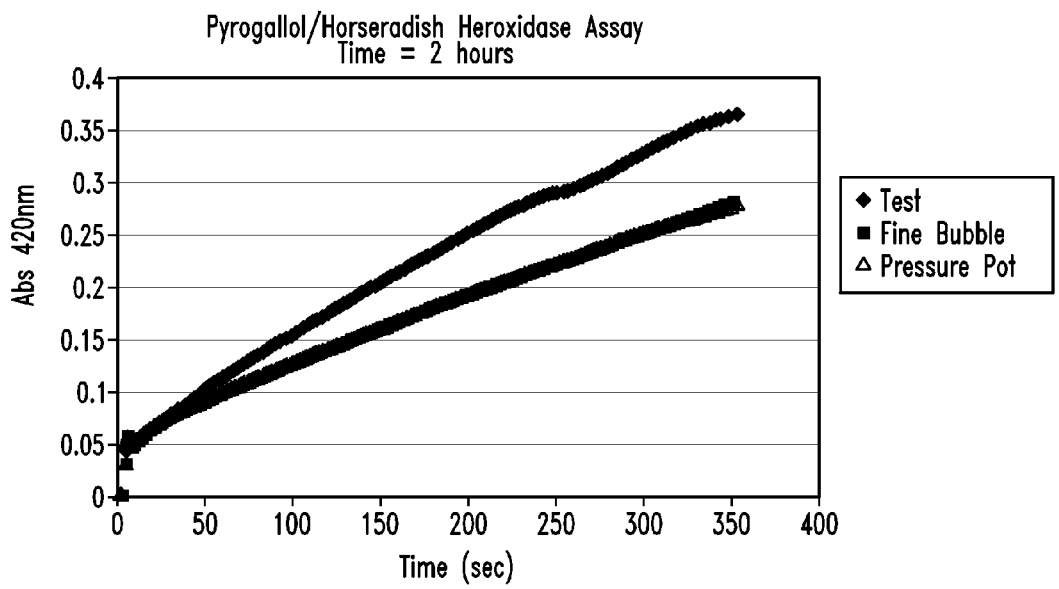
Figure 41:
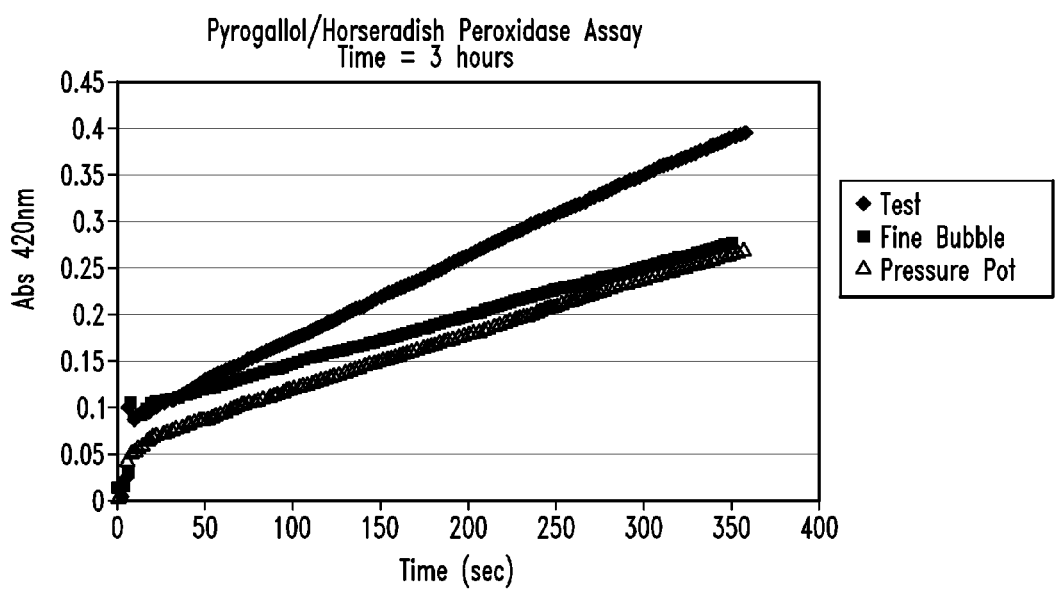

With reference to FIG. 36, a simplified protonated water cluster forming a nanoscale cage 8700 is shown. A protonated water cluster typically takes the form of $H^+(H_2O)_n$. Some protonated water clusters occur naturally, such as in the ionosphere. Without being bound by any particular theory, and according to particular aspects, other types of water clusters or structures (clusters, nanocages, etc) are possible, including structures comprising oxygen and stabilized electrons imparted to the inventive output materials. Oxygen atoms 8704 may be caught in the resulting structures 8700. The chemistry of the semi-bound nanocage allows the oxygen 8704 and/or stabilized electrons to remain dissolved for extended periods of time. Other atoms or molecules, such as medicinal compounds, can be caged for sustained delivery purposes. The specific chemistry of the solution material and dissolved compounds depend on the interactions of those materials.

Fluids processed by the mixing device 100 have been shown via experiments to exhibit different structural characteristics that are consistent with an analysis of the fluid in the context of a cluster structure.

Rayleigh Effects

If a strong beam of light is passed through a transparent gaseous or liquid medium containing solid or liquid particles, or even molecules of extremely high molecular weight, the light is scattered away from the direction of its incident path. The scattering is due to the interference effects that arise from the density fluctuations in the scattering medium (i.e. the presence of particles or very high molecular weight molecules.) There are two types of light scattering. The first involves the wavelength of the scattered light differing from that of the incident light and is called Raman scattering. The other type scattering involves when the scattered light has the same wavelength of the incident light and is called Rayleigh scattering. In Rayleigh scattering, the intensity of the scattered light is proportional to the product of the intensity of the incident light and the attenuation constant, a function of the refractive index and the Rayleigh constant. The Rayleigh constant is a somewhat involved function of the molecular weight of the scattering substance and thus a measurement of the intensity of the scattered light can give a value for the molecular weight. This scattering phenomenon is used in a number of liquid chromatography detectors.

Water processed through the mixing device 100 has been demonstrated to have detectible structural differences when compared with normal unprocessed water. For example, processed water has been shown to have more Rayleigh scattering than is observed in unprocessed water. In the experiments that were conducted, samples of processed and unprocessed water were prepared (by sealing each in a separate bottle), coded (for later identification of the processed sample and unprocessed sample), and sent to an independent testing laboratory for analysis. Only after the tests were completed were the codes interpreted to reveal which sample had been processed by the mixing device 100.

At the laboratory, the two samples were placed in a laser beam having a wavelength of 633 nanometers. The fluid had been sealed in glass bottles for approximately one week before testing. With respect to the processed sample, Sample B scattered light regardless of its position relative to the laser source. However, "Sample A" did not. After two to three hours following the opening of the bottle, the scattering effect of Sample B disappeared. These results imply the water exhibited a memory causing the water to retain its properties and dissipate over time. These results also imply the structure of the processed water is optically different from the structure of the unprocessed fluid. Finally, these results imply the optical effect is not directly related to DO levels because the DO level at the start was 45 ppm and at the end of the experiment was estimated to be approximately 32 ppm.

Generation of Solvated Electrons

Additional evidence indicates that the mixing occurring inside the mixing device 100 generates solvated electrons within the output material 102. This conclusion results from conditions observed with respect to the dissolved oxygen probe effects used in measuring the DO levels within various processed solutions. Due to the experiences viewed with respect to the polarographic dissolved oxygen probes, it is a belief that the processed fluid exhibits an electron capture effect and thus the fluid includes solvated electrons.

There are two fundamental techniques for measuring dissolved oxygen ("DO") levels electrically: galvanic measuring techniques and polarographic measurements. In both techniques, the DO level sensor includes two electrodes, an anode and a cathode, which are both immersed in electrolyte within the sensor body. An oxygen permeable membrane separates the anode and cathode from the solution being tested. The cathode is a hydrogen electrode and carries negative potential with respect to the anode. The electrolyte solution surrounds the electrode pair and is contained by the membrane. With no oxygen, the cathode becomes polarized with hydrogen and resists the flow of current. When oxygen passes through the membrane, the cathode is depolarized and electrons are consumed. In other words, oxygen diffuses across the membrane and interacts with the internal components of the probe to produce an electrical current. The cathode electrochemically reduces the oxygen to hydroxyl ions according to the following equation:

$$O_2 + 2H_2O + 4E^- = 4OH^-$$

When attempting to measure DO levels in a solution processed by the mixing device 100, an overflow condition has been repeatedly experienced wherein the dissolved oxygen meter actually displays a reading that is higher than the meter is capable of reading. Independent means, a Winkler Titration, reveals a much lower DO level for the solution than indicated by the probe. Typically, in a device such as the Orion 862, having a maximum reading of 60 ppm, the meter will overflow and have the high oxygen level indication if left in bulk processed water for several minutes.

Because the overload is not caused by dissolved oxygen in the fluid, it is believed solvated electrons must be causing the overload. In other words, solvated electrons are accompanying the processed water across the membrane. These electrons are attracted to the anode and cause the current observed. It is a further belief that these electrons are captured in a cage or cluster mechanism within the solution.

Compositions Comprising Hydrated (Solvated) Electrons Imparted to the Inventive Compositions by the Inventive Processes In certain embodiments as described herein (see under "Double-layer"), the gas-enriched fluid is generated by the disclosed electromechanical processes in which molecular oxygen is diffused into the fluid and may operate to stabilize charges (e.g., hydrated (solvated) electrons) imparted to the fluid. Without being bound by theory or mechanism, certain embodiments of the present invention relate to a oxygen-enriched fluid (output material) comprising charges (e.g., hydrated (solvated) electrons) that are added to the materials as the first material is mixed with oxygen in the inventive mixer device to provide the combined output material. According to particular aspects, these hydrated (solvated) electrons (alternately referred to herein as 'solvated electrons') are stabilized in the inventive solutions as evidenced by the persistence of assayable effects mediated by these hydrated (solvated) electrons. Certain embodiments may relate to hydrated (solvated) electrons and/or water-electron structures, clusters, etc., (See, for example, Lee and Lee, *Bull. Kor. Chem. Soc.* 2003, v. 24, 6; 802-804; 2003).

Novel HRP based assay. Horseradish peroxidase (HRP) is isolated from horseradish roots (*Amoracia rusticana*) and belongs to the ferroprotoporphyrin group (Heme group) of peroxidases. HRP readily combines with hydrogen peroxide or other hydrogen donors to oxidize the pyrogallol substrate. Additionally, as recognized in the art, HRP facilitates autoxidative degradation of indole-3-acietic acid in the absence of hydrogen peroxide (see, e.g., Heme Peroxidases, H. Brian Dunford, Wiley-VCH, 1999, Chapter 6, pages 112-123, describing that autoxidation involves a highly efficient branched-chain mechanism; incorporated herein by reference in its entirety). The HRP reaction can be measured in enzymatic activity units, in which Specific activity is expressed in terms of pyrogallol units. One pyrogallol unit will form 1.0 mg purpurogallin from pyrogallol in 20 sec at pH 6.0 at 20° C. This purpurogallin (20 sec) unit is equivalent to approx. 18 μM units per min at 25° C.

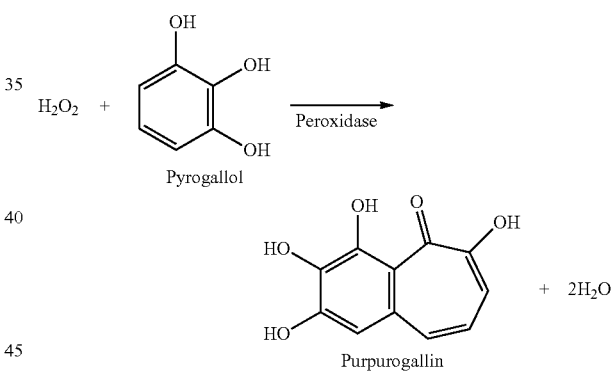

According to particular aspects of the present invention, the oxygen-enriched inventive fluids (output materials) have been described and disclosed herein to react with pyrogallol in the presence of horseradish peroxidase. The reaction is most likely based on an auto-oxidation of the pyrogallol, since no hydrogen peroxide, superoxide, or other reactive oxygen species has been detected in oxygen-enriched inventive fluid. The extent of this reaction is greater than that of pressurized oxygen solutions (pressure-pot oxygen solutions) and less than that of hydrogen peroxide.

Specifically, the present applicants have determined that while there is no hydrogen peroxide (none detected at a sensitivity of 0.1 ppm), the inventive gas-enriched fluid may be consistently characterized by its facilitation of the apparent autoxidation of pyrogallol to purpurogallin in the presence of horseradish peroxidase enzyme (HRP). That is, like the case of HRP facilitation of the autoxidative degradation of indole-3-acietic acid in the absence of hydrogen peroxide, applicants have discovered HRP facilitation of the autoxidative degradation of pyrogallol in the absence of hydrogen peroxide.

According to particular aspects, the presence and level of this activity are distinguishing features of the inventive compositions in view of the prior art.

In certain embodiments, the inventive gas-enriched fluid facilitates, in the presence of HRP and absence of hydrogen peroxide, a pyrogallol autoxidation rate (under standard conditions as defined herein under "Definitions") equivalent to approximately 0.5 ppm of hydrogen peroxide, approximately 0.8 ppm of hydrogen peroxide, approximately 1 ppm of hydrogen peroxide, approximately 2 ppm of hydrogen peroxide, approximately 3 ppm of hydrogen peroxide, approximately 4 ppm of hydrogen peroxide, approximately 5 ppm of hydrogen peroxide, approximately 6 ppm of hydrogen peroxide, approximately 7 ppm of hydrogen peroxide, approximately 8 ppm of hydrogen peroxide, approximately 9 ppm of hydrogen peroxide, approximately 10 ppm of hydrogen peroxide, approximately 11 ppm of hydrogen peroxide, approximately 12 ppm of hydrogen peroxide, approximately 20 ppm of hydrogen peroxide, approximately 40 ppm of hydrogen peroxide, approximately 50 ppm of hydrogen peroxide or any value therebetween or greater.

It is known that Horseradish peroxidase enzyme catalyzes the auto-oxidation of pyrogallol by way of facilitating reaction with the molecular oxygen in a fluid. (Khajehpour et al., PROTEINS: Struct, Funct, Genet. 53: 656-666 (2003)). It is also known that oxygen binds the heme pocket of horseradish peroxidase enzyme through a hydrophobic pore region of the enzyme (between Phe68 and Phe142), whose conformation likely determines the accessibility of oxygen to the interior. Without being bound by mechanism, because surface charges on proteins are known in the protein art to influence protein structure, it is possible that the solvated electrons present in the inventive gas-enriched fluid act to alter the conformation of the horseradish peroxidase such that greater oxygen accessibility results. The greater accessibility of oxygen to the prosthetic heme pocket of the horseradish peroxidase enzyme in turn would allow for increased reactivity with pyrogallol, when compared with prior art oxygenated fluids (pressure-pot, fine-bubbled). Alternatively, the added or solvated electrons of the present output compositions may be acting in other ways to enable facilitation of the apparent autoxidation of pyrogallol to purpurogallin in the presence of horseradish peroxidase enzyme (HRP).

In any event, according to particular aspects, production of output material using the inventive methods and devices comprises a process involving: an interfacial double layer that provides a charge gradient; movement of the materials relative to surfaces pulling charge (e.g., electrons) away from the surface by virtue of a triboelectric effect, wherein the flow of material produces a flow of solvated electrons. Moreover, according to additional aspects, and without being bound by mechanism, the orbital structure of diatomic oxygen creates charge imbalances (e.g., the two unpaired electrons affecting the hydrogen bonding of the water) in the hydrogen bonding arrangement within the fluid material (water), wherein electrons are solvated and stabilized within the imbalances.

The inventive combination of oxygen-enrichment and solvated electrons imparted by the double-layer effects and configuration of the presently claimed devices facilitates the auto-oxidation of pyrogallol in the presence of HRP, which is a distinguishing feature of the present inventive output material compositions that can be readily monitored and quantified by way of optical density. Typically, the inventive oxygen-enriched compositions are characterized in that they provide for about a 20% higher optical density read-out in the standard assay compared to either pressurized (pressure pot) or fine-bubbled control fluid have equivalent dissolved oxygen concentrations. The HRP is likely providing added oxidative ability to the autoxidation.

Pyrogallol Reactivity Test

An aliquot of the inventive oxygen-enriched output material was tested for peroxidase activity by using a commercially available horseradish peroxidase and a pyrogallol assay (Sigma). Briefly, pyrogallol stock solution was prepared with deionized water. Pyrogallol measures peroxidase activity of the horseradish peroxidase enzyme on the fluid as it reacts with a substrate (such as hydrogen peroxide), to yield purpurogallin and water. Test fluid with horseradish peroxidase, pyrogallol and the appropriate potassium phosphate buffer were compared with other fluids. Hydrogen peroxide served as the positive control. The other fluids tested were water that was oxygenated and pressurized in a pressure pot, up to 100 psi to reach the desired dissolved oxygen level (Pressure Pot), while the other fluid was oxygenated with an air stone in an open beaker (Fine Bubble). All fluids tested were maintained at room temperature, and measured approximately 55 ppm dissolved oxygen level (by FOXY probe). Water samples were tested by adding the enzymatic reagents. Continuous spectrophotometric rate determination was made at $A_{420}$ nm, and room temperature (25 degrees Celsius).

Figure 42:
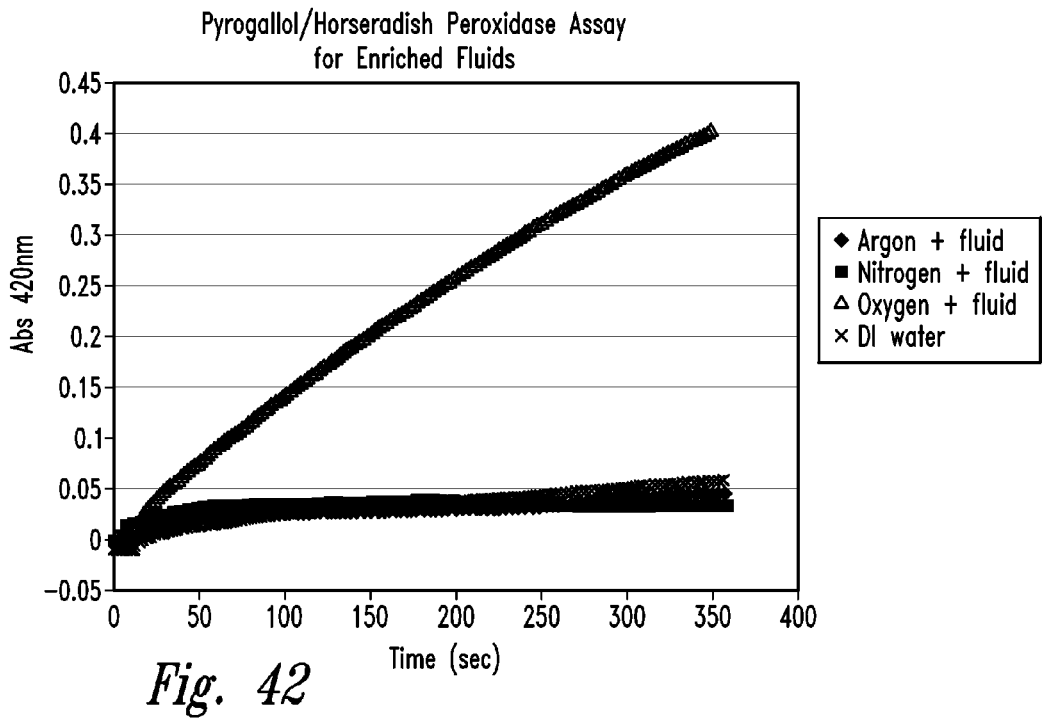
FIG. 42 illustrates pyrogallol/HRP assays as described herein, showing that oxygen is required for the reaction with pyrogallol in the presence of horseradish peroxidase, as inventive fluid enriched with other gases (argon and nitrogen) did not react in the same manner.

As indicated in FIGS. 38-41, the inventive oxygen-enriched fluid tested positive for reactivity with horseradish peroxidase by pyrogallol, while the pressure pot and fine bubbled water samples had far less reactivity. As indicated in FIG. 42, oxygen is required for the reaction with pyrogallol in the presence of horseradish peroxidase, as inventive fluid enriched with other gases did not react in the same manner.

Several chemical tests of the inventive oxygen-enriched fluid for the presence of hydrogen peroxide were conducted, as described herein, and none of these tests were positive (sensitivity of 0.1 ppm hydrogen peroxide). Thus, the inventive oxygen-enriched fluid of the instant application provides for peroxidase facilitated auto-oxidation activity in the absence of hydrogen peroxide.

In particular embodiments, Applicants have determined that the horseradish peroxidase effect remains at least up to seven hours after opening of the bottle in which it is stored. In other embodiments, Applicants have determined that the horseradish peroxidase effect remains after opening of closed container after 105 days of storage in the closed container. By contrast, in other embodiments, Applicants have determined that when testing equivalent dissolved oxygen levels made with just pressurizing fluid (pressure pot fluids), the decline of a background HRP effect takes place rapidly, declining precipitously in under 4 hours.

Glutathione Peroxidase Study

Figure 43:
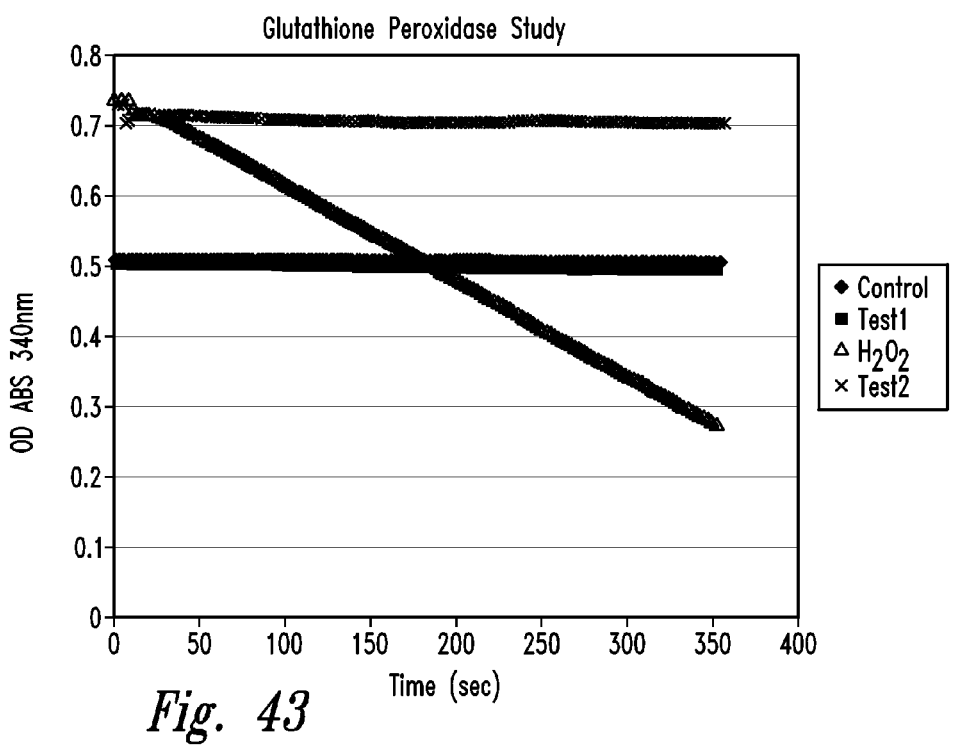
FIG. 43 illustrates the hydrogen peroxide positive control showed a strong reactivity, while none of the other fluids tested reacted with the glutathione.

The inventive oxygen-enriched output fluid material was tested for the presence of hydrogen peroxide by testing the reactivity with glutathione peroxidase using a standard assay (Sigma). Briefly, glutathione peroxidase enzyme cocktail was constituted in deionized water and the appropriate buffers. Water samples were tested by adding the enzymatic reagents. Continuous spectrophotometric rate determination was made at $A_{340}$ nm, and room temperature (25 degrees Celsius). Samples tested were: 1. deionized water (negative control), 2. inventive oxygen-enriched fluid at low concentration, 3. inventive oxygen-enriched fluid at high concentration, 4. hydrogen peroxide (positive control). As illustrated in FIG. 43, the hydrogen peroxide positive control showed a strong reactivity, while none of the other fluids tested reacted with the glutathione peroxidase.

Differential Nucleic Acid Stability

Figure 44:
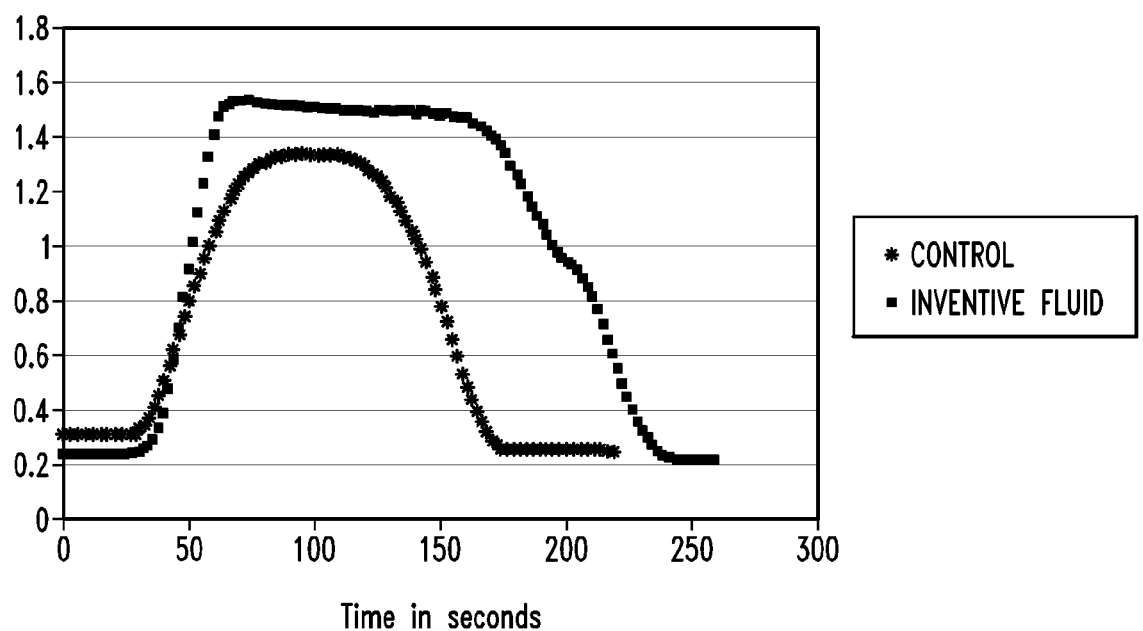
FIG. 44 illustrates T7 DNA shows a conformational change at about 50 degrees Celsius in the control (deionized water), whereas the DNA in the oxygen-enriched inventive fluid remains intact until about 60 degrees Celsius.

Particular embodiments of the present invention provide another distinguishing feature of the present inventive compositions. Specifically, applicants have discovered that there is a differential thermostability of nucleic acids associated with the inventive output fluids compared to control fluids. For example, the T7 promoter primer 5'-d(TAATACGACT-CACTATAGGG)-3' (SEQ ID NO:1) when measured in the inventive oxygen-enriched output materials relative to non-enriched deionized water. As the temperature of the water increases, the DNA oligomeric structure performs a conformational change. As illustrated in FIG. 44, consent with the art recognized melting temperature for this oligo of about 48° C., the T7 DNA begins to denature at about 50 degrees Celsius in the control (deionized water), whereas the DNA in the oxygen-enriched inventive fluid remains intact until about 60 degrees Celsius. Thus, the inventive oxygen-enriched fluid comprising solvated electrons imparts a higher thermostability for DNA when compared to control fluid, and provides a further distinguishing feature of the present inventive output material compositions that can be readily monitored and quantified by way of optical density measurements.

Bioreactor Systems Comprising the Inventive Mixing Devices

Producing significant quantities of target products, such as proteins, polypeptides, nucleic acids, therapeutic agents, and other products in host cell systems are possible due to advances in molecular biology. For example, recombinant proteins are produced in a host cell systems by transfecting the host cell with nucleic acids (e.g. DNA) encoding a protein of interest. Next, the host cell is grown under conditions which allow for expression of the recombinant protein. Certain host cell systems can be used to produce large quantities of recombinant proteins which would be too impractical to produce by other means.

In addition, enzymatic and/or reaction fermentations, with or without host cells, are utilized for example in producing foodstuff and beverages, in treating wastewater, or in environmental cleanup.

Cell culturing processes, or cellular fermentation, typically use prokaryotic or eukaryotic host cells to produce recombinant proteins. The fermentation is typically conducted in physical containers (e.g. stirred tanks) called fermentors or tank bioreactors. The fermentation process itself may comprise (1) discontinuous operation (batch process), (2) continuous operation, or (3) semi-continuous operations (such as the fed-batch process), or any combination of these.

Since the aim of large scale production of pharmaceutical drugs (e.g. biologicals) or other target products is to provide improved manufacturing processes and reduced costs, there is a need for improved bioreactor equipment, methods, and media for preparation of these target products.

The present disclosure sets forth novel gas-enriched fluids, including, but not limited to gas-enriched water, saline solutions (e.g., standard aqueous saline solutions), cell culture media, as well as novel methods and biological and chemical reactor systems for use in these application processes, and others.

Certain embodiments disclosed herein relate to systems, media, and methods for producing a target product, such as a protein.

In certain embodiments, a target product may refer to a protein, peptide, polypeptide, nucleic acid, carbohydrate, polymer, micelle, and any mixture thereof.

The target product is typically produced by a vehicle, such as a host cell, which is associated with the gas-enriched fluid in a chemical or biological reactor. Reactors may include standard reactors, such as continuous feed, discontinuous feed, and/or semi-continuous feed. Reactors may also include a cell culture vessel (such as a plate, flask, or tank), a plant, an animal, a fungus, an alga, or other organism. For example, a plant that is associated with the gas-enriched fluid of the present invention may comprise plant cells acting as vehicles that aid in the production of the target product (for example, naturally occurring plant matter or genetically altered plant matter).

In certain embodiments, the vehicles utilized with the gas-enriched fluids or solutions (including media) may include prokaryotic cells or eukaryotic cells. More specifically, the living cells may include bacterial (e.g. *E. coli, Salmonella, Streptococcus, Staphylococcus, Neisseria, Nocardia, Mycoplasma*, etc.), fungal (e.g. yeasts, molds, mushrooms, etc.), plant (tobacco, maize, soybean, fruit or vegetable, etc.), animal (mammalian, insect, etc.) archebacterial (blue green algae), protist, human embryonic kidney (HEK) cells, HeLa cells, hybridoma cells, Madin-Darby Canine Kidney (MDCK) cells, stem cells, cell lines (including SP2/0 and NSO), African Green Monkey Kidney (Vero) cells, *Spodoptera frugiperda* (army worm), *Trichoplusia ni* (cabbage looper), and other cells. In addition, viruses (such as bacteriophage, baculovirus, vaccinia, and other viruses) may be employed in the bioreactors of the present invention.

The bioreactor may comprise an airlift reactor, a packed bed reactor, a fibrous bed reactor, a membrane reactor, a two-chamber reactor, a stirred-tank reactor, a hollow-fiber reactor, or other reactor designed to support suspended or immobilized cell growth.

In cases of recombinant or target protein production, a balanced batch and/or feed medium must encourage optimal cell growth and expression of the recombinant protein. The medium, or media, is termed "minimal" if it only contains the nutrients essential for growth. For prokaryotic host cells, the minimal media typically includes a source of carbon, nitrogen, phosphorus, magnesium, and trace amounts of iron and calcium. (Gunsalus and Stanter, The Bacteria, V. 1, Ch. 1 Acad. Press Inc., N.Y. (1960)). Most minimal media use glucose as a carbon source, ammonia as a nitrogen source, and orthophosphate (e.g. $PO_4$) as the phosphorus source. The media components can be varied or supplemented according to the specific prokaryotic organism(s) grown, in order to encourage optimal growth without inhibiting target protein production. (Thompson et al., *Biotech. and Bioeng.* 27: 818-824 (1985)). This allows for higher levels of production with lower cost.

In addition to the chemical composition of the media, other factors may affect cell growth and/or target protein production. These factors include, but are not limited to pH, time, cultivation temperature, amount of dissolved oxygen or other gas(es), and partial pressure of those dissolved gasses. During the fermentation process, the pH of the media is typically altered due to the consumption of ammonia, or microorganism synthesis of certain metabolic products, e.g., acetic acid and lactic acid. Since altered pH may be unfavorable for optimal cell growth, it may be necessary or desirable to maintain the medium at a certain pH (i.e. by addition of acids or bases). The pH and other process parameters can be monitored manually or by automatic devices.

Inventive Gas-Enriched Fluids

Enriching a fluid with another fluid may result in a solution or suspension of the two fluids, depending on the physical and chemical properties of the two fluids. In particular, enriching a liquid with a gas (e.g. oxygen) may be beneficial for certain applications, including therapeutic treatments. As utilized herein, "fluid," may generally refer to a liquid, a gas, a vapor, a mixture of liquids and/or gases, a liquid and/or gas solution, or any combination thereof, for any particular disclosed embodiment. Furthermore, in certain embodiments a "liquid" may generally refer to a pure liquid or may refer to a gel, sol, emulsion, fluid, colloid, dispersion, suspension, or mixture, as well as any combination thereof; any of which may vary in viscosity.

In particular embodiments, the dissolved gas comprises oxygen. In other particular embodiments, the dissolved gas comprises nitrogen, carbon dioxide, carbon monoxide, ozone, sulfur gas, nitrous oxide, nitric oxide, argon, liquefied petroleum gas, helium, natural gas, or others.

One particular advantage of embodiments of the present invention relates to the gas-enriched fluids' long-term diffused gas (particularly oxygen) levels, which allows for long-term bio-availability of the gas to cellular or chemical reactors. The long-term bio-availability of gasses in the gas-enriched fluids of the present invention allow for increased target product production and/or improved enzymatic or other chemical reactions that benefit from the gas-enriched fluids (including oxygenated media) of the present invention.

In some instances, living cells may be grown in a bioreactor or fermentation chamber in order to promote cell growth and/or production of the intended target product. While some living cells require a mixture of gasses in order to sustain or promote their survival or propagation, cell growth may be hindered or ceased if a particular gas, such as oxygen, is present at too high of a concentration.

For example, mammalian cells, such as Chinese Hamster Ovary (CHO) cells, require oxygen in order to proliferate. However, the existing techniques in the art for diffusing gasses, such as oxygen, into the bioreactor fluids have a detrimental effect on mammalian cell cultures. For example, the cells may be destroyed or rendered non-viable in instances where the diffused gas bubbles rupture or coalesce within the culture media, which is particularly common at a gas-to-liquid interface. Accordingly, the present invention represents an advance that would not have occurred in the ordinary course since the existing knowledge in the art teaches that the levels of dissolved gas, particularly the levels of dissolved oxygen, in the gas-enriched media disclosed herein is predicted to be harmful or detrimental. However, the gas-enriched fluid media as described herein result in imparting at least one beneficial advantage to cell cultures selected from the group consisting of: enhanced cell growth (e.g. rate and/or number) increased target product yield (e.g. amount), increased rate of target product production, improved vehicle cell viability, increased efficiency of target product production, increased ease in target product purification, and the like. In certain embodiments, one or more of these beneficial advantages are conveyed to cell cultures without proving injurious to the cells themselves.

In other embodiments, an acellular reaction may utilize the gas-enriched fluids and methods of the present invention, including general chemical and/or enzymatic reactions. Examples of such reactions include, but are not limited to, wastewater treatment, purification of water (such as treating municipal water, home drinking purifiers, cleaning swimming pools or aquariums, etc.), homogenization of milk, hydrogenation of oils, gas-enriching fuels, and others.

In further embodiments, the gas-enriched fluid maintains a dissolved gas enrichment level of at least 10 ppm, at least 15 ppm, at least 20 ppm, at least 25 ppm, at least 30 ppm, at least 35 ppm, at least 40 ppm, at least 45 ppm, at least 50 ppm, at least 55 ppm, at least 60 ppm, at least 65 ppm, at least 70 ppm, at least 75 ppm, at least 80 ppm, at least 85 ppm, at least 90 ppm, at least 100 ppm, or any value greater or therebetween, at atmospheric pressure. In certain instances, the gas-enriched fluid maintains its dissolved gas enrichment level (i.e. the level of the gas enriched in the fluid) for a period of at least 10 days, at least 20 days, at least 30 days, at least 40 days, at least 50 days, at least 60 days, at least 70 days, at least 80 days, at least 90 days, at least 100 days, at least 110 days, at least 120 days, at least 130 days, or greater or any value therebetween, within a sealed container at atmospheric pressure.

In one particular embodiment, the host material comprises water or water vapor. In another particular embodiment, the host material comprises other fluids (i.e. gasses or liquids) such as wastewater, toxic materials, potable water, milk, juice, yogurt, soft drinks (particularly carbonated beverages), ethanol, methanol, polymers (such as plastic or rubber compounds), oil (edible or non-edible), emulsions, suspensions, aqueous carriers, non-aqueous carriers, and the like.

In certain embodiments, multiple gasses may be used to enrich or infuse a host fluid. In certain embodiments, ozone and/or oxygen may be used to break down complex structures into smaller substructures, particularly if used with sonochemistry techniques, as described herein inter alia.

In certain embodiments, the gas-enriched fluid or other host material of the present invention has characteristics that may be more similar to the gas that has enriched the fluid or other host material, or it may have characteristics that are more similar to the fluid (e.g. gas or liquid) or other host material itself.

In certain embodiments, a gas-enriched fluid or solution comprises gas-enriched culture media. In particular embodiments, the gas-enriched media comprises oxygenated or oxygen-enriched media. In certain embodiments, the gas-enriched fluid or gas-enriched host material may include further processing, such as by filtering, separating, modifying or altering various constituents of the fluid or host material.

Packaged Gas-Enriched Fluids

Certain embodiments disclosed herein relate to gas-enriched fluids that have high levels of dissolved or diffused gases (particularly oxygen) that may be produced by various methods, including those described herein. In certain embodiments, the gas-enriched fluid may be produced in a biomass production facility and applied directly to a bioreactor system. Alternatively, the gas-enriched fluid may be packaged and distributed for use at other locations. In the event that the gas-enriched fluid is packaged, such packaging may include a sterile package such as a glass or plastic container, flexible foil or plastic pouches, sealed boxes (particularly waxed boxes), and the like. In the case of sealed packages, the gas-enriched fluid may maintain a high level of dissolved or diffused gas for several days, several weeks, or several months. In certain embodiments, the sealed container (i.e. enclosed with a cap, cover or other enclosure that is at least semi-impermeable to gas exchange) maintains the diffused nature of the fluid at least 2 weeks, at least 4 weeks, at least 2 months, at least 4 months, at least 6 months, at least 8 months, at least 10 months, at least 12 months, or any value greater or therebetween.

Gas-Enriched Fluids in Biological or Chemical Reactors

Figure 45A:
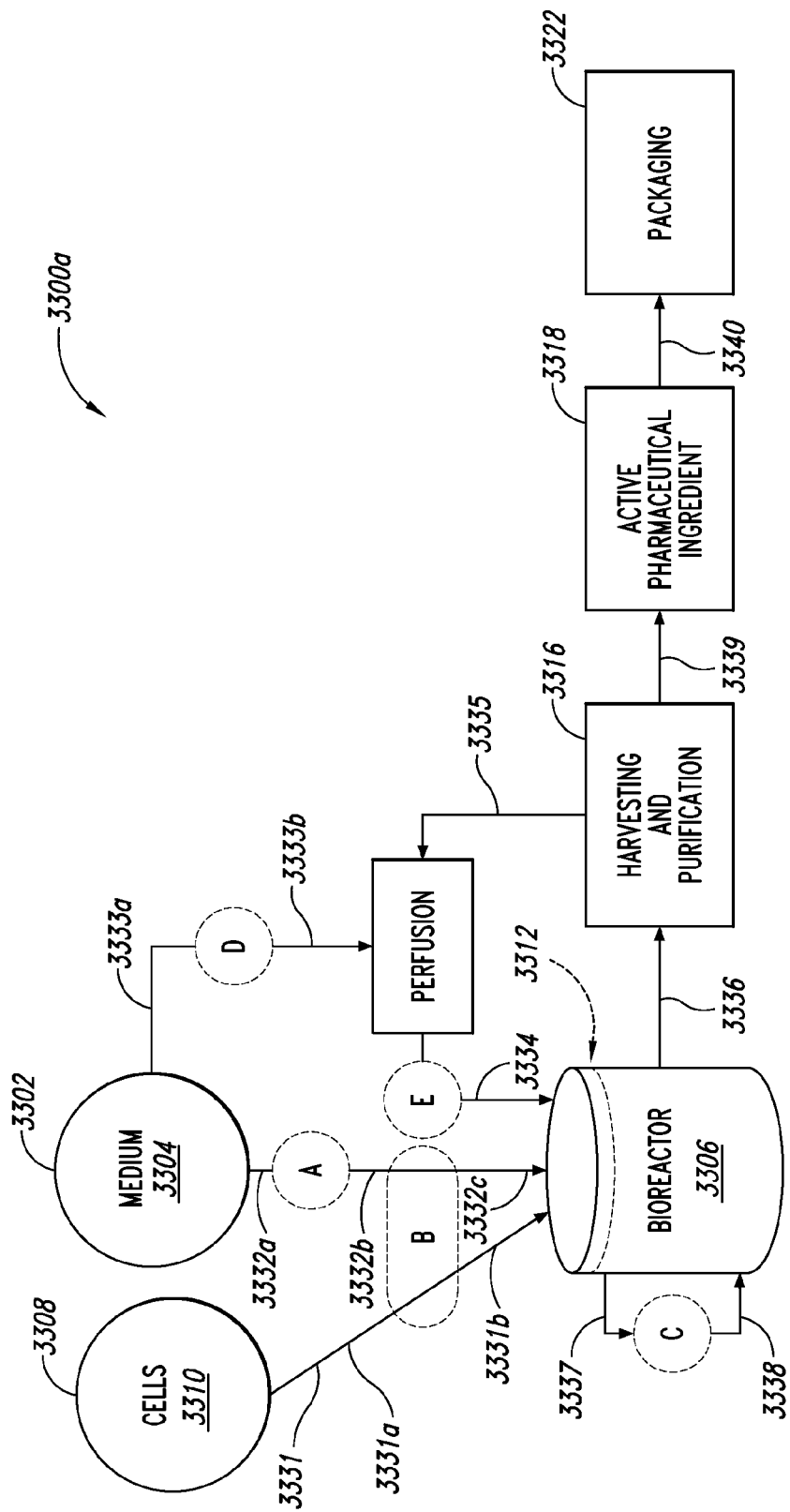
Figure 45B:
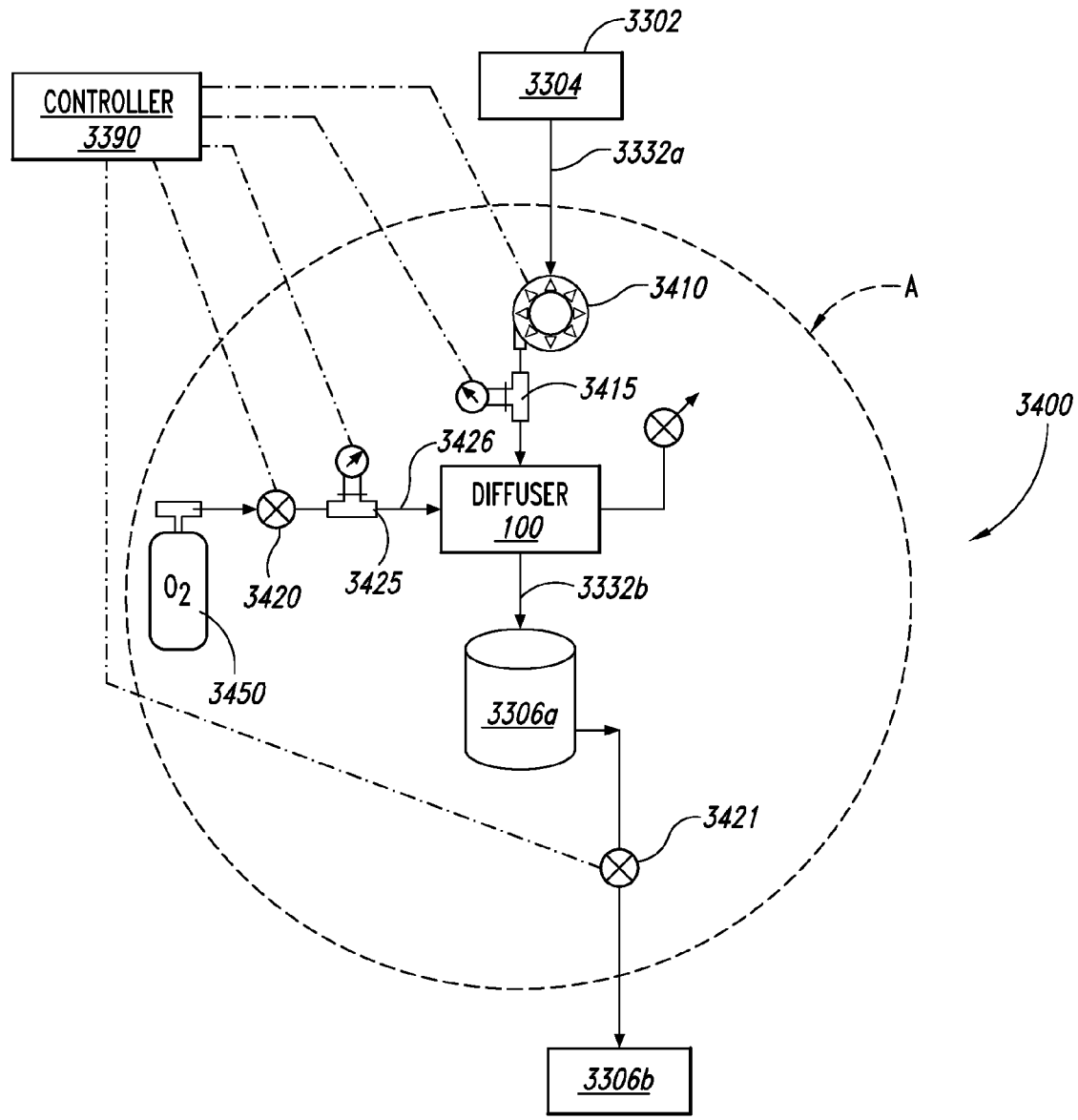

As illustrated in FIGS. 45A and 45B, a biological or chemical reactor system 3300a may be used for conventional large-scale cell-culturing or chemical processing to achieve the production of the target product 3318. The target product 3318 may include, but not be limited to, proteins, antibodies, synthetic peptides, active pharmaceutical agents, foodstuff or beverage products (such as wine; beer; soft drinks; fruit or vegetable juices); plant products (flowers, cotton, tobacco, wood, paper, wood or paper pulp, etc.); ethanol, methanol, paints, fruit or vegetables or fruit or vegetable products such as jellies, jams, sauces, pastes, and the like; cheese or cheese products; nuts or nut products (such as peanut butter, almond paste, etc.); meat or meat products, grain flours or products including bread, cereal, pasta, and the like; slurries or mixtures of any of these, processed polymers (including plastics, and other polymers), petroleum products, and others.

In certain embodiments, in the case of using a vessel reactor, such as a tank reactor, the target product resides within inclusion bodies, particularly when *E. coli* cells are utilized. The target product may be obtained by processing the inclusion bodies, for example by using high-pressure homogenizers or other techniques.

In particular embodiments in which the reactor is a biological reactor system, the system 3306 includes a source 3308 of culture cells 3310 to be cultured, a source 3302 of culture media 3304, a biological reactor 3306, and a harvesting and purification system 3316, for producing the target product 3318. The culture cells 3310 are genetically predetermined to produce proteins or the like that constitute the target product 3318, and the culture medium 3304 may comprise a sterile medium of a type that provides nourishment for the proliferation of culture cells 3310. In this particular exemplary embodiment, the sterile medium 3304 is introduced into the internal chamber (which may be referred to as the "fermentation chamber") of the reactor 3306 from the source 3302. From the source 3308, the culture cells 3310 are provided such that the cells 3310 and medium 3304 are combined into a broth 3312 in the fermentation chamber of the bioreactor 3306.

The appropriate base medium 3304 to be utilized in the reactor system 3300a may be formulated to provide optimal nourishment and growth to the cell culture 3310. Medium 3304 is preferably a fluid (e.g. liquid or gas) medium, more preferably a liquid medium or a solid-liquid medium that is selected based on the certain variables, such as the characteristics and objectives of the overall bioreactor system 3300a, the cost, the type of cells being cultured from the cell culture 3310, the desired production parameters, the type of culturing and media management process used in the reactor 3306, the type of downstream harvest and purification processes 3316, and the target active pharmaceutical ingredient 3318. Various cell culture media presently used may be adapted for use or gas-enrichment by the present invention.

In certain embodiments, a suitable base medium 3304 may include but not be limited to a serum-supplemented medium, a hydrolysate medium, chemically-synthesized medium, chemically-defined medium, a serum-free medium, any combination of these or other media.

In certain embodiments, the gas-enriched media may be supplemented with transferrins, albumins, fetuins, protein hydrolysates, or other additives, preservatives, nutrients, fillers, shear protectants (such as Pluronic F68), or active or inactive agents.

In addition, the medium may be formulated for cells that are attached to some type of support within the bioreactor 3306, rather than suspended in the broth 3312. In all embodiments that utilize a medium 3304, the medium 3304 is formulated to meet the nutritional requirements of the individual cell type in the cell culture 3310, and typically comprise minerals, salts, and sugars.

In certain embodiments, medium 3304 and/or broth 3312 are gas-enriched using the presently disclosed mixing devices 100, in order to dissolve or diffuse gases (such as oxygen) into, for example, the media, both or components thereof, in concentrations of at least about 8 ppm, at least about 10 ppm, at least about 20 ppm, at least about 25 ppm, at least about 30 ppm, at least about 35 ppm, at least about 40 ppm, at least about 50 ppm, at least about 60 ppm, at least about 70 ppm, at least about 80 ppm, at least about 90 ppm, at least about 100 ppm, or any value greater or therebetween. In certain embodiments, the gas-enriched medium and/or broth contains less than about 160 ppm.

In certain embodiments, the typical biological or chemical reactor is loaded with sterilized raw materials (nutrients, reactants, etc.) along with air or specific gas, as well as cells for a biological reactor. Other agents may be added to the mixture, including anti-foaming chemicals or agents, pH controlling agents, and/or other agents. The target product is typically recovered by separating the cells, and/or disrupting the cells in order to extract the product, concentrating the product, and purifying, drying, or further processing the product.

Many different types of bioreactor systems are in use today, any of which can be used with the gas-enriched media of the present invention. For example, air-lift bioreactors are commonly used with bacteria, yeast and other fungi; fluidized-bed bioreactors are commonly used with immobilized bacteria, yeast and other fungi, as well as activated sludge; microcarrier bioreactors are commonly used with mammalian cells immobilized on solid particles; surface tissue propagators are commonly used with mammalian cells, tissue grown on solid surfaces, and tissue engineering; membrane bioreactors, hollow fibers and roto-fermentors are typically used with bacteria, yeast, mammalian cells, and plant cells; modified stir-tank bioreactors are commonly used with immobilized bacteria, yeast, and plant cells; modified packed-bed bioreactors are commonly used with immobilized bacteria, yeast, and other fungi; tower and loop bioreactors are commonly used with bacteria and yeast; vacuum and cyclone bioreactors are commonly used with bacteria, yeast, and fungi; and photochemical bioreactors are commonly used with photosynthetic bacteria, algae, cyanobacteria, plant cell culture, and/or DNA plant cells.

Since living cells, including bacteria, yeast, plant cells, mammalian cells, and fungal cells require molecular oxygen as an electron acceptor in the bioxidation of substrates (such as sugars, fats, and proteins), cell culture media that is highly oxygenated is beneficial to the living cells. In a standard oxidation-reduction reaction, glucose is oxidized to make carbon dioxide, while oxygen is reduced to make water. Molecular oxygen accepts all of the electrons released from the substrates during aerobic metabolism. Thus, in order to provide the maximum amount of bio-available oxygen to the growing cells, it is necessary to ensure that the oxygen transfer from the air bubbles (gas phase) to the liquid phase occurs quickly. When no oxygen accumulates in the liquid phase, the rate of the oxygen transfer is the same as the rate of the oxygen uptake by the growing cells.

The oxygen requirements of microorganisms is defined as a standard formula, that is in units of $QO_2$. Where $QO_2$ is the mass of oxygen consumed divided by the unit weight of dry biomass cells in the bioreactor multiplied by time. Conversely, the rate of accumulation of oxygen is equal to the net rate of oxygen supply from air bubbles minus the rate of oxygen consumption by cells.

In addition to a multitude of bioreactor types, each bioreactor may utilize a particular impeller type or types, such as marine-type propellers, flat-blade turbines, disk flat-blade turbines, curved-blade turbines, pitched-blade turbines, paddles, and shrouded turbines. The impeller or turbine may create a vortex pattern of mixing in the bioreactor, or a uniform mixing.

In certain embodiments, the gas-enriched fluid of the present invention relates to a sustained bio-availability of the gas such that a gradual release of the gas occurs over time. This gradual or "time" release is beneficial to the vehicles, such as cultured cells, particularly when the gas released from the gas-enriched fluid comprises oxygen. Thus, fermentation, or the biochemical synthesis of organic compounds by cells 3310, typically involve a relatively fast growth phase, facilitated by the concentrations of diffused or dissolved gas in the broth 3312, as well as by temperature control and by mixing the medium 3304 and the cell culture 3310 in the fermentation chamber of the bioreactor 3306. Particular exemplary embodiments are depicted in the figures, but may include additional components or tanks. Mixing may be enhanced by rotating vanes or the like within bioreactor 3306, and by reintroduction of fresh and/or freshly re-diffused supplies of medium 3304 from any of the lines 3332, 3338 or 3334, as described herein inter alia.

In one particular exemplary embodiment depicted in FIG. 45A, the enrichment processing of the medium and/or broth to introduce the gas (e.g. oxygen) in a cell culture medium may occur at various points in the system. For example, the medium may be gas-enriched prior to introducing the medium 3304 into the system 3300a at source 3302, or after such introduction at one or more locations "A," "B," "C," "D," "E" or combinations thereof. Gas-enriched fluid that may be introduced at the source 3302, whether enriched at the site of the bioreactor or at a separate location. If the gas-enriched fluid is enriched at a separate location, it may be transported to the source 3302 in appropriate containers or plumbing.

In certain embodiments, each of the locations "A," "B," and "C," of FIG. 45A represent alternative locations for introduction of a gas-enrichment diffuser device 1—within the bioreactor system 3300A. In the event that the introduction occurs at point "A," the flow of medium from tank 3304 through the upper section of 3332A of 3332, the medium may be directed through the gas-enrichment mixer/diffuser device 100 located at position "A," and medium 3304 with dissolved gases therein proceeds from the mixer/diffuser device 100 through 3332B and into the fermentation chamber of the bioreactor 3306.

With reference to FIG. 45B, the medium 3304 from tank 3302 may be directed through line 3332A into a pump 3410 and, subsequently into the host material input of the gas-enrichment diffuser device 100. The pump 3410, is preferably a variable speed pump, which may be controlled by a controller 3390, based, in part, on pressure readings detected by pressure sensor 3415. While certain embodiments will utilize manual gauges as pressure detectors, from which an operator may manually adjust the speed of the pump 3410, and other components of the system 3300a or 3300b, controller 3390 preferably receives an electrical signal from sensor 3415 such that controller 3390 will automatically adjust the speed of pump 3410. As will be evident from further descriptions herein, the speed of pump 3410 may also be based on algorithms within the controller 3390 which depend, in part, on the state of other components of the system 3400 (such as valves 3420, 3421 and sensors 3425).

Alternatively, the gas-enrichment mixer/diffuser device 100 may be positioned at location "B" such that the medium 3304 is processed together with medium 3310. In this particular case, cells 3310 and medium 3304 are mixed in flow using a conventional mixing nozzle and subsequently introduced into the mixer/diffuser device 100, where beneficial gases are infused into the mixed liquid of medium 3304 and cells 3310. The resulting gas-enriched medium is then directed into the fermentation tank of the bioreactor 3306.

As shown in FIG. 45A, cells 3310 may be combined with medium 3304, and following fermentation and/or development of the target product, the contents of the bioreactor 3306 may then be directed through line 3336 to a harvesting and purification stage. Once purified, the target product is directed through line 3339 to a target production tank 3318.

With reference to FIG. 45B, in certain embodiments, the gas-enrichment mixer/diffuser device 100 combines the flow of a medium 3304 with a flow of a gas from line 3426. Preferably, the gas to be combined with medium 3304 flows from an oxygen tank 3450 and is metered by a valve 3420, which is controlled by controller 3390.

In certain embodiments, the gas-enrichment mixer/diffuser device 100 is directed through line 3332b directly into the fermentation tank by a reactor 3306. Alternatively, the gas-enriched fluid may be directed through line 3332b to another blending.

With reference to FIG. 45A, a bioreactor system 3300a, may include an additional system (such as a perfusion system) 3314 that begins processing the broth from the bioreactor 3306. During the perfusion process 3314, the medium 3304 is continuously added to the broth 3312 to nourish the cell culture 3310, which is then mixed throughout the broth 3312. Simultaneously, cell or other waste may be continuously removed from the broth 3312, typically at the same rate as new medium 3304 is added. As indicated herein above, gas-enrichment may also occur at positions "D" or "E," or at both positions "D" and "E."

The perfusion system can allow for removal of cellular waste and debris, as well as the target product, while retaining the cells in the bioreactor 3306. The perfusion system thus reduces waste accumulation and nutrient fluctuations, thereby allowing for higher cell density and productivity. Retention of the cells in the bioreactor may be achieved through various methods, including centrifugation, internal or external spin filters, hollow fiber modules, cross-flow filtration, depth filtration, any combination of these or other means. In other embodiments, the accumulation of waste products may be regulated by use of a glutamine synthetase expression system.

Figure 46:
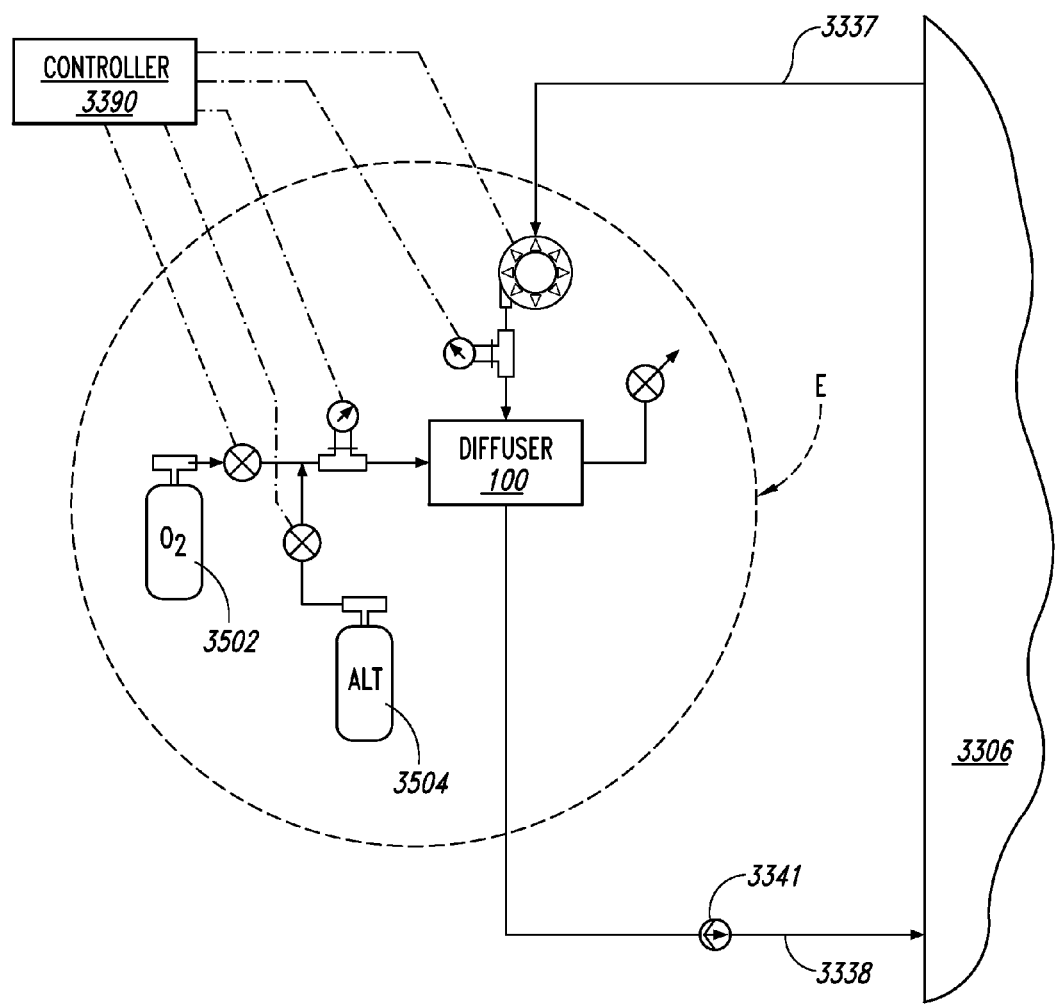
FIG. 46 shows detailed portions of exemplary embodiments of the bioreactor system 3300a of FIGS. 45A and 45B.

With reference to FIG. 46, particular exemplary embodiments utilize multiple gas sources 3502 and 3504 as shown, such that the nature of the gas being diffused into the broth 3312 can be changed depending on the stage of fermentation within the bioreactor 3306. Hence, in a preferred embodiment, the cell culture medium is enriched with oxygen during the proliferative phase of fermentation. Subsequently, carbon dioxide, nitrous oxide, or another gas may be substituted to facilitate other stages of the fermentation process, particularly with processes that vary from aerobic to anaerobic.

The bioreactor may comprise an airlift reactor, a packed bed reactor, a fibrous bed reactor, a membrane reactor, a two-chamber reactor, a stirred-tank reactor, a hollow-fiber reactor, or other reactor designed to support suspended or immobilized cell growth.

In one particular embodiment, the bioreactor 3306 is a continuous stirred-tank reactor, comprising heat exchange and refrigeration capabilities, sensors, controllers, and/or a control system to monitor and control the environmental conditions within the fermentation chamber. Monitored and controlled conditions may include gas (e.g. air, oxygen, nitrogen, carbon dioxide, nitrous oxide, nitric oxide, sulfur gas, carbon monoxide, hydrogen, argon, helium, flow rates, temperature, pH, dissolved oxygen levels, agitation speed, circulation rate, and others. Additionally, the bioreactor 3306 may further comprise Cleaning-in-Place (CIP) or Sterilization-in-Place (SIP) systems, which may be cleaned and/or sterilized without assembly or disassembly of the units.

In one particular embodiment, the bioreactor 3306 performs a continuous fermentation cycle, continuously adding medium 3304 to the fermentation system with a balancing withdrawal, or harvest, of the broth 3312 for target product extraction.

In alternate embodiments, the bioreactor 3306 may perform batch fermentation cycles, fed-batch fermentation cycles, or fed-batch fermentation cycles with the gas-enriched fluids. Typically, batch fermentation cycles—in which all of the reactants are loaded simultaneously—are used for small scale operations or for the manufacture of expensive products or for processes that may be difficult to convert into continuous operations. In a typical process, the broth is fermented for a defined period to completion, without further additions of the medium. The concentration varies with time, but is typically uniform at any one particular time point. Agitation serves to mix separate feed lines as well as enhance heat transfer.

For batch fermentation, typically the total mass of each batch is fixed, each batch is a closed system, and the reaction or residence time for all reactants of the medium is the same. After discharging the batch, the fermentation chamber is cleaned and re-started with the medium 3304 for another batch cycle. Separation or purification of the desired product from the other constituents in the harvest broth 3312, may include further processing, including refolding, altering affinity, ion exchange purification, alteration of hydrophobic interactions, gel filtration chromatography, ultra filtration and/or diafiltration, depending on the target product.

For fed-batch fermentation, typically an initial, partial charge or aliquot of medium 3304 is added to the fermentation chamber, and subsequently inoculated with cell culture 3304. The medium 3304 may be added at measured rates during the remainder of the fermentation cycle. The cell mass and the broth 3312 are typically harvested only at the end of the cycle.

Following harvest and purification of the target product (step 3316), (typically once the cell culture 3310 has attained a peak cell growth density within the bioreactor 3306), the purified product 3318 (in some cases, a pharmaceutical drug or Active Pharmaceutical Ingredient, or API) is attained. The purified product may then be processed as desired and optionally packaged in appropriate containers during a sterile packaging process 3322 for transfer to a pharmaceutical manufacturing plant, or other facility. The purified product may then be used for any desired purpose, including for prevention, treatment, and/or diagnosis of disease.

Plants and Animals as Reactors

In addition, a reactor may include a plant or animal, which is used to generate a plant or animal product, or recombinant product. In certain embodiments, the plant or animal target product may be a naturally occurring product (e.g., food bearing crops or meat, or textile-related products such as cotton fibers, etc.), or the target product may be a genetically altered product (for example, therapeutic agents, such human growth hormone or insulin or other biologically active proteins and polypeptides). A genetically altered or recombinant product may be produced by a transgenic or genetically altered plant, animal, or combination thereof.

Fish Culture

Fish (e.g., Tilapia fish) may be grown in aquaculture for food, or as a transgenic vehicle for production of a target product. The preferred temperature range for optimum tilapia growth is 82°-86° F. Growth diminishes significantly at temperatures below 68° F. and death will typically occur below 50° F. Also, at temperatures below about 54° F., the immune resistance of tilapia declines and the animals are easily subjected to infection by bacteria, fungi, and parasites.

Twenty years ago, aquaculture researchers in Nigeria attempted to correlate dissolved oxygen concentrations in pond waiter with Tilapia growth rates. UN FAO reports: The study was conducted by examining growth rates of young Tilapia at high dissolved oxygen levels (approximately 7.0 ppm); at mid-level DO (approximately 3.5 ppm); and at low DO levels (less than 2 ppm). The growth rates were determined by measuring the weight of the fish. The final increase in weight at the end of the research was 19 grams for the high DO level fish; 5 grams for the mid-level DO fish; and 1.5 g for the low DO level fish. This represents to a 74% and 92% reduction in growth rates correlating to the DO levels. Thus, as the DO levels decrease, the feeding and waste output also decrease. It was observed that the Tilapia in the low DO level water break the surface of the water in order to access ambient oxygen required for survival.

The gas-enriched fluids of the present invention further include oxygenated freshwater supplies in which the high dissolved oxygen levels in the water are maintained for extended periods of time. According to particular aspects, using the diffuser device of the present invention in an aquaculture setting, dissolved oxygen levels of over 35 ppm can be recorded in 103° F. water without significantly stressing the aquatic life.

Plant Growth

In addition to animal growth, the gas-enriched fluids of the present invention may be utilized for plant growth and development. Gases (such as oxygen) are required for plant root respiration, which allows for the release of energy for growth, as well as water and mineral uptake. Plant growth has been widely and unequivocally proven to be boosted by maintaining high gas (e.g. oxygen and/or nitrogen) levels within the root zone. In this regard, increasing gas delivery to plant root systems represents a potential for crop improvement through boosting root activity. Likewise, in embodiments in which transgenic plants are grown, increasing gas delivery to the plants may provide for increased production of the target product (such as a therapeutic or biopharmaceutical product).

Hydroponic crops represent one exemplary system for production which may greatly benefit from the gas-enrichment diffuser devices of the present invention through direct gas-enrichment (e.g. oxygenation) of the nutrient solution bathing the root zone. Hydroponic crops are typically produced in a limited volume of growing media or root area and as such need constant replacement of gases (e.g. oxygen) within the root zone. Hydroponic crops such as lettuce, spinach, tomatoes, and cucumbers have already demonstrated a direct and significant response to the gas-enriched nutrient solution. Some of these responses include increases in plant growth, increases in root volume, increases in plant yield, and higher quality produce. Thus, hydroponic systems may benefit from the gas-enriched fluids of the present invention.

Other hydroponic crops have had similar responses to gas-enrichment in the root zone. However, at warm temperatures, crop production declines due to the increased requirement for gases (such as oxygen) in the root zone. Thus, enrichment is effective for preventing gas-starvation of root cells, as well as boosting growth under less than favorable growing conditions.

Typically tropical crops that are able to be grown at high densities due to high light levels and rapid rates of development (and high root zone temperatures) have a gas requirement that is many times greater than those grown in more temperate climates. Thus, gas-enrichment will become necessary in many systems of horticulture production. Highly populated countries, which rely heavily on producing intensive horticultural crops for income and sustenance from very limited areas of land, will benefit greatly from this technology.

Soil-based cropping systems can also benefit from the gas-enriched solutions of the present invention. Many crops are fed via drip, trickle, or furrow irrigation and could potentially benefit greatly from the use of gas-enriched irrigation water or fertigation solutions. Such crops include, but are not limited to: vegetables (tomatoes, salad crops such as lettuce, herbs, cucurbits), cut flowers, ornamental flowers, turf, vineyards, orchards, and long-term plantings. Gases, such as oxygen, can directly impact the health and growth of the plant but can also act indirectly by increasing the bio-availability of gases (e.g. oxygen) at the root zone, and can also improve the health of the plant by promoting microbial life in the soil.

With regard to the microbial life in the soil, the microbial populations are essential for mineral conversion in the soil and organic systems and overall plant health through suppression of plant diseases. While these microbes are beneficial and often essential for crop production, the populations also require gases (e.g. oxygen), which can compete with the gases for plant root cells. Thus, supplying gases (e.g. oxygen) to the plant roots in order to enable microbial life to flourish is vital to both organically grown crops, as well as standard growing conditions. High rates of gases supplied to the growing media/soil in organic systems would potentially speed up the rate of organic fertilizer conversion and mineralization of plant usable nutrients, thus increasing the health and productivity of highly profitable organic crops.

In addition, the available land for growing crops represents a challenge in many countries with limited resources or unsuitable soils.

In addition to hydroponic crops, the technology disclosed herein may apply to seed germination, seed raising, cell transplant production, propagation from cuttings, sprout production, animal fodder production, soil based cropping, turf industries, ornamental plants, and medicinal plants.

Systems for Making Gas-Enriched Fluids

As shown here, exemplary oxygenation systems comprises a supply or reservoir of fluid which is drawn up and circulated through tubing or other conduits by a pump which subsequently delivers the fluid to the mixer/diffuser. The mixer/diffuser may be of any number of various embodiments including those set forth and described herein above. These diffusers significantly increase the amount of dissolved gas (e.g., oxygen) present in a fluid by introducing, for example, gaseous oxygen to the fluid using a diffuser having coaxial cylindrical or frusto conical stator and rotor components rotating discs or plates within a housing, Mazzie diffusers and impellers to create the desired cavitation and succussion desired for mixing of the fluid and the gas. It should be noted that many of the fluids will be aqueous or water-based, but that the present invention is not limited to these.

The diffuser is supplied with fluid by the pump and combines this with, for example, gaseous oxygen from supply and returns the oxygenated (or otherwise gas-enriched) fluid to the reservoir. The diffuser may employ any number of possible embodiments for achieving diffusion including, but not limited to, micro-membrane, Mazzie injector, fine bubble, vortexing, electromolecular activation, or other methods. The oxygen supply may be either a cylinder of compressed oxygen gas or a system for generating oxygen gas from the air or other chemical components. The oxygenated fluid produced by the diffuser is returned to the reservoir and may be recirculated through the pump and/or the diffuser again to further increase the dissolved oxygen content. Alternatively, the fluid may be drawn off using the oxygenated fluid outlet. Oxygenated fluids which are drawn off through the outlet may be immediately put to use in various applications or may be packaged for later use.

The packaging step may enclose gas-enriched (e.g. oxygenated) fluids in a variety of bottles, bags or other containers formed of plastic, metal, glass, or other suitable materials. Although the gas-enriched or oxygenated fluids produced in accordance with the present invention have a relatively long shelf life under atmospheric conditions, the shelf life may be further extended by using packaging which hermetically seals the gas-enriched fluid. In this manner, dissolved oxygen which works its way out of the fluid during storage will form a pressure head above the gas-enriched fluid and help to prevent the migration of dissolved oxygen, or other gas, out of the fluid and back into the atmosphere. In one preferred embodiment of the present invention the gas-enriched fluid is packaged in an air tight container and the void space is filled with the gas used for enrichment at a pressure of greater than one atmosphere prior to sealing the container. The packaging step may be used to produce bottles, bags, pouches, or other suitable containers for holding oxygenated solutions.

The presently disclosed systems and/or methods allow oxygen, or other gases, to be dissolved stably at a high concentration with minimal passive loss. These systems and/or methods can be effectively used to dissolve a wide variety of gases at heightened percentages into a wide variety of fluids. By way of example only, a deionized water at room temperature that typically has levels of about 7-9 ppm (parts per million) of dissolved oxygen can achieve levels of dissolved oxygen ranging from about 8-70 ppm using the disclosed systems and/or methods. In accordance with a particular exemplary embodiment, an oxygenated water or saline solution may be generated with levels of about 30-60 ppm of dissolved oxygen.

Culturing Chinese Hamster Ovary Cells

Chinese Hamster Ovary (CHO) cells are mammalian cells that are frequently utilized in expression and production of recombinant proteins, particularly for those that require post-translational modification to express full biological function.

According to particular aspects, various characteristics of CHO cells can be improved by integrating either a gas-enriching diffuser device 100 or gas-enriched media produced by the device 100 and integrated into a CHO bioreactor.

According to particular aspects, in the cultivation of CHO cells, it is possible to utilize the gas-enriched fluids or media of the present invention including with a cell-line specific, serum-free medium (for example from SAFC Biosciences, Inc.) for long-term growth of transformed CHO cells. According to additional aspects, CHO cells are not harmed by passing through the gas-enrichment diffuser device in the process of gas-enriching fluids (including media).

A test was conducted that measured the survival of CHO cells in an inline bioreactor. Briefly, the inline bioreactor was used with 2 L of CHO media, and CHO cells at a density of $10^6$ or higher. The bioreactor was run for approximately 10 minutes (including the gas-enriching diffuser), and a 25 mL sample was removed. Cells were stained with 0.4% Trypan Blue, and cell viability was assessed with a hemacytometer. According to this measure, CHO cells were not significantly harmed by passing through the gas-enrichment diffuser device in the process of gas-enriching fluids (including media).

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"). the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A mixing device for creating an output mixture by mixing a first material and a second material, the device comprising:
   a first chamber configured to receive the first material from a source of the first material;
   a stator;
   a rotor having an axis of rotation, the rotor being disposed inside the stator and configured to rotate about the axis of rotation therein, at least one of the rotor and stator having a plurality of through-holes;
   an arcuate mixing chamber defined between the rotor and the stator, the arcuate mixing chamber having an open first end through which the first material enters the mixing chamber and an open second end through which the output material exits the mixing chamber, the second material entering the mixing chamber through the plurality of through-holes formed in the at least one of the rotor and the stator; and
   a first internal pump housed inside the first chamber, the first internal pump being configured to pump the first material from the first chamber into the arcuate mixing chamber.

2. The mixing device of claim 1, wherein the first internal pump is configured to impart a circumferential velocity into the first material before it enters the arcuate mixing chamber.

3. The mixing device of claim 2, wherein the rotor imparts a mixing circumferential velocity into the first material and the second material inside the arcuate mixing chamber, and the circumferential velocity imparted into the first material by the first internal pump approximates the mixing circumferential velocity imparted by the rotor.

4. The mixing device of claim 1, further comprising a drive shaft coupled to the rotor and extending though the first chamber along the axis of rotation, the drive shaft being configured to rotate the rotor about the axis of rotation and to power to the first internal pump.

5. The mixing device of claim 4, wherein the rotor has a sidewall defining a hollow portion into which the drive shaft extends, the sidewall has a plurality of openings providing communication between the hollow portion and the mixing chamber, and the drive shaft comprises an internal channel having a first opening into the hollow portion of the drive shaft and a second opening, the mixing device further comprising a source of the second material, the source being coupled to the second opening of the channel and the source being configured to supply the second material into the arcuate mixing chamber through the channel, the hollow portion of the rotor, and the plurality of openings of the sidewall of the rotor.

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
taatacgact cactataggg                                           20

6. The mixing device of claim 1, wherein the stator comprises a plurality of through-holes, the mixing device further comprising:
a housing comprising an input port, the stator being housed inside the housing;
a channel defined between the housing and the stator, the input port being in communication with the channel, the plurality of through-holes of the stator providing communication between the arcuate mixing chamber and the channel; and
a source of a third material coupled to the input port and configured to supply the third material to arcuate mixing chamber through the input port, the channel, and the plurality of through-holes of the stator.

7. The mixing device of claim 1, further comprising:
a second chamber in fluid communication with the arcuate mixing chamber and configured to receive the output material therefrom; and
a second internal pump housed inside the second chamber, the second internal pump being configured to pump the output material from the arcuate mixing chamber into the second chamber.

8. The mixing device of claim 1, further comprising:
a second chamber in fluid communication with the arcuate mixing chamber and configured to receive the output material therefrom;
a drive shaft coupled to the rotor and extending though the first chamber, the rotor, and the second chamber along the axis of rotation; and
a second internal pump housed inside the second chamber, the second internal pump being configured to pump the output material from the arcuate mixing chamber into the second chamber, the drive shaft being configured to rotate the rotor about the axis of rotation and to power to the second internal pump.

9. The mixing device of claim 1, further comprising:
a second chamber in fluid communication with the arcuate mixing chamber and configured to receive the output material therefrom; and
a second internal pump housed inside the second chamber, the second internal pump being configured to pump the output material from the arcuate mixing chamber into the second chamber, and to impart a circumferential velocity into the output material after it enters the arcuate mixing chamber.

10. The mixing device of claim 1, wherein both the rotor and the stator have a substantially cylindrical shape with a longitudinal axis aligned along the axis of rotation, and the arcuate mixing chamber has a ring-shaped cross-sectional shape having a thickness of about 0.02 inches to about 0.08 inches.

11. The mixing device of claim 1, wherein the rotor rotates about the axis of rotation in a rotation direction having an tangential component, the first chamber comprises an input port configured to receive the first material from a source of the first material, the input port being configured to introduce the first material into the first chamber traveling in a direction substantially equivalent to the tangential component of the rotation direction.

12. The mixing device of claim 11, wherein the first chamber has an internal shape configured to deflect the first material and direct it to flow in the rotation direction.

13. The mixing device of claim 11, further comprising a second chamber in fluid communication with the arcuate mixing chamber and configured to receive the output material therefrom, the second chamber comprising an output port through which the output material may exit the mixing device, the input port being configured to allow the output material to exit the second chamber traveling in a direction substantially equivalent to the tangential component of the rotation direction.

14. The mixing device of claim 13, wherein the second chamber has an internal shape configured to deflect the output material and direct it to flow in the rotation direction.

15. A mixing device for creating an output mixture by mixing a first material and a second material, the device comprising:
a stator;
a rotor having an axis of rotation, the rotor being disposed inside the stator and configured to rotate about the axis of rotation therein, at least one of the rotor and stator having a plurality of through-holes;
a mixing chamber defined between the rotor and the stator, the mixing chamber having an open first end through which the first material enters the mixing chamber and an open second end through which the output material exits the mixing chamber, the second material entering the mixing chamber through the plurality of through-holes formed in the at least one of the rotor and the stator;
a first chamber in communication with at least a majority portion of the open first end of the mixing chamber; and
a second chamber in communication with the open second end of the mixing chamber.

16. An output mixture produced by the mixing device of claim 15.

17. The mixing device of claim 15, wherein the second chamber is in communication with at least a majority portion of the open second end of the mixing chamber.

18. The mixing device of claim 15, further comprising:
a first internal pump housed inside the first chamber and configured to pump the first material from the first chamber into the open first end of the mixing chamber and to impart a circumferential velocity into the first material before it enters the open first end of the mixing chamber.

19. The mixing device of claim 18, further comprising:
a second internal pump housed inside the second chamber and configured to pump the output material from the open second end of the mixing chamber into the second chamber and to impart a circumferential velocity into the second material after it exits the mixing chamber.

20. The mixing device of claim 15, wherein the first chamber comprises an input port coupled to an external pump, the external pump configured to pump the first fluid into the first chamber, the input port being positioned to introduce the first material into the first chamber traveling in a direction substantially tangential to the axis of rotation, the first chamber having an internal shape configured to deflect the first material traveling in a direction substantially tangential to the axis of rotation into a circumferential flow about the axis of rotation.

21. A bioreactor system, comprising a bioreactor in combination with the mixing device of any one of claims 1 and 15, or with a gas-enriched fluid derived using the mixing device of any one of claims 1 and 15.

22. A method of mixing a first material and a second material in an cylindrical mixing chamber formed between two contoured surfaces to create an output mixture, the cylindrical mixing chamber having a first end portion opposite a second end portion, the method comprising:
introducing the first material into the first end portion of the cylindrical mixing chamber in a flow direction having a first component that is substantially tangent to the cylindrical mixing chamber and a second component that is directed toward the second end portion; and introducing the second material into the cylindrical mixing chamber though at least one of the two contoured surfaces between the first end portion of the cylindrical mixing chamber and the second end portion of the cylindrical mixing chamber.

23. The method of claim 22, wherein the first end portion of the mixing chamber is coupled to a first chamber, the method further comprising:

before introducing the first material into the first end portion of the cylindrical mixing chamber, introducing the first material into the first chamber, and imparting a circumferential flow into the first material in the first chamber.

24. The method of claim 22, wherein the first end portion of the mixing chamber is coupled to a first chamber, the mixing chamber is formed between an outer contoured surface of a rotating cylindrical rotor and an inner contoured surface of a stationary cylindrical stator, and the rotor rotates inside the stator about an axis of rotation, the method further comprising:

before introducing the first material into the first end portion of the cylindrical mixing chamber, introducing the first material into the first chamber, and imparting a circumferential flow substantially about an axis of rotation into the first material in the first chamber;

introducing the second material into a hollow portion of a rotating rotor having a plurality of through-holes, each through-hole of the plurality extending from the hollow portion to the outer contoured surface of the rotor;

flowing the second material from the hollow portion of the rotating rotor through the plurality of through-holes into the mixing chamber;

flowing the first material from the first chamber into the mixing chamber; and rotating the rotor relative to the stator thereby mixing the first material and the second material together inside the mixing chamber.

* * * * *